US006472588B1

(12) United States Patent
Haigler et al.

(10) Patent No.: US 6,472,588 B1
(45) Date of Patent: Oct. 29, 2002

(54) TRANSGENIC COTTON PLANTS WITH ALTERED FIBER CHARACTERISTICS TRANSFORMED WITH A SUCROSE PHOSPHATE SYNTHASE NUCLEIC ACID

(75) Inventors: Candace H. Haigler; A. Scott Holaday, both of Lubbock, TX (US)

(73) Assignee: Texas Tech University, Lubbock, TX (US)

( * ) Notice: Subject to any disclaimer, the term of this patent is extended or adjusted under 35 U.S.C. 154(b) by 0 days.

(21) Appl. No.: 09/394,272

(22) Filed: Sep. 10, 1999

(51) Int. Cl.[7] .............................. A01H 5/00; A01H 5/10; C12N 15/82

(52) U.S. Cl. ........................ 800/314; 800/278; 800/284; 800/286; 800/287

(58) Field of Search .............................. 435/69.1, 320.1, 435/419, 468; 536/23.2, 23.6; 800/278, 298, 314, 284, 286, 287

(56) References Cited

U.S. PATENT DOCUMENTS

| | | | |
|---|---|---|---|
| 5,004,863 A | 4/1991 | Umbeck | 800/205 |
| 5,159,135 A | 10/1992 | Umbeck | 800/205 |
| 5,387,756 A | 2/1995 | Burrell et al. | 800/205 |
| 5,498,831 A | 3/1996 | Burgess et al. | 800/205 |
| 5,536,653 A | 7/1996 | Barry et al. | 435/172.3 |
| 5,608,150 A | 3/1997 | Conner | 800/205 |
| 5,646,023 A | 7/1997 | Secor et al. | 435/172.3 |
| 5,665,892 A | 9/1997 | Van Assche et al. | 800/205 |
| 5,693,506 A | 12/1997 | Rodriguez | 435/172.3 |
| 5,714,365 A | 2/1998 | Van Assche et al. | 435/194 |
| 5,716,837 A | 2/1998 | Barry et al. | 435/240.4 |
| 5,723,752 A | 3/1998 | Houtz | 800/205 |
| 5,767,365 A | 6/1998 | Sonnewald | 800/205 |
| 5,866,790 A | 2/1999 | Hesse et al. | 800/205 |
| 5,914,446 A | 6/1999 | Shewmaker | 800/205 |
| 5,981,852 A | 11/1999 | Van Assche et al. | 800/317.4 |

FOREIGN PATENT DOCUMENTS

| | | |
|---|---|---|
| WO | WO 94/04693 | 3/1994 |
| WO | WO 97/15678 | 5/1997 |

OTHER PUBLICATIONS

Koziel, M. G. et al. "Optimizing expression of transgenes with an emphasis on post-transcriptional events." 1996, Plant Molecular Biology, vol. 32, pp. 393–405.*

Stam, M. et al. "The Silence of Genes in Transgenic Plants." 1997, Annals of Botany, vol. 79, pp. 3–12.*

Smith, C. J. S. et al. "Antisense RNA inhibition of polygalacturonase gene expression in transgenic tomatoes." 1988, Nature, vol. 334, pp. 724–726.*

Foyer et al., "Modulation of Carbon and Nitrogen Metabolism in Transgenic Plants with a View to Improved Biomass Production," *Biochem. Soc. Transactions: Transgen. Plants and Plant Biochem.* 22:909–915 (1994).

Worrell et al., "Expression of a Maize Sucrose Phosphate Synthase in Tomato Alters Leaf Carbohydrate Partitioning," *The Plant Cell*, 3:1121–1130 (1991).

Galtier et al., "Effects of Elevated Sucrose–Phosphate Synthase Activity on Photosynthesis, Assimilate Partitioning, and Growth in Tomato (*Lycopersicon esculentum* var UC82B)," *Plant Physiol.*, 101:535–543 (1993).

Galtier et al., "Effects of Light and Atmospheric Carbon Dioxide Enrichment on Photosynthesis and Carbon Partitioning in the Leaves of Tomato (*Lycopersicon esculentum* L.) Plants Over–Expressing Sucrose Phosphate Synthase," *J. Experimental Botany*, 46:1335–1344 (1995).

Micallef et al., "Altered Photosynthesis, Flowering, and Fruiting in Transgenic Tomato Plants That Have an Increased Capacity for Sucrose Synthesis," *Planta*, 196:327–334 (1995).

Laporte et al., "Sucrose–Phosphate Synthase Activity and Yield Analysis of Tomato Plants Transformed with Maize Sucrose–Phosphate Synthase," *Planta*, 203:253–259 (1997).

Signora et al., "Over–Expression of Sucrose Phosphate Synthase in *Arabidopsis thaliana* Results in Increased Foliar Sucrose/Starch Ratios and Favours Decreased Foliar Carbohydrate Accumulation in Plants After Prolonged Growth with $CO_2$ Enrichment," *J. Experimental Botany*, 49(321):669–680 (1998).

Krause et al., "Sucrose Metabolism in Cold–Stored Potato Tubers with Decreased Expression of Sucrose Phosphate Synthase," *Plant, Cell and Environ.*, 21:285–299 (1998).

Ferrario–Méry et al., "Manipulation of the Pathways of Sucrose Biosynthesis and Nitrogen Assimilation in Transformed Plants to Improve Photosynthesis and Productivity," in Foyer and Quick, eds., *A Molecular Approach to Primary Metabolism in Higher Plants*, Taylor & Francis, pp. 125–153 (1997).

Foyer et al., "Source–Sink Interaction and Communication in Leaves," in Zamski and Schaffer, eds., *Photoassimilate Distribution in Plants and Crops*, New York, New York-:Marcel Dekker, Inc., pp. 311–340 (1996).

Sonnewald et al., "Manipulation of Sink–Source Relations in Transgenic Plants," *Plant, Cell and Environ.*, 17:649–658 (1994).

(List continued on next page.)

*Primary Examiner*—Amy J. Nelson
(74) *Attorney, Agent, or Firm*—Nixon Peabody LLC

(57) ABSTRACT

The present invention provides methods for increasing the quality of cotton fiber produced from a cotton plant by transformation with a DNA encoding sucrose phosphate synthase. In particular the fiber qualities include strength, length, fiber fineness, fiber maturity ratio, immature fiber content, fiber uniformity, and micronaire.

16 Claims, 12 Drawing Sheets

OTHER PUBLICATIONS

Frommer et al., "Molecular Analysis of Carbon Partitioning in Solanaceous Species," *J. Experimental Botany*, 46(287):587–607 (1995).

Stitt, "The Use of Transgenic Plants to Study the Regulation of Plant Carbohydrate Metabolism," *Aust. J. Plant Physiol.*, 22:635–646 (1995).

Stitt et al., "Regulation of Metabolism in Transgenic Plants," *Annu. Rev. Plant Physiol. Plant Mol. Biol.*, 46:341–368 (1995).

Huber et al., "Role and Regulation of Sucrose–Phosphate Synthase in Higher Plants," *Annu. Rev. Plant Phisiol. Plant Mol. Biol.*, 47:431–444 (1996).

Kossmann et al., "Potential for Modifying Source–Sink Interactions Through the Genetic Manipulation of Carbohydrate Metabolism," in Zamski and Schaffer, eds., *Photoassimilate Distribution in Plants and Crops*, New York, New York: Marcel Dekker, Inc., pp. 369–387 (1996).

Sonnewald, "Modulation of Sucrose Metabolism," in Foyer and Quick, eds., *A Molecular Approach to Primary Metabolism in Higher Plants*, Taylor & Francis, pp. 63–79 (1997).

Amor et al., "A Membrane–Associated Form of Sucrose Synthase and Its Potential Role in Synthesis of Cellulose and Callose in Plants," *Proc. Natl. Acad. Sci. USA* 92(20):9353–9357 (1995).

* cited by examiner cs = CELLULOSE SYNTHASE
hk = HEXOKINASE
pgi = PHOSPHOGLUCOISOMERASE
pgm = PHOSPHOGLUCOMUTASE
spp = SUCROSE PHOSPHATE PHOSPHATASE
sps = SUCROSE PHOSPHATE SYNTHASE
ss = SUCROSE SYNTHASE
UDPG-PPiase = UDPG-PYROPHOSPHORYLASE

FIG. 3A

PLANT SPS AMINO ACID ALIGNMENT

```
                        9        19        29        36        46        56        66        76        86
Spinach SPS1      MAGND-WINSYLEAILDVGGQGIDASTGKTST--------------------------APPSLLLRERGHFSPSRYFVEEVISGFDETDLHRSWVRAASTRSPQERNTRLENL
Citrus unshiu     MAGND-WINSYLEAILDVG-PGLDD-----------------------------------AKSSLLLRERGRFSPTRYFVEEVITGFDETDLHRSWVKAQATRSPQERNTRLENM
C. plantagineum 1 MAGND-WINSYLEAILDVG-PGIDE-----------------------------------AKGSLLLRERGRFSPTRYFVEEVVSGFDETDLHRSWIRAQATRSPQERNTRLENM
C. plantagineum 2 MAGNE-WINGYLEAILDTGASAIDENSGGG------------------------------KTAAAQKGRHHDHHFNPTKYFVEEVVSGVDESDLHRTWIKVVATRNTRERSSRLENM
Vicia faba        MAGND-WLNSYLEAILDVG-PGLDD-----------------------------------AKSSLLLRERGRFSPTRYFVEEVI-GFDETDLYRSWVRASSSRSPQERNTRLENM
S. tubersom       MAGND-WINSYLEAILDVG-PGLDD-----------------------------------HKSSLLLRERGRFSPTRYFVEEVITGFDETDLHRSWIRAQATRSPQRRNTRLENM
Beta vulgaris     MAGND-WINSYLEAILDVG-PGLDD-----------------------------------AKSSLLLRERGRFSPTRYFVEEVITGFDETDLHRSWVRAQATRSPQERNTRLENM
Zea mays          MAGNE-WINGYLEAILDSHTSSRGAGGGGGGG---------------------DPRSPTK-AASPRGAHMN--FNPSHYFVEEVVKGVDESDLHRTWIKVVATRNARERSTRLENM
Orysa sativa 1    MAGNE-WINGYLEAILDSGGAAGGGGGGGGGGGGGGGGGGG------------DPRSPTTGTTSPRGPHMN--FNPTHYFVEEVVKGVDESDLHRTWIKVVATRNARERSTRLENM
Orysa sativa 2    MAGNE-WINGYLEAILDSGGAAGGGGGG-----------------------VDPRSPAAGAASPRGPHMN--FNPTHYFVEEVVKGVDESDLHRTWIKVVATRNARERSTRLENM
A. thaliana 1     MARND-WINSYLEAILDVGTSKKKRFESNSKIVQKLG-----------DINSKDHQEKVFGDMNGKDHQEKVFSPIKYFVEEVVNSFDESDLYKTWIKVIATRNTRERSNRLENI
A. thaliana 2     MAGNDNWINSYLDGILDAGKAIGG------------------------------------NRPSLLLRERGHFSPARYFVEEVITGYDETDLYKTWLRANAMRSRREEHA-LENM
S. officinarum    MAGNDNWINSYLDGILDAGKAIGG------------------------------------NRPSLLLRERGHFSPARYFVEEVITGYDETDLYKTWLRANAMRSRREEHA-LENM
                  ** *: *:*.***:                                                  **: * ********:.   **:*:* :***:*** *  ..:.   ***:

96       106       116       126       136       146       151       161       171       180
Spinach SPS1      CWRIWNLARKKKQIEGEEAQRLAKRHVRERGRREATADMSEDLSEGERGDTVADMLFAS-------ESTKGRMRIISSVEMMDNWANTFKE-KKLYVVLIS-----------
Citrus unshiu     CWRIWNLARQKKQLEGEAAQRMAKRLERERGRREATADMSEDLSEGEKGDIVSDVSAHG-------DSTRSRLPRISSVDAMETWISQQKG-KKLYIVLIS-----------
C. plantagineum 1 CWRIWNLARQKKQLENEEAQRMAKRLERERGRREAVADMSEDLSEGEKGDIVVDHSHHG-------ESNRGRLPRINSVDTMEAWMNQQKG-KKLYIVLIS-----------
C. plantagineum 2 CWRIWHLTRKKKQLEWEDLQRLAARKWEREQGRKDVTEDMSEDLSEGEKGDVMGETPVALDS----PRGNKKYHRNESNLEV--WSDSNKE-KKLYIVLIS-----------
Vicia faba        CWRIWNLARQKKQLESEAVQRVNKRLERERGRREATADMSEDLSEGERGDPVSDVSTHGG------DSVKSRLPRISSADAMETWVNSQKG-KKLYIVLIS-----------
S. tubersom       CWRIWNLARQKKQLEGEQAQWMAKRRQERERGRREAVADMSEDLSEGEKGDIVADMSSHG------ESTRGRLPRISSVETMEAWVSQQRG-KKLYIVLIS-----------
Beta vulgaris     CWRIWNLARQKKQLENEEAQRKTKGRMELERGRREATADMSEDLSEGEK----DISAHG-------DSTRPRLPRINSLDAMETWISQQKE-KKLYLVLIS-----------
Zea mays          CWRIWHLARKKKQLELEGIQRISARRKEQEQVRREATEDLAEDLSEGEKGDTIGELAPVET-----TKKKFQRNFSDLITV--WSDDNKE-KKLYIVLIS-----------
Orysa sativa 1    CWRIWHLARKKKQLELEGILRISARRKEQEQVRRETSEDLAEDLFEGEKADTVGELAQQDTP----MKKKFQRNFSELTVS-WSDENKE-KKLYIVLIS-----------
Orysa sativa 2    CWRIWHLARKKKQLELEGILRISARRKEQBQVRRETSEDLAEDLFEGEKADTVGELAQQDTP----MKKKFQRNFSELTVS-WSDENKE-KKLYIVLIS-----------
A. thaliana 1     CWRIWHLARKKKQIVWDDGVRLSKRRIEREQGRNDAEEDLLSELSEGEKDKNDGEKEKSEVVTLEPPRDHMPRIRSEMQI--WSEDDKSSRNLYIVLIRQVEIGFSDLF
A. thaliana 2     TWRIWNLARKKKEFEKEEACRLSKRQPETEKTRADATADMSEDLFEGEKGEDAGDPSVAYG-----DSTTGSSPKTSSID-------------KLYIVLIS-----------
S. officinarum    TWRIWNLARKKKEFEKEEACRLSKRQPETEKTRADATADMSEDLFEGEKGEDAGDPSVAYG-----DSTTGSSPKTSSID-------------KLYIVLIS-----------
                  ****::** ::.                                                                 :                 :**:****

187       197       207       217       227       237       247       257
Spinach SPS1      -----LHGLIRGENMELGRDSDTGGVKYVVELARALGSMPGVYRVDLLTRQVSAPGVDWSYGEPTEMLSSRNSENSTEQ------LG
Citrus unshiu     -----IHGLIRGENMELGRDSDTGGQVKYVVELARALGSMPGVYRVDLLTRQVSAPDVDWSYGEPTEMLTPRNSDDEMDD-----MG
C. plantagineum 1 -----LHGLIRGENMELGRDSDTGGQVKYVVELARALGSMPGVYRVDLLTRQVSSPEVDWSYGEPTEMLPPRNSENMMDE-----MG
C. plantagineum 2 -----LHGLIRGENMELGRDSDTGGQIKYVVEVARALAKMPGVYRVDLFTRQISSPEVDWSYAEPTEMLSSSSTTAGEAHEPEEEEEEDLG
Vicia faba        -----LHGLIRGENMELGRDSDTGGQVKYVVELARALGSMPGVYRVDLLTRQVSSPDVDWSYGEPTEMLAPRNTDEFGDD-----MG
S. tubersom       -----LHGLIRGENMELGRDSDTGGQVKYVVELARALGSMPGVYRVDLLTRQVSSPEVDWSYGEPTELAP-ISTDGLMTE-----MG
Beta vulgaris     -----LHGLIRGENMELGRDSDTGGQVKYVVELARAMSMMPGVYRVDLFTRQVSSPDVDWSYGEPTEMLNPRDSNGFDDDD----DEMG
Zea mays          -----VHGLVRGENMELGRDSDTGGQVKYVVELARAMSMMPGVYRVDLFTRQVSSPDVDWSYGEPTEMLCAGSN----------DGEGMG
Orysa sativa 1    -----LHGLVRGDNMELGRDSDTGGQVKYVVELARALAMMPGVYRVDLFTRQVSSPEVDWSYGEPTEMLTSGST----------DGEGSG
Orysa sativa 2    -----LHGLVSGDNMELGRDSDTGGVKYVVELARALAMMPGVYRVDLFTRQVSSPEVDWSYGEPTEMLTP-------------VPLTE
A. thaliana 1     VVNMLVGLTWCLYLVPCFTNCSMHGLVRGENMELGRDSDTGGVKYVVELARALANTEGVHRVDLLTRQISSPEVDYSYGEPVEMLSCP-E------GS
A. thaliana 2     -----LHGLVRGENMELGRDSDTGGQVKYVVELAKALSSSPGVYRVDLLTRQILAPNFDRSYGEPAELLVSTSGKNSKQE-----KG
S. officinarum    -----LHGLVRGENMELGRDSDTGGQVKYVVELAKALSSSPGVYRVDLLTRQILAPNFDRSYGEPAELLVSTSGKNSKQE-----KG
                   :***:*:****: ****:**:******** :  ** .   *  *: *  : ** :* :  ** :*:
```

FIG. 3A

```
                    267       277       284       294       304       314       324       334       344       354       364
                     |         |         |         |         |         |         |         |         |         |         |
Spinach SPS1        ESSGAYIIRIPFGPDKYVAKELLWP---YIPEFVDGALSHIKQMSKVLGEQIGGGLPVWPASVHGHYADAGDSAALLSGALNVPMVFTGHSLGRDKLDQLLKQGRLSRE
Citrus unshiu       ESSGAYIIRIPFGPDKYIAKELLWP---HIPEFVDGALNHIIRMSNVLGEQIGGGKPVWPVAIHGHYADAGDSAALLSGALNVPMLFTGHSLGRDKLEQLLKQARLSRD
C. plantagineum 1   ESSGSYIVRIPFGPDKYVAKELLWP---HIPEFVDGALGHIIQMSKVLGEQIGNGHPIWPAAIHGHYADAGDSAALLSGALNVPMLFTGHSLGRDKLEQLLRQGRLSRD
C. plantagineum 2   EGSGAYIIRIPFGPRDKYLRKELLWP---HIQEFVDGALSHIVNMSKALGDQIGGGQPWPYVIHGHYADAGDSAALLSGALNVPMVLTGHSLGRNKLEQLLKQGRQTKE
Vicia faba          ESSGAYIIRIPFGPRNKYIPKEELWP---YIPEFVDGAMGHIIQMSKALGEQIGSGHAWPVAIHGHYADAGDSAALLSGALNVPMIFTGHSLGRDKLEQLLKQGRLSTD
S. tubersom         ESSGAYIIRIPFGPREKYIPKEQLWP---YIQSKVLGEQIGSGYPWPVAIHGHYADAGDSAALLSGALNVPMLFTGHSLGRDKLEQLLAQGRKSKD
Beta vulgaris       ESSGAYIVRIPFGPRDKYIAKEELWP---YIPEFVDGALNHIVQMSKVLGEQIGSGETWPVAIHGHYADAGDSAALLSGGLNVPMLLTGHSLGRDKLEQLLKQGRMSKD
Zea mays            ESSGAYIVRIPCGPRDKYLKKEALWP---YLQEFVDGALAHILNMSKALGEQVGNGRPVLPYVIHGHYADAGDVAALLSGALNVPMVLTGHSLGRNKLEQLLKQGRMSKE
Orysa sativa 1      ESAGAYIVRIPCGPPDKYLRKEALWP---YLQEFVDGALAHILNMSKALGEQVSNGKLVLPYVIHGHYADAGDVAALLSGALNVPMVLTGHSLGRNKLEQIMKQGRMSKE
Orysa sativa 2      REAVRLVRTLCAFRAVQGTSTSVKSPVALPPRVCRSSRAYLNMSKALGEQVSNGKLVLPYVIHGHYADAGDVAALLSGALNVPMVLTGHSLGRNKLEQIMKQGRMSKE
A. thaliana 1       DSCGSYIIRIPCGSRDKYIPKESLWP---HIPEFVDGALNHIVSIARSLGEQVNGGKPIWPYVIHGHYADAGEVAAHLAGALNVPMVLTGHSLGRNKFEQLLQQGRITRE
A. thaliana 2       ENSGAYIIRIPFGPKDKYIAKEHLWP---FIQEFVDGALSHIVRMSKAIGETGRGHPWWPSVIHGHYASAGIAAAILLGALNLPMAFTGHFLGKDKLEGLLKQGRQTRE
S. officinarum      ENSGAYIIRIPFGPKDKYIAKEHLWP---FIQEFVDGALSHIVRMSKAIGETGRGHPWWPSVIHGHYASAGIAAAILLGALNLPMAFTGHFLGKDKLEGLLKQGRQTRE
                     :*   *:** ::  * **.:*        :: ::*   **   : :** : ::  **  :** :*****:   : *   :::: *  ::: ** :***:

374       384       394       404       414       424       434       444       454       468
                     |         |         |         |         |         |         |         |         |         |
Spinach SPS1        EVDATYKIMRRIEAEELCLDASEIVITSTRQEIEEQWQLYHGFDLVLERKLRARMRRGVSCHGREMPRMAKIPPGMEFNHIAPEDADMDTDIDG------HKESNANPDP
Citrus unshiu       EINATYKIMRRIEAEELSLDDASEIVITSTRQEIEEQWRLYDGFDPVLERKLRARIKRNVSCYGKEMPRMAIIPPGMEFHHIVPQDGDMDGETEG-----NEDNPASPDP
C. plantagineum 1   EINSTYKIMRRIEAEELSLDDASEMVITSTRQEIEEQWRLYDGFDPILERKLRARIKRNVSCYGREMPRMVIPPGMEFHHIVPHDGDLDAEPEF-----NEDSKSP-DP
C. plantagineum 2   DINSMYRIMRRIEAEELSLDDAAELVITSTKQEIEEQWGLYDGFDVKLERVLRARARGVNCHGREMPRMAVIPPGMDFSNVVPEDGSEGDG---DLATLTEATSPRSVP
Vicia faba          EINSTYKIMRRIEAEELALDGTEIVITSTRQEIEEQWRLYNGFDPVLERKTRARIRRNVSCYGRYMPRMSVIPPGMEFHHIAPLDGDIETEPEG-----ILDHPAPQDP
S. tubersom         EINSTYKIMRRIEAEELTLDASEIVITSTRQEIEEQWRLYDGFDPILERKLRARIKRNVSCYGREMPRMAVIPPGMEFHHIVPHEGDMDGETEG-----SEDGKTP-DP
Beta vulgaris       DINNTYKIMRRIEAEELSLDASEIVITSTRQEIEEQWHLYDGEFWHLYDGEWRLRARMKRGVSCYGREMPRMVVIPPGMEFNHIVPHEGDMDGETEE-----TEEHPTSPDP
Zea mays            EIDSTYKIMRRIEGEELALDASELVITSTRQEIEEQWGLYDGEWGLYDGFDVKLEVLRARARRGVSCHGREMPRMDFSNVVHEDIPG-DGDVKDDIVGLEGASPKSMP
Orysa sativa 1      EMDSTYKIMRRIEGEELALDAAELVITSTRQEIEEQWGLYDGEFDVKLEKVLRARARRGVSCHGREMPRMVVIPPGMDFSSVVPEDTS--DG---DDGKDFEIASPRSLP
Orysa sativa 2      EIDSTYKIMRRIEGEELALDATEPVITSTRQEIEEQWGLYDGEFDVKLEKVLRARARARGVSCLGRYMPRMVVIPPGMDFSYVLTQDSQEP-DGDLKSLIGPDRNQIKKPVP
A. thaliana 1       DIDRTYKIMRRIEAEEEQSLDAAEMVVTSTRQEIDAQWGLYDGFDIKLERKLVRRRGVSCLGRYMPRMVVIPPGMDFSYVLTQDSQEP-DGDLKSLIGPDRNQIKKPVP
A. thaliana 2       QINMTYKIMCRIEAEELSLDASEIVIASTRQEIEEQWNLYDGFEVIPARLKLRARVKRGANCYGRGMPRMVIIPPGVEFGHII-HDFDMDGEEE----NPSPASEDP
S. officinarum      QINMTYKIMCRIEAEELSLDASEIVIASTRQEIEEQWNLYDGFEVILARKLRARVKRGANCYGRGMPRMVIIPPGVEFGHII-HDFDMDGEEE----NPSPASEDP
                     :   **:**:*** **  :: **.::* :::: ** .*::.* . *  : * * : .:..* ::::.*:****.: :  :*   *

478       488       498       508       518       528       538       548       558       568       578
                     |         |         |         |         |         |         |         |         |         |         |
Spinach SPS1        VIWSEIMRFFSNGRKPMILALARPDPKKNLTTLVKAFGECRPLRELANLTLIIGNRDDIDEMSTTSSSVLISILKLIDKYDLYGQVAYPKHHKQSDVPDIYRLAAKTKGV
Citrus unshiu       PIWSEIMRFFTNPRKPVILALARPDDPKKNITTLVKAFGECRPLRELANLTLIMGNRDDIDEMSSTSASVLLSVLKLLDKYDLYGQVAYPKHHKQSDVPEIYRLAAKTKGV
C. plantagineum 1   HIWTEIMRFFSNPRKPMILALSRPDPKKNITTLVKAFGECKPLRELANLTLIMGNRDNIDEMSGTNASVLLSIIKMIDKYDLYGLVAYPKHHKQSDVPEIYRLAAKTKGV
C. plantagineum 2   AIWADVMRFLTNPHKPMILALSRPDHKKNVTTLVKAFGECRPLRELANLTLIMGNRDDIDEMSGGNASVLTTVLKLIDKYDLYGQVAFPKHHKQSDVPEIYRLASKTKGV
Vicia faba          PIWSEIMRFFSNPRKPVILALARPDPKKNLTTLVKAFGECRPLRELANLTLIMGNRDGIDEMSSTSSSVLLSVVLSVLKLIDKYDLYGQVAYPKHHKQSDVPDIYRLAAKTKGV
S. tubersom         PIWAEIMRFFSPRKPMILALARPDDPKKNLTTLVKAFGECRPLRDLANLTLIIMGNRDNIDEMSSTNSALLLSILKMIDKYDLYGQVAYPKHHKQSDVPDIYRLAAKTKGV
Beta vulgaris       PIWSEIMRFFSKPRKPMILALARPDPKKNITTLVKAFGECRPLRELANLTLIMGNRDGIDEMSSTNSALLLSILKMIDKYDLYGQVAYPKHHKQSDVPDIYRLAAKTKGV
Zea mays            PIWAEVMRFLTNPHKPMILALSRPDPKKNITTLVKAFGECRPLRELANLTLIMGNRDDIDDWSAGNASVLTTVLKLIDQYDLYKLIDKYDLYKLIDKYDLYKGSVAFPKGHHNQADVPEIYRLAAKKGV
Orysa sativa 1      PIWAEVSRFWTNPHKPMILALSRPDPKKNITTLVKAFGECRPLRELANLILSMGTRDDIDGMSAGNASVLTTVLKLIDKYDLYGSVAFPKYHKQSDVPEIYRLTGKMGV
Orysa sativa 2      PIWAEVMRFLTNPHKPMILALSRPDPKGNITTLVKAFGECRPLRELANLTLIMGNRDDIDEMSAGNASVLTTVLKLIDKYDLYGSVAFPKHHKQSDVPEIYRLTGKMGV
A. thaliana 1       PIWSEIMRFFSNPHKPTILALSRPDHKKNVTTLVKAFGECRPLRELANLVLIGNRDDIEEMPNSSSVVLMNVLKLIDQYDLYGQVAYPKHHKQSEVPDIYRLAAKTKGV
A. thaliana 2       PIWSQIMRFFTNPRKPMLAVARPYPEKNITTLVKAFGECRPLRELANLTLIMGNREAISKMHNMSAAVLTSVLTLIDEYDLYGQVAYPKHHKHSEVPDIYRLAARTKGA
S. officinarum      PIWSQIMRFFTNPRKPMLAVARPYPEKNITTLVKAFGECRPLRELANLTLIMGNREAISKMHNMSAAVLTSVLTLIDEYDLYGQVAYPKHHKHSEVPDIYRLAARTKGA
                     ***::  :*  ** ****:: :   :  ********:**:******* :  .:     :: .:   :.::   :: *:::*****.***** :**** *:
```

SPINACH SPS1 VS SYNECHOCYSTIS

```
                 10         20         30         40         50         60         70         80         90        100        110
                  |          |          |          |          |          |          |          |          |          |          |
Spinach SPS1    MAGNDWINSYLEAILLDVGGQGIDASTGKTSTAPPSLLLRERGHFSPSRYFVEEVISGFDETDLHRSWVRAASTRSPQERNTRLENLCWRIWNLARKKQIEGEEAQRLAK
Synechocystis 120        130        140        150        160        170        180        190        200        210        220
                  |          |          |          |          |          |          |          |          |          |          |
Spinach SPS1    RHVERERGRREATADWSEDLSEGERGDTVADMLFASESTKGRMRRISSVEMMDNWANTFKEKKLYVVLISLHGLIRGENMELGRDSDTGGGQVKYVVELARALGSMPGVYR
Synechocystis                                                     MSYSSK--YILLISVHGLIRGENLELGRDADTGGQTKYVLELARALVKNPQVAR
                                                                  :::..*  *::::***:**********:*:::***:****** .***:******

230        240        250        260        270        280        290        300        310        320        330
                  |          |          |          |          |          |          |          |          |          |          |
Spinach SPS1    VDLLTRQVSAPGVDWSYGEPTEMLSSRNSENSTEQLGESSGAYIRIPFGPKDKYVAKELLWPYIPEFVDGALSHIKQMSKVLGEQIGGGLPVWPASVHGHYADAGDSAA
Synechocystis   VDLLTRLIKDPKVDADYAQPRELIGDR------------------AQIVRIECGPE-EYIAKEMLWDYLDNFADHALDYLK-------EQ-----PELPDVIHSHYADAGYVGT
                ******:: .*: ** .*.:* *::::.*                 * .:*:* **:  *:.*****:*:***.*:****.             *:   *:* *******.:

340        350        360        370        380        390        400        410        420        430        440
                  |          |          |          |          |          |          |          |          |          |          |
Spinach SPS1    LLSGALNVPMVFTGHSLGRDKLDQLLKQGRLSREEVDATYKIMRRIEAEELCLDASEIVITSTRQEIEEQWQLYHGFDLVLERKLRARMRRGVSCHGREMPRAKIPPGM
Synechocystis   RLSHQLGIPLVHTGHSLGRSKRTRLLLSG--IKADEIESRYNMARRINAEEETLGSAARVITSTHQEIAEQYAQY---DYYQP-----------------DQMLVIPPGT
                 ** *:* *:*.******.*: :**:*.   :* :*:: :*::*****.:*: ******:***.*: **  .*   *                    :*  *.****:

450        460        470        480        490        500        510        520        530        540        550
                  |          |          |          |          |          |          |          |          |          |          |
Spinach SPS1    EENHLAPEDADMDTDIDGHKESNANPDPVIWSEIMRFFSNGRKPMILALARPDKNGNLTTLVKAFGECRPLRELANLTLIIGNRDDIDEMSTTSSSVLISILKLIDKYDL
Synechocystis   DLEKFYPP-----------KG----NEWETPIVQ-ELQRFLRHPRKPILLALSRPDPRKNIHKLIAAYGQSPQLQAQANLVIVAGNRDDITDLDQGPREVLTDLLLTIDRYDL
                :::::*             *.    ***:**.: *:* *: *.:**:* ***:**.*:* .:** *** *:*: *: ***..:*.*****.::   **::***::*:****

560        570        580        590        600        610        620        630        640        650        659
                  |          |          |          |          |          |          |          |          |          |          |
Spinach SPS1    YGQVAYPKHHKQSDVPDIYRLAAKTKGVFINPAFIEPFGLTLIEAAAYGLPIVATGNGGPVDIIGVLNGLLIDPHDQKSIADALLKLVADKGHLWTKCRQNGLKNIH-LF
Synechocystis   YGKVAYPKQNQAEDVYALFRLTALSQGVFINPALTEPFGLTLIEAAACGVPIVATEDGSVPYLINPLDEVDIADKLLKVLNDKQONQFLSESGLEGVKRHY
                **:****: :. :* * :*:*:*:.****** : *:****** * :.:* .:*:**.::: *::*.: ****  :::*:**:**.: :*:** :. *: ..:

669        679        689        699        709        719        729        739        749        759        769
                  |          |          |          |          |          |          |          |          |          |          |
Spinach SPS1    SWPEHCKNYLSRIASCKPRQPNMQRIDEGGSENSDTDSAGDSLRDIQDISINLKLSLDAERTEGGNSFDDSLSEEANAKRKIENAVAKLSKSMDKAQVDVGNLKFPAIRR
Synechocystis   SWPSHVESYLEAINALTQQTSVLKRSD-------LK----RR---RTLYYN--------------G--ALVTSLD------------QNLLGAL-----QG---G----LPGDRQ
                ***.*.:.**.:*.: . ::*:*.**        *     **   *::*:                 * :*:**            :* :*:       **   *    ********:

779        789        799        809        819        829        839        849        859        869        879
                  |          |          |          |          |          |          |          |          |          |          |
Spinach SPS1    RKCIFVIALDCDVTSDLLQVTKTVISIVGEQRPTGSIGFILSTSMTLSEVDSLLDSSGLRPADFDAFICNSGSELYPSTDYSESPEVLDQDYSHIDYRMGGEGLMKTL
Synechocystis   ----TLD---ELLEVLY-----QHRKN--VGFCIATGRRLDSVLKILR--EYRIPQPDMLTSMGTEIYS--SPDL--IP---DQSMRNHIDYLMN----RNAI
                    :**   :**:**:      :** *  **:::** *:*: **:      *: * *  :**.* *:*  ***:  *    :.*.::****:*     ..:
```

FIG. 4A

```
                  889       898       908       918       928       938       948       958       968       978       988
                   -         -         -         -         -         -         -         -         -         -         -
Spinach SPS1     VKWAASVNEKKGEN-APNIVIADETSSTTHCYAFKVNDFTLAPPAKELRKMRIQALRCHAIYCQNGTRLNVIPVLASRSQALRYLFMRWGVELSNFVVFVGESGDTDYE
Synechocystis    VR---ILGELPGLALQP---KEELSAYKISYFY---DAAIAPNLEEIRQLLHKGEQTVNTIIS-FQQFLDILPIRASKGYAVRMLSQQWNIPLEH-VFTAGGSG-AD-E
                  *:   .:* :*   *: :**. *.:   *: ::**    :  ::** :* *::::                :*: . *  *::::: **:. ** :***..: .:. **

998      1008      1018      1027      1037      1047
                   -         -         -         -         -         -
Spinach SPS1     GLLGGVHKTVILKGIGSNTSNFHATRAYPMEHVMPVD-SPNMFQTGGCNIDDISDALSKIGCLKAQKSL              (SEQ. ID. No. 1)
Synechocystis    DMMRGNTLSVVVA-------NRHHEELSNLGEIEPIYFSEKRYAAG------ILDGLAHYRFFELLDPV              (SEQ. ID. No. 14)
                  :: *  :*::*:       ** .  :  ::  :: *::**.        ::** ::: **::: ::

Alignment data :
Alignment length : 1059
Identity (*) : 309 is 29.18 %
Strongly similar (:) : 159 is 15.01 %
Weakly similar (.) : 65 is 6.14 %
Different : 526 is 49.67 %
Sequence 0001 : Spinach ( 1056 residues).
Sequence 0002 : Synechocystis ( 720 residues).

CLUSTALW options used :
    endgaps=1
    gapdist=8
    gapext=0.05
    gapopen=10.0
    hgapresidues=GPSNDQERK
    matrix=blosum
    maxdiv=40
    outorder=input
    pwgapext=0.1
    pwgapopen=10.0
    pwmatrix=blosum
    type=PROTEIN
```

*FIG. 4B*

TRANSGENIC COTTON PLANTS WITH ALTERED FIBER CHARACTERISTICS TRANSFORMED WITH A SUCROSE PHOSPHATE SYNTHASE NUCLEIC ACID

FIELD OF THE INVENTION

The present invention relates to a method for increasing the yield or quality of product from a plant by altering the expression of sucrose phosphate synthase. In particular, the present invention provides a transgenic cotton plant that has an increased level of sucrose phosphate synthetase relative to a non-transgenic cotton plant. Methods are also provided for increasing the yield or the quality of cotton fiber and the yield of cotton seed produced from a cotton plant. General methods are provided for regulating the thickness of cell walls, for increasing the yield and quality of other plant fibers, for regulating the ratio of cellulose to other dry weight components of the plant, for increasing seed yield, and for increasing tolerance of photosynthetic efficiency to cool night temperatures.

BACKGROUND OF THE INVENTION

The control of high-rate cellulose production and its regulation by temperature are critical to agriculture, since all plant growth (and hence the production of all food crops) depends on cellulose synthesis to build cell walls throughout the vegetative and reproductive parts of the plant. The cellulose within the primary walls of all cells of the plant body is also of direct industrial importance as a digestible part of animal forage and for manufacture of thickeners, ethanol, and other cellulose-based or cellulose-derived products. Furthermore, plant parts based on secondary cell walls with high cellulose content are contained in or compose economically important plant products, including cotton fibers, wood, and fibers in forage crops. The agronomic productivity and product quality of wood and cotton, as well as other fiber crops such as hemp and flax, are in large part determined by the biosynthesis of cellulose. Therefore, an understanding of the basic regulatory mechanisms of cellulose synthesis and how it responds to temperature stress allows for beneficial changes in crop plants (improved product yield and quality) through genetic engineering.

Since cotton fiber weight is more than 90% cellulose, cotton is one particular crop where enhancing the flow of carbon to cellulose production can increase yield and quality. This will be an especially beneficial outcome if it is achievable under diverse environmental conditions encountered in cotton production fields, including cool night temperatures that hinder cotton fiber development. For example, it is known that cool night temperatures hinder the seasonal yield and quality of cotton fiber (Gipson, "Temperature Effects on Growth, Development, and Fiber Properties," in Mauney, eds., *Cotton Physiology*, The Cotton Foundation:Memphis, pp. 47–56) because they hinder the rate of cellulose synthesis (Roberts et al., "Effects of Cycling Temperatures on Fiber Metabolism in Cultured Cotton Ovules," *Plant Physiol.*, 100:979–986 (1992)). The ability to manipulate cotton yield and fiber quality parameters and sustain or improve them under diverse and/or stressful environmental conditions will allow for beneficial changes in crop plants (improved product quality) through genetic engineering.

Cotton fiber yield is the most important determinant of the value of the crop to the producer. Reputable cotton breeders have recently pointed out that cotton production has reached a fiber yield plateau, which bodes ill for the financial success of producers given escalating costs. Potential contributors to this problem include the environmental sensitivity of cotton fiber and seed development, the narrow genetic base of commercial cotton, and the recent introduction of transgenic traits such as herbicide and insect resistance through back-crossing with transformed *Gossypium hirsutum* cv. Coker 312. Coker 312 (C312) is an old cultivar frequently used for transformation because of its high regeneration capacity. Use of genetic engineering to make cotton crop production more stress resistant, to expand the genetic potential of cultivated cotton, and to improve the yield of transformed cotton with diverse novel traits will bring needed increases in crop yield.

Similarly, seed yield is of value to the cotton producer since seeds are sold for oil production and animal feed. Another minor component, the short fuzz fibers on each seed, provides added economic value to the seed crop. Increased seed and fuzz fiber yield without sacrifice of lint fiber yield or quality would help the producer recover more profit per acre of cotton production. As for cotton seed, increased yield of any seed crop will be of major benefit to agriculture.

Improved cotton fiber quality parameters such as micronaire, maturity ratio, length, length uniformity, bundle strength, and single fiber strength are desired by the textile industry to produce increasingly high quality products and to take full advantage of modern spinning technologies. Fiber quality parameters should also be high enough for the cotton producer to avoid price discounts when he sells his crop to the gin. For example, in a short growing season on the Texas Southern High Plains, producers often suffer price discounts due to low micronaire. Increasingly high fiber quality achieved through breeding has become a required standard in the cotton industry, and market forces may change so producers are more routinely rewarded with price premiums for higher quality cotton. Therefore, stabilizing or increasing fiber quality under diverse environmental conditions through genetic engineering will increase the profitablity of cotton crop production and provide a new spectrum of material properties for exploitation by the processing industries.

Other plant fibers, although often of different tissue origin, share structural features in common with cotton fibers in being elongated cells with cellulose-rich walls. Like cotton fibers, other plant fibers of industrial use are required to have high quality as defined by factors such as cellulose content and wall thickness, diameter, fineness (or coarseness), length, strength, durability, uniformity, elasticity, and elongation. There is an optimum range of such parameters for each particular fiber source and industrial use. Taking examples from wood fibers used after pulping in paper production, longer fiber length and higher single fiber elongation both promote higher paper tear strength. In addition, thick fiber walls promote high pulp yield and production of absorbent paper with high tearing resistance. However, thinner fiber walls promote fiber collapse and better inter-fiber bonding that aids production of high quality writing paper. Therefore, there exists a need to control cell wall thickness and other fiber quality parameters in either negative or positive directions in diverse fibers to improve their yield or quality or expand the range of their industrial utility.

Maximizing crop productivity and utility per acre is a key component of sustainable agriculture. Enhanced production of multiple products from the same crop, such as seed and fiber, would be useful. Similarly, it will be an advantage to maximize the possibility of a successful crop harvest, for example by generating plants with stiffer stems that can better resist lodging in the field without sacrificing the yield of a seed crop.

An increasing level of $CO_2$ in the atmosphere is a concern due to predicted association of rising global temperatures. There exists a need for plants that are better able to immobilize $CO_2$ by conversion of it into useful products, especially products that are typically not burned to regenerate $CO_2$.

Cotton leaves assimilate most carbon into starch during the day, and the starch is converted to sucrose at night for translocation to sinks. As just described, cotton fibers are not well adapted to use this sucrose efficiently for cellulose synthesis during cool nights. Therefore, cool nights reduce cotton photosynthetic efficiency during the following warm day (Warner et al., "Response of Carbon Metabolism to Night Temperatures in Cotton," Agron. J., 87:1193–1197 (1995)), possibly due to hindered use of carbohydrate at night. The resulting leaf carbohydrate accumulation could signal a down-regulation of photosynthetic genes. The excess starch remaining in the leaf after a cool night could be involved in some negative feedback mechanism reducing photosynthetic rates even after re-warming. There is a need to use genetic engineering to alleviate the cool-night-associated inhibition of photosynthesis during the following warm day.

Sucrose phosphate synthase ("SPS") is a key protein involved in carbon metabolism in plants (See FIG. 1). SPS catalyzes the formation of sucrose phosphate from UDP-glucose and fructose 6-phosphate. In the leaf, SPS is important in controlling the partitioning of reduced carbon between starch and translocatable sucrose (Huber et al., "Role and Regulation of Sucrose-Phosphate Synthase in Higher Plants," Annu. Rev. Plant Physiol. Plant Mol. Biol., 47:431–44 (1996)). In growing sink cells, the data in this invention demonstrate that SPS is involved in directing the flow of carbon to cellulose. Its level of activity can regulate the amount of metabolic flux directed toward cellulose synthesis compared to respiration (See FIG. 2). According to this model, SPS within cellulose-storing sink cells can increase sink strength through an enhanced rate of cellulose synthesis by promoting sucrose synthesis in one or both of two cases: (a) if sucrose transported from the leaves is cleaved to release glucose and fructose before or after entering the sink cells; and/or (b) to reuse the fructose released by the activity of sucrose synthase to channel UDP-glucose and fructose to cellulose synthase. A decreased level of SPS activity can decrease sink strength, by analogous mechanisms, in any case where sink filling is affected by sucrose levels.

In tomato, over-expression of SPS has been shown sometimes to cause a 32% increase in total fruit dry weight. This increase was due not to an increase in individual fruit weight, but to a 50% increase in fruit number (Micallef et al., "Altered Photosynthesis, Flowering, and Fruiting in Transgenic Tomato Plants That Have an Increased Capacity for Sucrose Synthesis," Planta, 196:327–334 (1995)). These tomato plants have also sometimes been shown to have increased fresh fruit weight per fruit and increased fruit soluble solids (sugars) (Laporte et al., "Sucrose-Phosphate Synthase Activity and Yield Analysis of Tomato Plants Transformed with Maize Sucrose-Phosphate Synthase," Planta, 203:253–259 (1997)). These reports provide no information about seed yield since tomato seeds weigh little compared to tomato fruits and seeds were not separated from fruits for weighing.

It should be noted that although cotton bolls and tomatoes are both classified botanically as fruits, the nature of the fruits and the relative importance of the seeds they contain is very different. Tomato fruits are essentially sacks of primary cell walls filled with water and soluble glucose, fructose, and sucrose as storage carbohydrates. These sugars crystallize upon drying, contributing to fruit dry weight. Within the fruit, tomato seeds are not a significant sink due to their small size, and they have no economic value except for propagation of tomato. The fruit is the major sink in tomatoes; it constitutes almost all of tomato yield and is the only tomato part with significant economic value.

In contrast, the cotton fruit is relatively dry and thin-walled. The fruit itself does not constitute any substantial sink in cotton or contribute to cotton yield. It protects the seeds only until boll opening, after which it withers. The fruit has no or little economic value (as compost). Cotton seeds with attached fiber represent the two major sinks of substantial economic value in the cotton crop. The cotton fiber is an elongated epidermal cell of the cotton seed coat; it is defined botanically as a trichome. Therefore, the two major sinks in seeds are: (1) the cotyledons of the seed embryo that store oil and protein; and (2) the secondary cell walls of the seed epidermal trichomes (cotton fibers) that store insoluble cellulose. Soluble sugars are not stored in any significant quantity in a mature cotton seed or fruit. Cotton seeds with their attached fiber represent all of the yield in the cotton crop. Therefore, cotton, as well as other fiber producing plants, differ significantly from tomato.

Increased total dry weight of vegetative parts of plants over-expressing SPS has been shown in tomato leaves. In the same study, no change was observed in dry weight of stems and root dry weight decreased (Galtier et al., "Effects of Elevated Sucrose-Phosphate Synthase Activity on Photosynthesis, Assimilate Partitioning, and Growth in Tomato (Lycopersicon esculentum var UC82B)," Plant Physiol., 101:535–543 (1993)). Tomato leaves do not contain substantial fiber, being composed mainly of mesophyll cells and conducting vascular tissue. The same plants were shown to sometimes have increased dry weight on a whole-plant basis (Ferrario-Méry et al., "Manipulation of the Pathways of Sucrose Biosynthesis and Nitrogen Assimilation in Transformed Plants to Improve Photosynthesis and Productivity," in Foyer, eds., A Molecular Approach to Primary Metabolism in Higher Plants, Taylor and Francis-:New York, pp. 125–153 (1997)) and in above-ground parts including leaves plus stems (Laporte et al., "Sucrose-Phosphate Synthase Activity and Yield Analysis of Tomato Plants Transformed with Maize Sucrose-Phosphate Synthase," Planta, 203.253–259 (1997)). In potatoes over-expressing SPS, increased total dry weight of tubers has been shown (Shewmaker, "Modification of Soluble Solids Using Sucrose Phosphate Synthase Encoding Sequences," PCT International Publication Number WO 97/15678). Potato tubers do not contain substantial fiber. They are composed mainly of parenchyma cells with primary walls that store abundant starch and lesser amounts of protein. The major yield component of potato tubers is starch. All of these reports lack information on the effect of SPS over-expression on cell wall thickness, cellulose content, and fiber and seed yield of plants. However, the absence of demonstrated increase in stem weight argues against increased fiber content in the tomato plants analyzed.

Increased expression of SPS has been shown to exert other beneficial effects in tomato and Arabidopsis. In both species, leaf starch storage is reduced in preference for synthesis of sucrose. In both species, maximal rates of photosynthesis are enhanced, most significantly in elevated $CO_2$ and saturating light (Galtier et al., "Effects of Light and Atmospheric Carbon Dioxide Enrichment on Photosynthesis and Carbon Partitioning in the Leaves of Tomato (*Lycopersicon esculentum* L.) Plant Over-Expressing Sucrose Phosphate Synthase," *J. Expt. Bot.*, 46:1335–1344 (1995); Micallef et al., "Altered Photosynthesis, Flowering, and Fruiting in Transgenic Tomato Plants That Have an Increased Capacity for Sucrose Synthesis," *Planta*, 196:327–334 (1995); and Signora et al., "Over-Expression of Sucrose Phosphate Synthase in *Arabidopsis thaliana* Results in Increased Foliar Carbohydrate Accumulation in Plants After Prolonged Growth with $CO_2$ Enrichment," *J. Expt. Bot.*, 49:669–680 (1998)). However, these reports provide no information related to effects of cool nights on photosynthesis during the warm day.

Thus, there exists a need for a method to control the level of synthesis of cellulose in fiber producing plants, in particular cotton. There exists a need to be able to control the yield and quality of fibers of commercial value, in particular cotton, under diverse environmental conditions. A general need exists to be able to control the synthesis of cellulose and the thickness of cell walls in plants. A general need exists to promote photosynthetic efficiency in plants growing under cool night temperatures. It is important to be able to increase seed yield in crops as well. The present invention addresses those needs and provides improved plants.

SUMMARY OF THE INVENTION

The present invention generally relates to a method of controlling the cellulose synthesis in plants to optimize the level of production and quality of the products derived from the plants.

The invention includes the regulation in the cellulose content, thickness, or yield of any plant cell wall of agricultural or industrial use. Such cell walls include typical thin primary cell walls such as those that are digested in forage and those that exist in useful agricultural residues, for example beet root parenchyma cells remaining after sugar extraction that can be converted into thickening agents. Such cell walls include thick walls such as those of collenchyma and xylem parenchyma that can aid plant rigidity or contribute to yield and digestibility of forage or other agricultural products. Such cell walls also include secondary cell walls such as are commonly found in fiber.

In particular, the present invention provides a transgenic cotton plant that has an increased level of sucrose phosphate synthetase relative to a non-transgenic cotton plant.

The invention also provides a method of increasing the yield of a cotton plant by introducing into the cotton plant a chimeric DNA construct that alters the level of sucrose phosphate synthase activity in an amount sufficient to increase the seed and fiber yield of the cotton plant.

The present invention can also be used to increase the quality of cotton fiber produced from a cotton plant by introducing into a cotton plant a chimeric DNA construct that alters the level of sucrose phosphate synthase activity in an amount sufficient to increase the quality of the cotton fiber produced by the cotton plant.

The invention includes a method of increasing tolerance of photosynthetic efficiency to cool night temperatures by introducing into a plant a chimeric DNA that alters the sucrose phosphate synthase activity in an amount sufficient to increase tolerance of photosynthetic efficiency to cool night temperatures.

In yet another embodiment, the invention provides a method of regulating the ratio of cellulose to other dry weight components of the plant by introducing into a plant a chimeric DNA construct capable of altering sucrose phosphate synthase activity in an amount sufficient to regulate the ratio of cellulose to other dry weight components of the plant.

The invention also provides a method of regulating the thickness of cell walls in a plant by introducing into a plant a chimeric DNA construct that alters sucrose phosphate synthase activity in an amount sufficient to regulate the thickness of cell walls.

In yet another embodiment, the invention provides a method of increasing the harvestable yield of fiber from a fiber containing plant by introducing into a plant a chimeric DNA construct that alters sucrose phosphate synthase activity in an amount sufficient to increase the harvestable yield of fiber from a fiber producing plant.

In yet another embodiment, the invention provides a method of increasing the harvestable yield of seed from a seed producing plant by introducing into a plant a chimeric DNA construct that alters sucrose phosphate synthase activity in an amount sufficient to increase the harvestable yield of seed from a seed producing plant.

In yet another embodiment, the invention provides a method of improving the quality of fiber from a fiber producing plant by introducing into a plant a chimeric DNA construct that alters sucrose phosphate synthase activity in an amount sufficient to regulate fiber quality. Such improvement may be exemplified by changes in length, strength, and weight per unit length.

BRIEF DESCRIPTION OF THE DRAWINGS

Figure 3C:
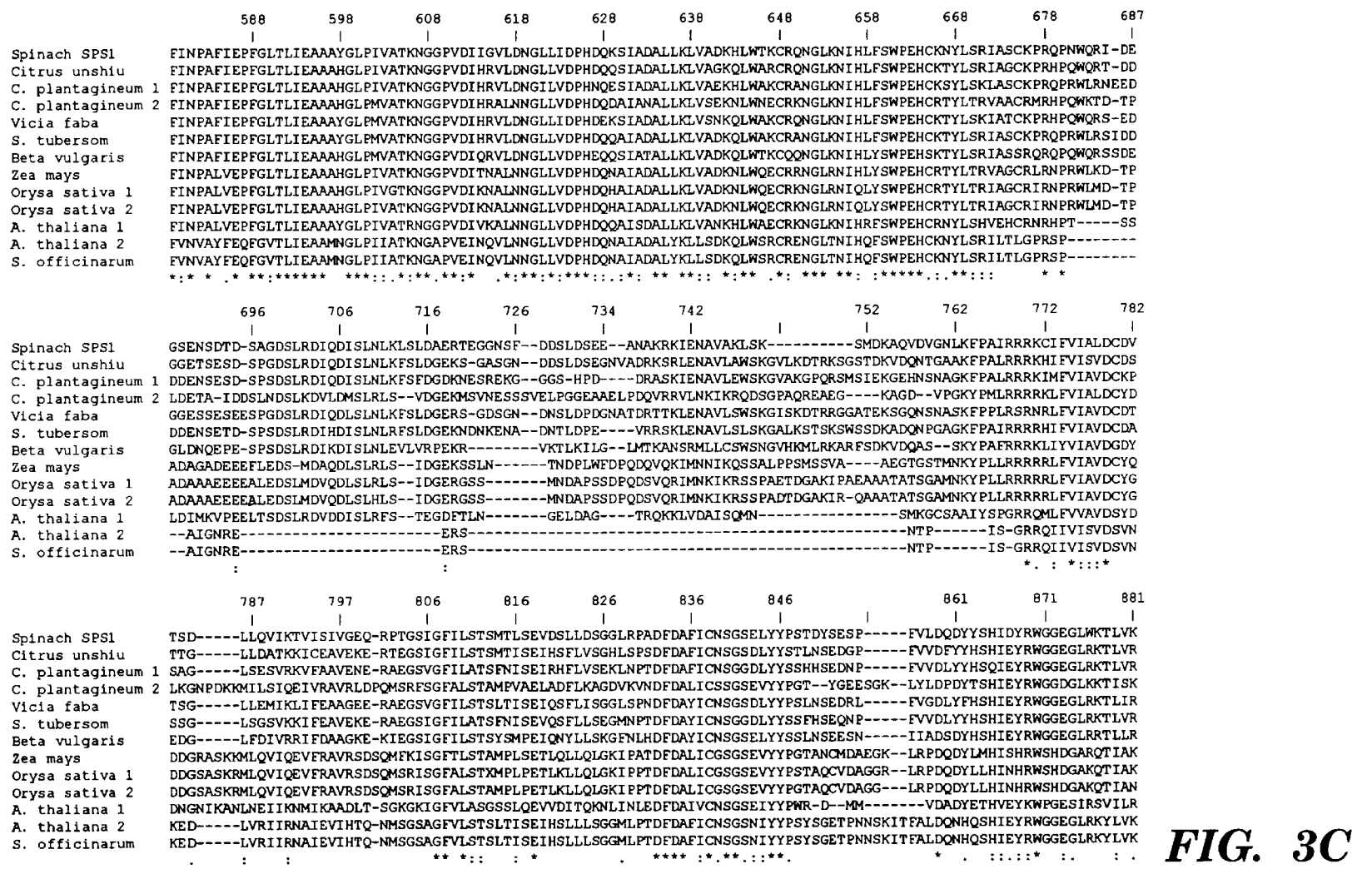
Figure 3D:
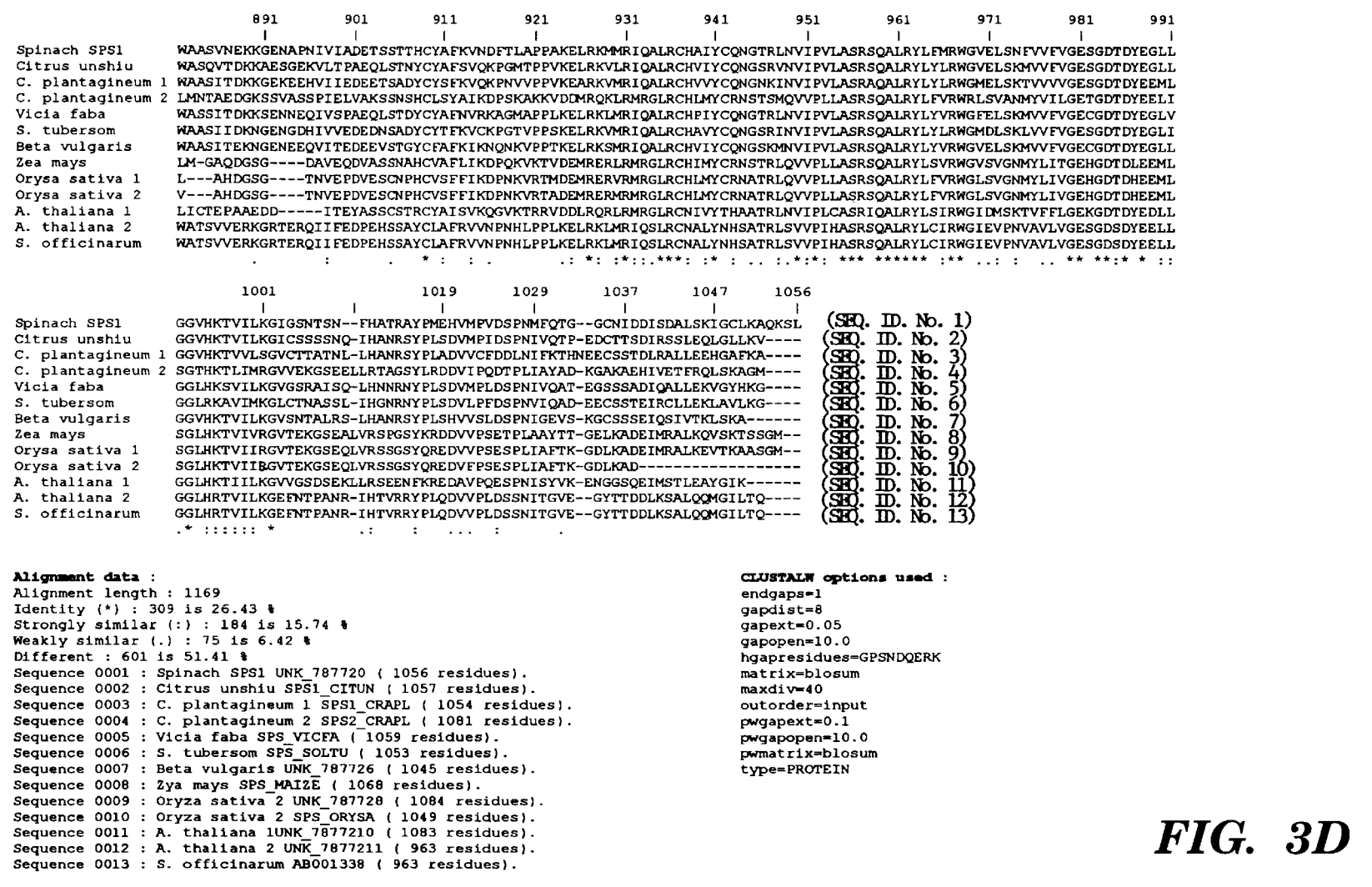

FIGS. 3A–3D show the amino acid alignment between SPS gene sequences from a number of plant species.

FIGS. 4A–4B show the amino acid alignment between the spinach leaf SPS gene sequence and a homologous sequence from Synechocystis.

DETAILED DESCRIPTION OF THE INVENTION

Figure 1:
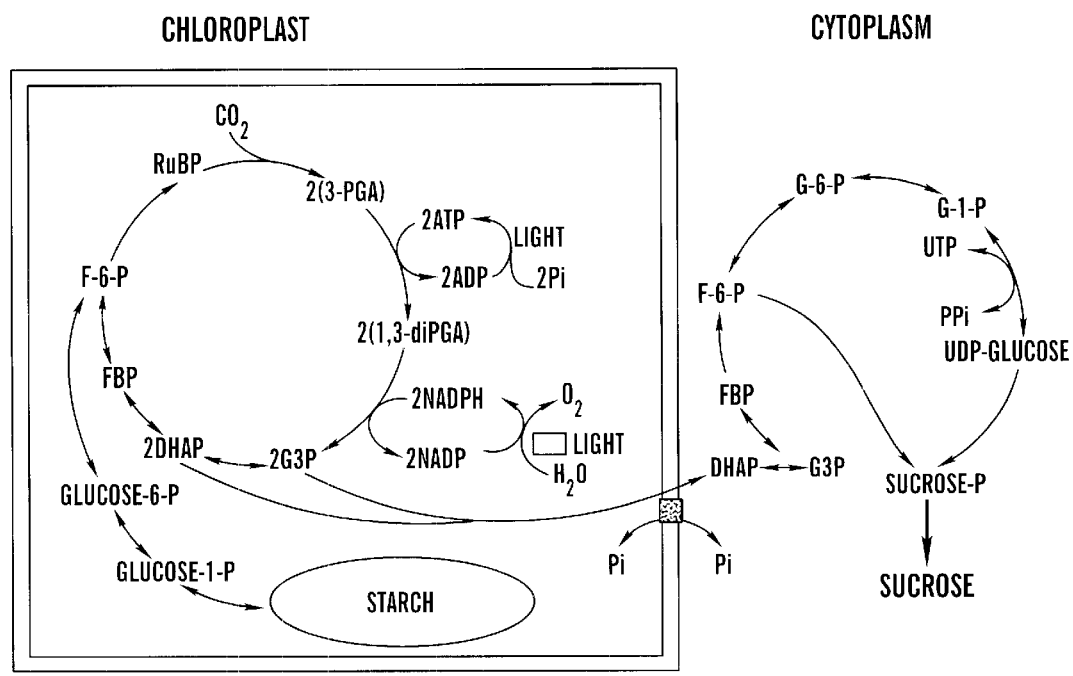
FIG. 1 shows the pathways of carbon assimilation, starch synthesis and catabolism, and sucrose synthesis. UDP-glucose pyrophosphorylase catalyzes the highly reversible reaction between glucose 1-phosphate (G-1-P) and UDP-glucose. Sucrose-phosphate synthase catalyzes the formation of sucrose-phosphate from UDP-glucose and fructose 6-phosphate.

The present invention relates to a method of controlling the cellulose synthesis in plants to optimize the level of production and quality of the products, in particular fiber, derived from the plants.

The word "fiber" is often used to unify a diverse group of plant cell types that share in common the features of having an elongated shape and abundant cellulose in thick cell walls, usually, but not always, described as secondary walls. Such walls may or may not be lignified, and the protoplast of such cells may or may not remain alive at maturity. Such fibers have many industrial uses, for example in lumber and manufactured wood products, paper, textiles, sacking and boxing material, cordage, brushes and brooms, filling and stuffing, caulking, reinforcement of other materials, and manufacture of cellulose derivatives. In some industries, the term "fiber" is usually inclusive of thick-walled conducting cells such as vessels and tracheids and to fibrillar aggregates of many individual fiber cells. Here the term "fiber" is used in its most inclusive sense, for example including: (a) thick-walled conducting and non-conducting cells of the xylem; (b) fibers of extraxylary origin, including those from phloem, bark, ground tissue, and epidermis; and (c) fibers from stems, leaves, roots, seeds, and flowers or inflorescences (such as those of *Sorghum vulgare* used in the manufacture of brushes and brooms). In addition to wood from trees, cotton, and forage crops, the invention is applicable to all fibers, including, but not exclusively, those in agricultural residues such as corn, sugar cane, and rice stems that can be used in pulping, flax, hemp, ramie, jute, kenaf, kapok, coir, bamboo, spanish moss, abaca, and Agave spp. (e.g. sisal).

In a preferred embodiment, the invention provides a transgenic cotton plant wherein the transgenic cotton plant has an increased level of sucrose phosphate synthetase relative to a non-transgenic cotton plant. Table I shows the level of SPS activity from untransformed C312 plants and four transformed plant lines. All transformed plant lines show significant increases in SPS activity in both leaves and fiber.

Sucrose phosphate synthase plays a key role in the metabolic flux of carbon within plant cells. Genes encoding sucrose phosphate synthase have been isolated and sequenced from a number of plant species. [*Spinacia oleracea*: Salvucci et al., *Plant Physiol.*, 102:529–536 (1993);

Sonnewald et al., *Planta*, 189(2):174–181 (1993); *Oryza sativa*: Valdez-Alarcon et al., *Gene*, 170(2):217–222 (1996); *Craterostigma plantaqineum*: Ingram et al., *Plant Physiol.*, 115(1):113–121 (1997); *Viciua faba*: Heim et al., *Gene*, 178(1–2):201–203 (1996); *Solanum tuberosum*: EMBL Accession No. X73477; *Citrus unshiu*: Akira et al., *Mol. Gen. Genet.*, 252:346–351 (1996); *Saccharum officinarum*: Sugiharto et al., *Plant Cell Physiol.* 38:961–965 (1997); *Beta vulgaris*: Hesse et al., *Mol. Gen. Genet.*, 247(4):515–520 (1995); *Zea mays*: Worrell et al., *Plant Cell*, 3:1121–1130 (1991); *Arabidopsis thaliana*, Bevan et al., NCBI Accession No. AL049487; *Synechocystis sp.*: Kaneko et al., *DNA Res.*, 2(4): 153–166 (1995); Kaneko et al., *DNA Res.*, 3(3):109–136 (1996); and unknown organism: Van Assche et al., U.S. Pat. No. 5,665,892-A, which are hereby incorporated by reference.] A comparison of several of the available SPS gene sequences from higher plants is provided in FIGS. 3A–3D. A comparison of a Synechocystis SPS (Kaneko et al., *DNA Res.*, 2(4):153–166 (1995), which is hereby incorporated by reference) with the spinach SPS is provided in FIGS. 4A–4B; this protein from a cyanobacterium has as strong a homology with spinach SPS as all the higher plant proteins have among themselves. Preferred sucrose phosphate synthase genes include the genes isolated from spinach, Arabidopsis, beet, bean, citrus, maize, moss, potato, rice, sugar cane, and Synechocystis. The most preferred sucrose phosphate synthetase is spinach sucrose phosphate synthetase.

In addition to the known sequences of sucrose phosphate synthase, modifications of the known sequences are also within the scope of the invention. Variations in the sequence including substitutions, insertions and deletions may be made to the known sequences of sucrose phosphate synthase. Comparisons of all the available sequences indicate which amino acids are highly conserved and those that are variable. Using that information, it is possible to choose variations that should still produce functional proteins.

The maximum activity of sucrose phosphate-synthase may be determined calorimetrically according to the formation of sucrose-6-P (+sucrose) from fructose-6-P and UDP-glucose by the method as described in (Copeland, "Enzymes of Sucrose Metabolism," *Methods in Plant Biochemistry*, 3:73–83 (1990), which is hereby incorporated by reference). Frozen leaf or fiber tissue was pulverized under liquid nitrogen, then ground in 50 mM HEPES (pH 7.4), 10 mM MgCl2, 1 mM EDTA, 1 mM EGTA, 10% glycerol, and 0.1% Triton-X-100. A 28 µl aliquot of each supernatant was used in each SPS assay, and each extract was tested in triplicate. A 70 µl assay mixture contained 50 mM HEPES (pH 7.4), 10 mM UDPG, 6 mM fructose-6-P, 20 mM glucose-6-P (an SPS activator), 10 mM MgCl2, 1 mM EDTA, 0.40 mM EGTA, 4.0% glycerol, and 0.04% Triton-X-100. The assay was conducted for 10 min at 32–34° C. (on the plateau of maximal activity) then terminated by addition of 70 µl of 1N NaOH. Unreacted hexoses or hexose phosphates were destroyed by immersion of tubes in a boiling water bath for 10 min. After cooling to room temperature, 250 µl of 0.1% resorcinol in ethanol and 750 µl of concentrated HCl were added, followed by incubation for 8 min at 80° C. The tubes were quickly cooled to room temperature, $A_{520\ nm}$ was measured in a spectrophotometer, and sucrose levels in plant extracts were determined in reference to a sucrose standard curve. Triplicate controls were made for each extract to normalize for possible different endogenous levels of sucrose in each extract. For controls, NaOH was added to the assay tube before the plant extract was added; then these tubes were processed in parallel as above except for the step of assay termination by NaOH that was already done. Plant extracts were also analyzed for protein content by Bradford protein assay and leaf extracts were analyzed for chlorophyll content by its absorbance to allow comparison of SPS activities between different samples. Alternatively, the activity of sucrose phosphate-synthase may be determined spectrophotometrically according to liberation of uridine-5'-diphosphate detected by a pyruvate-kinase coupling enzyme reaction as also described in (Copeland, "Enzymes of Sucrose Metabolism," *Methods in Plant Biochemistry*, 3:73–83 (1990), which is hereby incorporated by reference).

In order to express the sucrose phosphate synthase in plants, transgenic plants carrying the gene encoding a sucrose phosphate synthase are produced by transforming a plant with a chimeric DNA construct that expresses sucrose phosphate synthase.

In order to express the sucrose phosphate synthase gene from the chimeric DNA, the construct should include a plant specific promoter. The promoter should ensure that the foreign gene is expressed in the plant. The promoter can be chosen so that the expression occurs only in specified tissues, at a determined time point in the plant's development or at a time point determined by outside influences. The promoter can be homologous or heterologous to the plant. Suitable promoters include e.g. the RUBISCO small subunit promoter, fiber-specific promoters, the promoter of the 35S RNA of the cauliflower mosaic virus described in U.S. Pat. No. 5,034,322 (which is hereby incorporated by reference), the enhanced 35S promoter described in U.S. Pat. No. 5,106,739 (which is hereby incorporated by reference), the dual S35 promoter, the FMV promoter from figwort mosaic virus that is described in U.S. Pat. No. 5,378,619 (which is hereby incorporated by reference), the RI T-DNA promoter described in U.S. Pat. No. 5,466,792 (which is hereby incorporated by reference), the octopine T-DNA promoter described in U.S. Pat. No. 5,428,147 (which is hereby incorporated by reference), the alcohol dehydrogenase 1 promoter (Callis et al., *Genes Dev.*, 1(10):1183–1200 (1987), which is hereby incorporated by reference), the patatin promoter B33 (Rocha-Sosa et al., *EMBO J.*, 8:23–29 (1989), which is hereby incorporated by reference), the E8 promoter (Deikman et al., *EMBO J.*, 7(11):3315–3320 (1988), which is hereby incorporated by reference), the beta-conglycin promoter (Tierney et al., *Planta*, 172:356–363 (1987), which is hereby incorporated by reference), the acid chitinase promoter (Samac et al., *Plant Physiol.*, 93:907–914 (1990), which is hereby incorporated by reference), the Arabidopsis histone H4 promoter described in U.S. Pat. No. 5,491,288 (which is hereby incorporated by reference), or the recombinant promoter for expression of genes in monocots described in U.S. Pat. No. 5,290,924 (which is hereby incorporated by reference).

Preferred promoters include the RUBISCO small subunit promoter, the 35S promoters, fiber enhanced promoters, vascular cell enhanced promoters, stem cell enhanced promoters, or seed enhanced promoters. Such promoters may ensure expression in a tissue specific or tissue-enhanced manner, but may allow expression in other cell types. For example it may ensure enhanced expression in photosynthetically active tissues (RUBISCO (Worrell et al., *The Plant Cell*, 3:1121–1130 (1991), which is hereby incorporated by reference)) or other mesophyll-cell-specific promoter (Datta et al., *Theor. Appl. Genet.*, 97:20–30 (1998), which is hereby incorporated by reference) or fibers (cotton-fiber-, xylem fiber-, or extra-xylary-fiber-specific or enhanced promoters). Other promoters can be used that ensure expression only in specified organs, such as the leaf, root, tuber, seed, stem, flower or specified cell types such as parenchyma, epidermal, or vascular cells. One example of a tissue specific promoter is the RB7 promoter that is root specific (U.S. Pat. No. 5,459,252, which is hereby incorporated by reference). Such promoters may be used either alone or in combination to optimize over-expression in the most desirable set of tissues or organs.

Preferred cotton fiber-enhanced promoters include those of the cotton fiber-expressed genes E6 (John et al., Plant Mol. Biol., 30:297–306 (1996) and John et al., Proc. Natl. Acad. Sci., 93:12768–12773 (1996), which are hereby incorporated by reference), H6 (John et al., Plant Physiol., 108:669–676, (1995), which is hereby incorporated by reference), FbL2A (Rinehart et al., Plant Physiol., 112:1331–1341 (1996) and John et al, Proc. Natl. Acad. Sci. USA, 93:12768–12773 (1996), which are hereby incorporated by reference), rac (Delmer et al., Mol. Gen. Genet., 248:43–51 (1995), which is hereby incorporated by reference); CelA (Pear et al., Proc. Natl. Acad. Sci USA, 93:12637–12642 (1996), which is hereby incorporated by reference); CAP (Kawai et al., Plant Cell Physiol. 39:1380–1383 (1998)); ACP (Song et al., Biochim. Biophys. Acta 1351:305–312 (1997); and LTP (Ma et al., Biochim. Biophys. Acta 1344:111–114 (1997)).

Preferred promoters enhancing expression in vascular tissue include the CAD 2 promoter (Samaj et al., Planta, 204:437–443 (1998), which is hereby incorporated by reference), the Pt4C11 promoter (Hu et al., Proc. Natl. Acad. Sci. USA, 95:5407–5412 (1998), which is hereby incorporated by reference), the C4H promoter (Meyer et al., Proc. Natl. Acad. Sci. USA, 95:6619–6623 (1998), which is hereby incorporated by reference), the PtX3H6 and PtX14A9 promoters (Loopstra et al., Plant Mol. Biol., 27:277–291 (1995), which is hereby incorporated by reference), the RolC promoter (Graham, Plant Mol. Biol., 33:729–735 (1997), which is hereby incorporated by reference), the Hvhsp17 promoter (Raho et al., J. Expt. Bot., 47:1587–1594 (1996), which is hereby incorporated by reference), and the COMT promoter (Capellades et al., Plant Mol. Biol., 31:307–322 (1996), which is hereby incorporated by reference).

Preferred promoters enhancing expression in stem tissue include pith promoters (Datta, Theor. Appl. Genet., 97:20–30 (1998) and Ohta et al., Mol. Gen. Genet., 225:369–378 (1991), which are hereby incorporated by reference), and the anionic peroxidase promoter (Klotz et al., Plant Mol. Biol., 36:509–520 (1998), which is hereby incorporated by reference). Preferred promoters enhancing expression in phloem, cortex and cork, but not xylem or pith, include the Psam-1 promoter (Mijnsbrugge et al., Plant and Cell Physiol., 37:1108–1115 (1996), which is hereby incorporated by reference).

Preferred promoters enhancing expression in seeds include the phas promoter (Geest et al., Plant Mol. Biol. 32:579–588 (1996)); the GluB-1 promoter (Takaiwa et al., Plant Mol. Biol. 30:1207–1221 (1996)); the gamma-zein promoter (Torrent et al. Plant Mol. Biol. 34:139–149 (1997)), and the oleosin promoter (Sarmiento et al., The Plant Journal 11:783–796 (1997)).

Truncated or synthetic promoters including specific nucleotide regions conferring tissue-enhanced expression may also be used, as exemplified by identification of regulatory elements within larger promoters conferring xylem-enhanced expression (Seguin et al., Plant Mol. Biol., 35:281–291 (1997); Torres-Schumann et al., The Plant Journal, 9:283–296 (1996); and Leyva et al., The Plant Cell, 4:263–271 (1992), which are hereby incorporated by reference).

In one embodiment of the invention the chimeric DNA construct is stably integrated into the genome of the cotton plant. When a plant is transformed by Agrobacterium mediated transformation, a portion of the Ti plasmid integrates into the plant genome and is stablely passed on to future generations of plant cells.

Numerous methods exist for transforming plant cells. The preferred methods include electroporation, Agrobacterium mediated transformation, biolistic gene transformation, chemically mediated transformation, or microinjection.

The vector described above can be microinjected directly into plant cells by use of micropipettes to transfer mechanically the recombinant DNA (Crossway, Mol. Gen. Genetics, 202:179–185 (1985), which is hereby incorporated by reference). The genetic material may also be transferred into the plant cell using polyethylene glycol (Krens et al., Nature, 296:72–74 (1982), which is hereby incorporated by reference).

Another approach to transforming plant cells with a gene that increases fiber and seed yield and fiber quality is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells.

Yet another method of introduction is fusion of protoplasts with other entities, either minicells, cells, lysosomes or other fusible lipid-surfaced bodies (Fraley et al., Proc. Natl. Acad. Sci. USA, 79:1859–63 (1982), which is hereby incorporated by reference).

The DNA molecule may also be introduced into the plant cells by electroporation (Fromm et al., Proc. Natl. Acad. Sci. USA, 82:5824 (1985), which is hereby incorporated by reference). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

Another method of introducing the DNA molecule into plant cells is to infect a plant cell with Agrobacterium tumefaciens or A. rhizogenes previously transformed with the gene. Under appropriate conditions known in the art, the transformed plant cells are grown to form shoots or roots, and develop further into plants. Generally, this procedure involves inoculating the plant tissue with a suspension of bacteria and incubating the tissue for 48 to 72 hours on regeneration medium without antibiotics at 25–28° C.

Agrobacterium is a representative genus of the gram-negative family Rhizobiaceae. Its species are responsible for crown gall (A. tumefaciens) and hairy root disease (A. rhizogenes). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by Agrobacterium and is stably integrated into the plant genome (Schell, *Science*, 237:1176–83 (1987), which is hereby incorporated by reference).

After transformation, whole transformed plants can be recovered. If transformed seeds were produced directly, these can be selected by germination on selection medium and grown into plants (Glough et al. *The Plant Journal* 16:735–743 (1998), which is hereby incorporated by reference). If transformed pollen was produced directly, this can be used for in vivo pollination followed by selection of transformed seeds (Touraev et al., *The Plant Journal* 12:949–956 (1997), which is hereby incorporated by reference). If meristems were transformed, these can be grown into plants in culture then transferred to soil (Gould, J. et al., *Plant Cell Rep.* 10:12–16 (1991), which is hereby incorporated by reference).

If protoplasts or explants were transformed, plants can be regenerated. Plant regeneration from cultured protoplasts is described in Evans et al., *Handbook of Plant Cell Cultures*, Vol. 1, New York, New York:MacMillan Publishing Co., (1983); and Vasil, ed., *Cell Culture and Somatic Cell Genetics of Plants*, Orlando:Acad. Press, Vol. I (1984), and Vol. III (1986), which are hereby incorporated by reference. Means for regeneration vary from species to species of plants, but generally a suspension of transformed protoplasts or a petri plate containing transformed explants is first provided. Callus tissue is formed and shoots may be induced from callus and subsequently rooted.

Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

It is known that practically all plants can be regenerated from cultured cells or tissues, including but not limited to, species of sugarcane, sugar beets, cotton, forest trees, forage crops, and fiber producing plants. Regeneration is also possible in seed-producing plants including, but not limited to, maize, rice, wheat, soybean, rape, sunflower, and peanut.

After the expression cassette is stably incorporated in transgenic plants, it can be transferred to other plants by sexual crossing. Any of a number of standard breeding techniques can be used, depending upon the species to be crossed.

Once transgenic plants of this type are produced, the plants themselves can be cultivated in accordance with conventional procedure with the presence of the gene encoding the sucrose phosphate synthase resulting in enhanced seed yield and/or enhanced fiber yield and/or enhanced fiber quality. Alternatively, transgenic seeds are recovered from the transgenic plants. These seeds can then be planted in the soil and cultivated using conventional procedures to produce transgenic plants.

The present invention also provides seeds produced from the transgenic plant having increased synthesis of sucrose phosphate synthase.

In another embodiment, the invention provides a method of increasing the yield of cotton plant by introducing into a cotton plant a chimeric DNA construct that alters sucrose phosphate synthase activity in an amount sufficient to increase the yield of the cotton plant. A chimeric gene may be introduced into plant cells or tissue. Transformed cells are selected, usually by the use of a selectable marker. The transformed cells are then used to generate a transformed plant (Fraley et al., *Proc. Natl. Acad. Sci. USA*, 79:1859–1863 (1982), which is hereby incorporated by reference).

Preferred plants are cotton plants. The transformed plants may have an increase in the yield of cotton seeds or cotton fiber.

The present invention also provides a method of increasing the quality of cotton fiber produced from a cotton plant by introducing into a cotton plant a chimeric DNA construct that alters the sucrose phosphate synthase activity in an amount sufficient to increase the quality of the cotton fiber produced by the cotton plant.

The level of sucrose phosphate synthase may be increased by expressing factors that increase the level of expression of the gene. Such factors may act on regulatory sites controlling expression that are normally located near the sucrose phosphate synthase gene or heterologous regulatory sites located near the gene in a chimeric construct. Alternatively, the level of sucrose phosphate synthase may be increased by introducing a chimeric DNA construct that directly expresses a sucrose phosphate synthase.

Generally, the present invention can be used to change the ratio of cellulose to the dry weight of the whole plant or to the dry weight of plant components by introducing into a plant a chimeric DNA construct capable of altering sucrose phosphate synthase activity in an amount sufficient to change the ratio of cellulose to the dry weight of the whole plant or plant components. The change in cellulose can be observed in relation to total weight of the plant or fractionated parts of plants including, but not exclusively, starch, total cell walls, cell wall of fibers, particular organs such as stems, or cell wall components such as pectins, hemicelluloses, proteins, extractives, and lignin. The change in the ratio of cellulose to the fractionated parts of plants can be observed when the fractionated parts are considered alone or in any additive combination.

Changes in qualities as claimed in this invention refer to changes of at least 10% compared to a plant lacking the transgene. For example, the ratio of cellulose in cell walls may be changed from 20% to 18% or lower or 22% or higher. Such change compared to parental level could apply to all cell walls or any cell wall fraction of a plant.

In a preferred embodiment, the dry weight of cellulose may be increased so that its ratio to other dry weight components exceeds 40%. Such increase to exceed 40% could apply to wood, fibers, and other cellulose-rich cell walls such as collenchyma and thickened xylem parenchyma.

To accomplish certain changes, the level of sucrose phosphate synthase may be decreased by expressing factors that decrease the level of expression of the gene. Such factors may act on regulatory sites controlling expression that are normally located near the sucrose phosphate synthase gene or heterologous regulatory sites located near the gene in a chimeric construct. Alternatively, in anti-sense technology, the level of sucrose phosphate synthase may be decreased by introducing a chimeric DNA construct that contains the complementary cDNA of a sucrose phosphate synthase (Arndt et al., *Genome*, 40:785–797 (1997), which is hereby incorporated by reference). Alternatively, decreased SPS activity might be induced by homology dependent gene silencing (Wassenegger et al. *Plant Mol. Biol.* 37:349–362 (1998), which is hereby incorporated by reference), virus-induced gene silencing (Baulcombe, *Curr. On. Plant Biol.* 2:109–113 (1999), which is hereby incorporated by reference), chimeric RNA/DNA oligonucleotides (Zhu et al., *Proc. Natl. Acad. Sci. USA* 15:8768–8773 (1999), which is hereby incorporated by reference), or homologous recombination (Shalev et al. *Proc. Natl. Acad. Sci. USA* 96:7398–7402 (1999), which is hereby incorporated by reference).

In yet another embodiment, the invention provides a method of increasing tolerance of photosynthetic efficiency to cool night temperatures by introducing into a plant a chimeric DNA construct capable of altering sucrose phosphate synthase activity in an amount sufficient to increase tolerance of photosynthetic efficiency to cool night temperatures.

The present invention can be used to regulate the thickness of cell walls in a plant by introducing into the plant a chimeric DNA construct that will change the sucrose phosphate synthase activity. In particular, the method can be used to increase the yield of harvestable fiber from any fiber producing plant.

In a preferred embodiment, the plant is a fiber producing plant. More preferred fiber producing plants are sugarcane, sugar beets, forest trees, forage crops, fiber producing plants, and seed producing plants.

In yet another embodiment, the present invention can be used to increase the harvestable yield of fiber from a plant. The invention may also be used to alter the quality of fiber isolated from the plant . . . Changes in sucrose phosphate synthase can change fiber strength, fiber length or weight per unit length. Changes may either increase or decrease the strength, length or weight per unit length.

The present invention can be used to increase the yield of seed harvested from a seed producing plant by introducing into the plant a chimeric DNA construct that will increase the sucrose phosphate synthase activity.

The methods of the invention are broadly applicable and can be used in a wide variety of plants including cotton, forest trees, forage crops, beets, flax, hemp, jute, and other fiber-producing plants. They can also be used in seed producing plants including cotton, flax, wheat, rice, corn, soybean. *Brassica sp.* (e.g. rape), sunflower, safflower, peanut, palm, and other seed producing plants.

The methods of the invention are further described in the examples that follow.

EXAMPLES

Example 1

Materials and Methods

Most plants described were grown in one chamber at the Duke University Phytotron: 360 ppm (normal) $CO_2$; 30°/15–19° C. day/night cycle; 14h day/10 h night; 1200 $\mu$mol $m^{-2}s^{-1}$ (metal halide) illumination; irrigation 2× daily with ½ strength Hoagland's solution; potted in a mixture of gravel and sand in 4 gallon pots. A change to 30/19° C. from 30/15° C. occurred after about 4 months growth, which was about half-way through the maturation of first bolls in C312 and all transgenic lines. This temperature condition is subsequently referred to as 30/15° C. for simplicity. This chamber is emphasized because its temperature and $CO_2$ conditions represent those likely to be encountered by cotton crops in the field, for example but not exclusively on the Texas Southern High Plains.

Other plants were grown in the Duke University Phytotron in 3 other chambers as described except with the following changes: (a) 360 ppm $CO_2$, 30°/28° C. day/night cycle; (b) 700 ppm (elevated) $CO_2$, 30°/15–19° C. day/night cycle; and (c) 700 ppm $CO_2$, 30°/28° C. day/night cycle.

Other plants were grown in the Texas Tech University greenhouse: natural $CO_2$ and illumination; approximately 32/22° C. day/night cycle; 2 gallon pots; irrigation 2–3× daily; slow-release fertilizer in the soil and soluble fertilizer applied 1× weekly.

All open bolls were harvested from each plant from which seed and fiber parameters were evaluated. Lint fiber was removed from the seeds by hand-stripping. Cotton seeds are covered with lint fiber (the long fiber used for textiles) and fuzz fiber (short fibers used in various industrial applications). (Lint) fiber weight and fuzzy seed weight from each plant was determined by weighing. Hereafter, 'fiber' refers to lint fiber, with fuzz fiber specified when necessary. Seed number per plant was determined by counting. (Seeds and fiber of underdeveloped "motes" were not included.) Fiber was sent to Cotton Incorporated, Raleigh, NC for HVI, AFIS, and Mantis fiber quality analysis. Seeds from the 30/15° C. chamber were subsequently acid-delinted, air-dried, and weighed. From this chamber, fuzz fiber weight per seed was determined by subtraction of the weights of fuzzy and delinted seeds.

For plants for which stem weight was determined, any unopened bolls and leaves and petioles were removed. Above-ground stems were oven-dried and weighed.

The plant line used is a Coker 312 wild-type (untransformed parent) and four transgenic lines. Transgenic plant lines, each known to represent separate transformation events, are designated 13-3a, 225-17a, 40-4b, and 40-6a. T0, T1, or T2 represent primary transformants and the first and second filial generations, respectively. All transgenic plants tested were Kanamycin resistant as determined from formation of lateral roots of germinating seedlings within agar containing Kanamycin. The segregation ratio of seeds germinated on kanamycin is expressed as resistant/sensitive ratio (Table 1). Ratios were assessed after 7–14 days to include most slow-germinating seeds.

The number of individual plants grown in the Phytotron to yield average data for each parameter (except for 40-6a-4) is indicated as Phytotron Plants (n) (Table 2). Line 40-6a-4, although it generally performed consistently with the other lines, was omitted from fiber quality averages because it was represented by only one plant in the 30/15° C., 360 ppm $CO_2$ chamber. Values from two T2 lineages of line 40-4b were averaged together because T1#1 and T1#4 are similar siblings (except for segregation ratio) that generated similar T2 progeny.

Leaf and fiber RNA levels were determined by Northern analysis of the mRNA for foreign SPS in the leaf, scored as positive or negative (Table 1). Extractable SPS activity (production of sucrose) is standardized as $\mu$mol sucrose/mg chlorophyll/hour for leaf activity or as $\mu$mol sucrose/mg protein/hour for fiber activity (Table 1).

The Boll # per Plant is the number of non-aborted bolls on each plant.

The Delinted Seed Weight per Seed (g) and (Lint) Fiber Weight per Seed (g) (Table 2) are data derived from all open bolls of each plant at the time the experiment was terminated. Under 30/28° C., all bolls had opened, but under 30/15° C., some unopened bolls were left on each plant at termination. Each data point represented 192–487 seeds yielding 24.5–48.5 g lint fiber.

Bulk (or bundle) fiber properties as determined by automated HVI and AFIS testing are summarized in Tables 3 and 4. The fiber micronaire (by HVI) is a unitless measurement that depends both on fiber maturity (or wall thickness determined by secondary wall cellulose content) and fiber diameter.

Fiber bundle strength (by HVI) is expressed in units of (cN/tex). It is the specific strength of the fiber bundle is which the individual fiber fineness (tex) is calculated from the Micronaire value.

Fiber fineness (by AFIS) is expressed as (mTex). It represents the weight, in milligrams, of one kilometer of the fiber. One thousand meters of fibers with a mass of 1 milligram equals 1 millitex.

The fiber maturity ratio (by AFIS) is an expression of the degree of cell wall thickening (depending on secondary cell wall cellulose deposition). It is the ratio of fibers with a 0.5 (or more) circularity ratio divided by the amount of fibers with 0.25 (or less) circularity. (Fibers with thicker walls are less prone to collapse and remain more circular upon drying.) The higher the maturity ratio, the more mature the fibers are and the better the fibers are for dyeing.

The immature fiber content ("IFC %", by AFIS) is the percentage of fibers with less than 0.25 maturity. The lower the IFC %, the more suitable the fiber is for dyeing.

Several different units are used as indicators of fiber length. Table 3 shows values for three of these as now described. Upper half mean ("UHM", by HVI) is the mean length of the longest one half of the fibers (weight biased). The fiber Uniformity Index ("UI", by HVI) expresses the ratio of the mean value (Mean Length) to the Upper Half Mean Length. It is a measure of the fiber length scatter within the population; if all fibers were the same length UI would equal 100%. Short Fiber Content ("SFC %", by HVI) is the percentage of fibers less than ½" long on a weight basis. HVI is thought to measure Short Fiber Content as determined by genetics only since the measurement does not impose additional potential fiber breaking stress.

Other fiber length indicators discussed in the text are as follows. The weight basis length ("L(w)" [in], by AFIS) is the average length of fibers calculated on a weight basis. The number basis length ("L(n)" [in], by AFIS) is the mean length of fibers calculated by number. The length "L5% (n)" [in] (by AFIS) is the 5% span length, or the length spanned by 5% of the fibers when they are parallel and randomly distributed. The length "L2.5% (n)" [in] (by AFIS) is the 2.5% span length, or the length spanned by 2.5% of the fibers when they are parallel and randomly distributed. The "UQL (w)" [in] (by AFIS) is the upper quartile length of fibers by weight, or the length exceeded by 25% of the fibers by weight. Finally, the "SFC (n)" [in] and "SFC (w)" [in] (by AFIS) are the percentage of fibers less than 0.50 inches long on a number and weight basis, respectively. In contrast to HVI, AFIS beats the fibers before taking these measurements, which has potential to cause fiber breakage. Therefore, AFIS SFC values are a good indication of the characteristics of the fiber after normal processing.

Single fiber strength and elongation parameters derived from Mantis testing are summarized in Table 5. "Tb" [g] is grams of force to break a single fiber. "Elongation" [%] is single fiber elongation before break as % of original length. "Work" [µJ] is a composite of Tb and Elongation, representing the work expended to break a single fiber.

Detailed methods for particular experiments are included under the Examples.

Example 2

Summary of Results Demonstrating Increased Fiber and Seed Yield in Transgenic Plants with Increased SPS Activity Transgenic cotton plants with spinach SPS under the control of a constitutive promoter showed foreign gene expression in the leaf and fiber as demonstrated by Northern analysis. At the T1/T2 generation, they showed average increased SPS enzyme activity of 3.3 times and 2.3 times in the leaf and fiber, respectively, compared to parental C312 (Table 1). In this and all following tables, values indicating superior features of transgenic plants compared to parental C312 are shown in bold.

TABLE 1

Characterization of Spinach SPS gene expression and Total SPS Activity in Transgenic Plants

| Plant Line | Segregation Ratio | Leaf RNA | Fiber RNA | Leaf SPS Activity (chlorophyll) | Normalized Leaf SPS Activity | Fiber SPS Activity (protein) | Normalized Fiber SPS Activity |
|---|---|---|---|---|---|---|---|
| C312-wt | na | – | – | 23.53[a] | 1.0 | 39.91 | 1.0 |
|  |  |  |  | 31.30[b] | 1.0 |  |  |
| 13-3a |  |  |  |  |  |  |  |
| T0 |  | + |  | 119.2 | 5.1 |  |  |
| T1 | 22:6 |  |  |  |  |  |  |
| T1#1 @ T2 | 66:0 |  | + | 127.2 | 4.0 | 103.39 | 2.6 |
| 225-17a |  |  |  |  |  |  |  |
| T0 |  | + |  | 118.5 | 5.0 |  |  |
| T1 | 25:12 |  | + | 121.8 | 3.9 | 93.71 | 2.4 |
| 40-4b |  |  |  |  |  |  |  |
| T0 |  | + |  | 107.3 | 4.6 |  |  |
| T1 | 11:4 |  |  |  |  |  |  |
| T1#1 @ T2 | 51:16 |  |  | 60.3 | 1.9 | 91.67 | 2.3 |
| T1#4 @ T2 | 10:0 |  | + | 66.4 | 2.1 | 76.00 | 1.9 |

TABLE 1-continued

Characterization of Spinach SPS gene expression and Total SPS Activity in Transgenic Plants

| Plant Line | Segregation Ratio | Leaf RNA | Fiber RNA | Leaf SPS Activity (chlorophyll) | Normalized Leaf SPS Activity | Fiber SPS Activity (protein) | Normalized Fiber SPS Activity |
|---|---|---|---|---|---|---|---|
| 40-6a | | | | | | | |
| T0 | | + | | 89.3 | 3.8 | | |
| T1 | 6:5 | | | | | | |
| T1#4 @ T2 | 9:2 | | | 57.6 | 1.8 | 74.12 | 1.9 |
| Transgenic Average at T1/T2[c] | | | | 103.9 | 3.3 | 85.4 | 2.3 |

[a]Value measured and used for T0 comparisons.
[b]Value measured and used for T1 and T2 comparisons.
[c]Excludes values for line 40-6a and uses a composite average value for line 40-4b to parallel the procedures used in analysis of fiber quality data.

Over the first 9 weeks of growth in the 30/15° C., 360 ppm $CO_2$ Phytotron chamber during which plant height and leaf number were measured, the transgenic lines grew similarly to parental C312. The average height of the transgenic plants was 0.90× the value for parental C312. The average leaf number of the transgenic plants was 1.02× parental C312.

In the 30/15° C., 360 ppm $CO_2$ Phytotron chamber, up-regulated SPS gene expression caused increases in yield components of the fiber and seed crop (Table 2).

seed and fiber per seed generates increased yield. Transgenic plants over-expressing SPS achieve increased yield of two types of crops at the same time: seed yield based primarily on storage of protein and oil and fiber yield based on storage of cellulose. Therefore, plants that over-express SPS can be predicted to generate more income per acre for the cotton producer based on crop yield alone. Coker 312 plants over-expressing SPS can also be used for future transformations to help overcome any potential yield drag from use

TABLE 2

Yield Components of SPS Transgenic Plants Compared to Parental C312 (at 30/15° C. and 360 ppm $CO_2$)

| Plant Line | Phytotron Plants (n) | Boll # per Plant | Normalized Boll # | Delinted Seed Weight per Seed (g) | Normalized Seed Weight per Seed | Fiber Weight per Seed (g) | Normalized Fiber Weight per Seed |
|---|---|---|---|---|---|---|---|
| C312-wt 13-3a | 4 | 22.8 | 1.0 | 0.090 | 1.0 | 0.047 | 1.0 |
| T1#1 @ T2 225-17a | 4 | 26.5 | 1.16 | 0.107 | 1.19 | 0.058 | 1.23 |
| T1 40-4b | 4 | 26.0 | 1.14 | 0.110 | 1.22 | 0.063 | 1.34 |
| T1#1 & #4 @ T2 40-6a | 5 | 28.2 | 1.24 | 0.100 | 1.11 | 0.057 | 1.21 |
| T1#4 @ T2 | 1 | 28.0 | 1.23 | 0.105 | 1.17 | 0.054 | 1.15 |
| Transgenic Average at T1/T2[a] | | 26.9 | 1.18 | 0.106 | 1.18 | 0.059 | 1.25 |

[a]Average omits line 40-6a because of few replications.

Both cotton fiber and cotton seeds are valuable crops, the lint fibers for use in textiles and other applications and the seeds as a source of oil and seed meal. In addition, short fuzz fibers (also called linters) are harvested as a source of chemical cellulose, among other uses. Increases were observed in number of bolls per plant, seed weight per seed, fiber weight per seed, and fuzz fiber weight per seed. Boll number per plant indicates overall capacity for production of seeds with attached fiber. Furthermore, increased weight of of this old cultivar in genetic engineering. Seed and fiber yield can be maximized at the same time in other crop plants, and stiffer stems can be generated to resist lodging without sacrifice of seed yield.

Increased Boll Number Per Plant:

Three transgenic lines tested in the 30/15° C., 360 ppm $CO_2$ chamber with good replication showed 14–24% increase in boll number per plant compared to parental C312, with an average increase of 18% (Table 2). Increased boll number of all transgenic lines was also observed in the 30/15° C., 700 ppm $CO_2$ and 30/28° C., 700 PPM $CO_2$ chambers.

Figure 5:
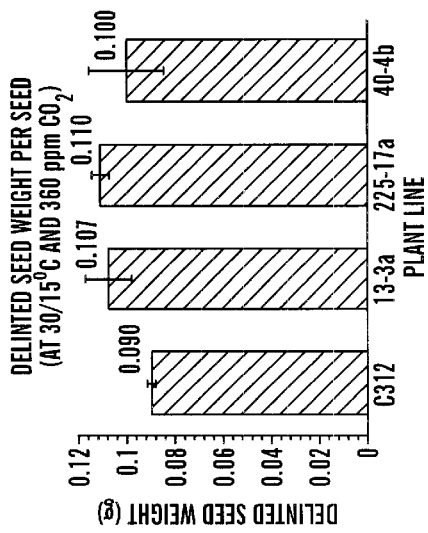
FIG. 5 is a histogram of fiber weight per seed, which shows elevation in all three transgenic lines. (Here and in all subsequent histograms, the error bars are standard deviations of the average. The average values are printed above each bar.)

Increased Fiber Weight Per Seed:

Three transgenic lines tested in the 30/15° C., 360 ppm $CO_2$ chamber showed 21–34% increase in fiber weight per seed compared to parental C312, with an average increase of 25% (Table 2, FIG. 5). This effect was not consistently observed in other chambers. Fiber weight per seed is a composite of fiber number, fiber length, and fiber wall thickness. Since average fiber micronaire (indicating increased wall thickness) and other related factors do increase in all transgenic lines across all chambers (see below), one may infer that unmeasured factors such as changing fiber number might impact fiber weight per seed under nearly constant warm temperature or elevated $CO_2$.

A measurement sometimes taken in lab-based yield analysis is "lint %"=(lint fiber weight)/(total seed and lint fiber weight). This parameter increases 1.8–2.7% for three transgenic lines above the parental C312 value of 31.14% (average increase for transgenics of 2.1%). This value underestimates fiber yield improvement in transgenic lines because seed weight also increases (see below).

Figure 6:
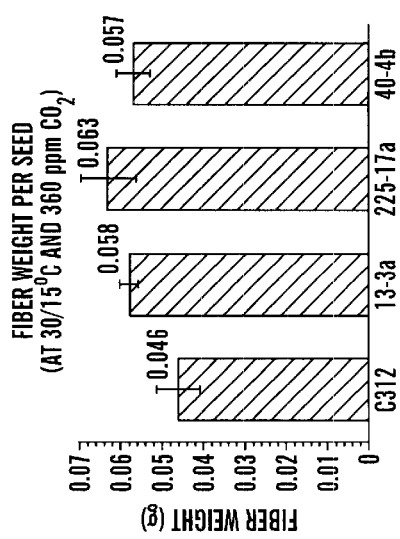
FIG. 6 is a histogram of delinted seed weight per seed. It shows elevation in all three transgenic lines.

Increased Seed Weight Per Seed:

Three transgenic lines tested in the 30/15° C., 360 ppm $CO_2$ chamber showed 11–22% increase in delinted seed weight per seed compared to parental C312, with an average increase of 18% (Table 2, FIG. 6). Only fuzzy seeds have been weighed from other chambers. However, comparing fuzzy and delinted values from the 30/15° C., 360 ppm $CO_2$ chamber indicates that fuzzy seed values are representative of the trends in seed yield. Fuzzy seeds showed increased seed weight per seed in the transgenic lines growing in the other three chambers with only one exception (225-17a showed seed weight per seed equal to parental C312 in the 30/28° C., 700 ppm $CO_2$ chamber).

Figure 7:
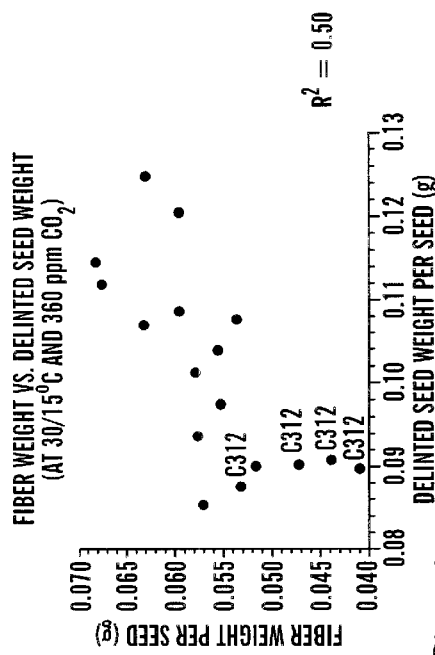
FIG. 7 is a histogram of the ratio of fiber weight per seed and delinted seed weight per seed. It shows that these two yield parameters tend to increase in parallel, with a small preference for increased fiber weight in transgenic lines.
Figure 8:
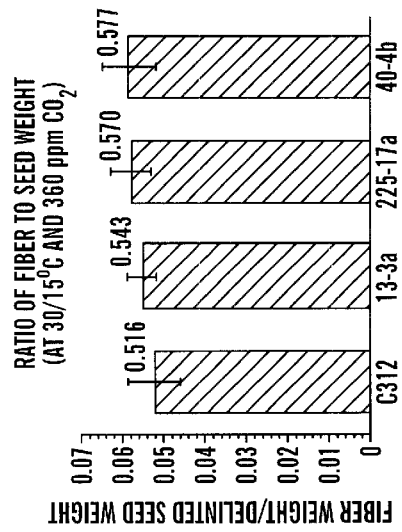
FIG. 8 is a scatter plot of fiber weight per seed vs delinted seed weight per seed. It shows that these two parameters are interdependent at the 50% level. (Here and with all other scatter plots, $R^2$ is the coefficient of determination calculated from the linear regression line. Also, data points from parental C312 are labeled to their right, whereas data point from the three transgenic lines are left unlabeled.) Note, however, that C312 does not shown any linear relationship because seed weight per seed shows little variability in the parental line. Therefore, the overall linear relationship among all the data points derives from the transgenic plants. The transgenic plants have more variability in and higher levels of delinted seed weight per seed and fiber weight per seed than parental C312 plants.

The ratio of Fiber Weight per Seed to Delinted Seed Weight per Seed in the 30/15° C., 360 ppm $CO_2$ chamber was increased by an average of 9.0% in three transgenic lines (FIG. 7). A scatter plot of fiber weight per seed vs. delinted seed weight per seed shows that transgenic plants separate from parental C312 through increases in both of these yield components together (FIG. 8). However, there is preferential enhancement of fiber weight compared to seed weight in SPS transgenic plants.

Figure 9:
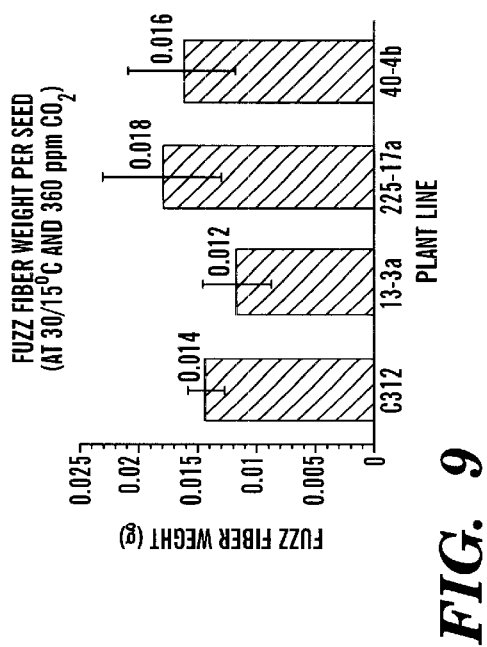
FIG. 9 is a histogram of fuzz fiber weight per seed. It shows elevation in two of three transgenic lines, and a decrease in one transgenic line.

Increased Fuzz Fiber Weight Per Seed:

Fuzz fiber weight per seed was obtained by subtracting the unit seed weight of delinted seed from the unit seed weight of fuzzy seeds from the 30/15° C., 360 ppm $CO_2$ chamber (FIG. 9). Two transgenic lines (225-17a and 40-4b) showed increases (averaging 19% increase compared to parental C312) and one transgenic line (13-3a) showed a decrease (19% decrease compared to parental C312). Seeds of line 13-3a also looked blacker before delinting, suggesting initiation of fewer fuzz fibers than on seeds of either parental C312 or the other two transgenic lines. Therefore, transgenic lines show some variation in numbers of fuzz fibers initiated, but, once initiated, over-expressed SPS enhances their yield similarly to lint fibers.

Example 3

Summary of Results Demonstrating Increased Fiber Quality as Analyzed by Automated HVI and AFIS on Bulk Samples Many spinning properties of cotton depend on its properties as a bulk sample. HVI and AFIS are automated systems that analyze these properties, yielding complementary information. These analyses show that the quality parameters of fiber produced by SPS transgenic plants are moving as a set into the premium quality range. Fiber from SPS transgenic plants is longer, stronger, and more mature—all these features are currently valued by the cotton processing and textile industries to make high quality fabrics. Even under a stressful 30/15–19° C. temperature cycle typical of the Texas Southern High Plains, the quality of fiber from SPS transgenic plants resembles that of premium cotton such as is traditionally grown in California. Therefore, cotton fiber from SPS transgenic plants can serve an expanded set of end-use markets and sell for a premium price. Producers growing SPS transgenic cotton should also be able to avoid price discounts for inferior quality such a low micronaire that can result from traditional cotton grown on the Texas Southern High Plains. Therefore, SPS transgenic cotton should stabilize or enhance income per acre for the cotton producer based on improved fiber quality.

Improvements Under 30/15° C., 360 ppm $CO_2$:

Key bulk fiber quality parameters from fiber grown in the 30/15° C., 360 ppm $CO_2$ chamber and analyzed by HVI and AFIS are shown in Table 3. Factors of increase for transgenic lines over parental C312 are shown in Table 4.

TABLE 3

Fiber Quality Parameters of SPS Transgenic Plants Compared to Parental C312 (at 30/15° C. and 360 ppm $CO_2$)

| Plant Line | Phytotron Plants (n) | Fiber Micronaire | Fiber Bundle Strength (cN/tex) | Fiber Fineness (mTex) | Fiber Maturity Ratio | Immature Fiber Content (%) | Fiber Length (UHM) (in) | Fiber Uniformity (UI, %) | Short Fiber Content (% by HVI) |
|---|---|---|---|---|---|---|---|---|---|
| C312-wt 13-3a | 4 | 3.68 | 27.1 | 167 | 0.89 | 7.45 | 1.04 | 83.1 | 7.5 |
| T1#1 @ T2 225-17a | 4 | 4.55 | 28.8 | 170 | 0.92 | 6.85 | 1.15 | 88.9 | 5.9 |
| T1 40-4b | 4 | 5.12 | 31.0 | 189 | 0.99 | 4.35 | 1.14 | 87.9 | 2.9 |
| T1#1 & #4 @ T2 40-6a | 5 | 4.50 | 31.1 | 180 | 0.95 | 5.64 | 1.12 | 84.8 | 5.9 |
| T1#4 @ T2 Transgenic | 1 | 5.30 | 29.6 | 177 | 0.96 | 5.20 | 1.08 | 86.1 | 11.3 |
|  |  | 4.72 | 30.3 | 180 | 0.95 | 5.61 | 1.14 | 87.2 | 4.9 |

TABLE 3-continued

Fiber Quality Parameters of SPS Transgenic Plants Compared to Parental C312
(at 30/15° C. and 360 ppm CO₂)

| Plant Line | Phytotron Plants (n) | Fiber Micronaire | Fiber Bundle Strength (cN/tex) | Fiber Fineness (mTex) | Fiber Maturity Ratio | Immature Fiber Content (%) | Fiber Length (UHM) (in) | Fiber Uniformity (UI, %) | Short Fiber Content (% by HVI) |
|---|---|---|---|---|---|---|---|---|---|
| Average at T1/T2[a] | | | | | | | | | |

[a]Average omits line 40-6a because of few replications.

TABLE 4

Changes in Fiber Quality Parameters of SPS Transgenic Plants
(at 30/15° C. and 360 ppm $CO_2$)
(Values are shown normalized to C312-wt values set to 1.0 or as % changes from parental C312 values.)

| Plant Line | Phytotron Plants (n) | Normalized Fiber Micronaire | Normalized Fiber Bundle Strength (cN/tex) | Normalized Fiber Fineness (mTex) | Normalized Fiber Maturity Ratio | Change in Immature Fiber Content (%) | Normalized Fiber Length (UHM) | Change in Fiber Uniformity (UI, %) | Change in Short Fiber Content (% by HVI) |
|---|---|---|---|---|---|---|---|---|---|
| C312-wt 13-3a | 4 | 1.00 | 1.00 | 1.00 | 1.00 | 7.45% | 1.00 | 8.31% | 7.5% |
| T1#1 @ T2 225-17a | 4 | 1.23 | 1.06 | 1.02 | 1.03 | −0.60% | 1.11 | +5.8% | −1.6% |
| T1 40-4b | 4 | 1.39 | 1.14 | 1.13 | 1.11 | −3.10% | 1.09 | +4.8% | −4.6% |
| T1#1 & #4 @ T2 40-6a | 5 | 1.22 | 1.15 | 1.08 | 1.07 | −1.81% | 1.07 | +1.7% | −1.6% |
| T1#4 @ T2 | 1 | 1.44 | 1.09 | 1.08 | 1.08 | −2.25% | 1.04 | +3.0% | +3.8% |
| Transgenic Average Changes at T1/T2[a] | | 1.28 | 1.12 | 1.08 | 1.07 | −1.84% | 1.10 | +4.1% | −2.6% |

[a]Average omits 40-6a because of few replications.

Figure 10:
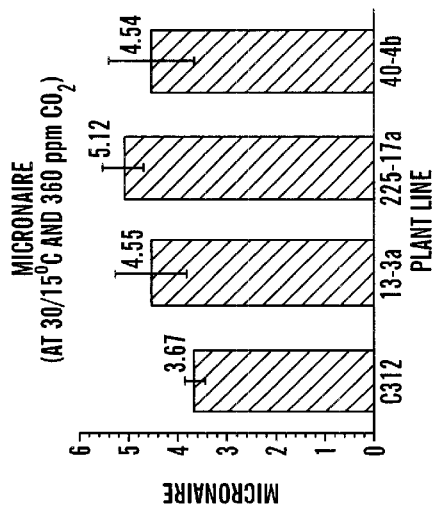
FIG. 10 is a histogram of micronaire, which shows elevation in all three transgenic lines.
Figure 11:
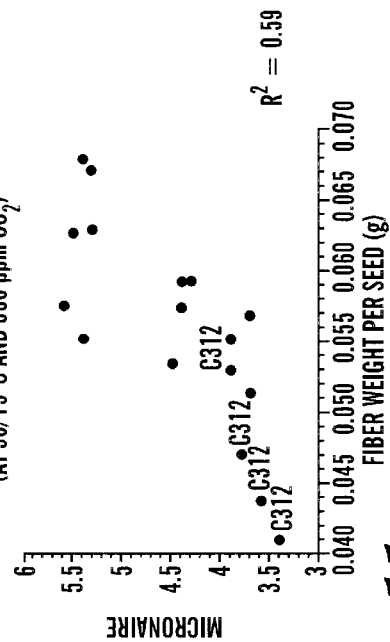
FIG. 11 is a scatter plot of micronaire vs fiber weight per seed showing that these two parameters are interdependent at the 60% level. This is sensible since fiber weight per seed depends on 3 factors: number of fibers, length of fibers, and fiber wall thickness. Of these 3 factors, micronaire would depend only on fiber wall thickness. Note that this linear relationship also holds for C312, but the transgenics have higher values for fiber weight per seed and micronaire.

Micronaire. Three transgenic lines showed an average increase of 28% to attain an average micronaire of 4.72 (FIG. 10). Micronaire depends on secondary wall thickness and fiber diameter. It is desirable that increases in micronaire occur because of increased secondary wall thickness, not because of increased fiber diameter. The fiber diameter is estimated from the standardized relationship between Fiber Fineness and Fiber Maturity Ratio (Table 3) and found to be little-changed in transgenic lines. Both parental C312 and the transgenic lines had estimated fiber diameter between 16.5–17.0 μm. Furthermore, a plot of Micronaire vs. Fiber Weight per Seed shows an interdependence at the 59% level (FIG. 11), supporting the existence of thicker walls in fibers of SPS transgenic plants. Other data on fiber strength, maturity ratio, and immature fiber content (see below) also support an increase in wall thickness of fiber from SPS transgenic plants. Over 90% of the thickness of the cotton fiber wall is due to deposition of almost pure cellulose in the secondary cell wall. Therefore, over-expression of SPS has increased the cellulose content of cotton fibers.

Fiber Bundle Strength. Three transgenic lines showed an average increase of 12% to attain an average bundle strength of 30.3 cN/tex.

Fiber Fineness. Three transgenic lines showed an average increase of 8% to attain an average fineness of 180. Higher fiber fineness is traditionally undesirable because it is usually attributed to larger fiber diameter. However, since fiber of SPS transgenic plants has diameter approximately equal to parental C312 (see above), the increased fineness is likely attributable to increased fiber wall thickness yielding more weight per unit length. Therefore, increased fineness of fiber from SPS transgenic plants is expected to be a neutral or positive fiber quality factor.

Fiber Maturity Ratio. Three transgenic lines showed an average increase of 7% to attain an average maturity ratio of 0.95, which falls in the "above average" range (0.95–1.00). This is superior to parental C312 with its average value of 0.89 in the "mature" range (0.85–0.95).

Immature Fiber Content. Three transgenic lines showed an average decrease of 1.84% to attain an average of 5.61% immature fibers. Transgenic fibers are superior to those of parental C312, which contain an average of 7.45% immature fibers.

Fiber length. Three transgenic lines showed an average increase in Upper Half Mean length of 10% to attain average UHM of 1.14 inches. The three lines also have more uniform fiber length, with average Uniformity Index increased 4.1% to attain average UI of 87.2%. The three lines also have fewer short fibers, with average Short Fiber Content by HVI decreasing 2.6% to attain average SFC % of 4.9%. In addition to data summarized in Tables 3 and 4, other AFIS parameters support increased fiber length in fibers of SPS transgenic plants. For the average of three transgenic lines, L(w) increases 7% to 1.06 inches, L(n) increases 9% to 0.96 inches, UQL (w) increases 6% to 1.19 inches, L5% (n) [in] increases 6% to 1.34 inches, and L2.5% (n) increases 5% to 1.46 inches. Similarly, AFIS showed that on average three transgenic lines had decreased short fiber content with SFC % (w) decreasing 1.0% to 3.1% and SFC % (n) decreasing 2.0% to 10.6%. (These AFIS SFC % averages omit the values from one plant of line 40-4b because they were extreme outliers that greatly skewed the averages away from the values for the other four plants in the line.) Since AFIS beats the fibers before taking the measurement, these reduced SFC % values are good indications for improved utility of fibers from SPS transgenic plants in normal fiber processing.

Improvements Under Diverse Environmental Conditions:

Many fiber quality parameters were enhanced most for transgenic lines compared to parental C312 in the 30/15° C., 360 $CO_2$ ppm chamber, which was the only typical growing condition for cotton tested. However, fiber quality was also maintained or enhanced in transgenic plants growing in the other Phytotron chambers where temperature was varied from 30/15° C. to 30/28° C. and/or $CO_2$ was varied from 360 ppm to 700 ppm. This is demonstrated by transgenic values and change from values for C312 of fiber quality data from the three transgenic lines growing in the other three chambers averaged together, excluding the 30/15° C., 360 ppm chamber that has been summarized independently. Over-expression of SPS maintains especially strong effects on Micronaire and average fiber length, L(n), with parallel consistent effects on UI and SFC.

Short Fiber Content (w) by HVI. 3.77%; decreased 1%.

Short Fiber Content (w) by AFIS. 3.95%; decreased 1.75%.

Changes within each plant line are compared in average values for the quality parameters of Micronaire, UHM, UI, bundle strength, SFC %, UQL, L(n), IFC %, and maturity ratio when 30/15° C. changed to 30/28° C. (at 360 ppm $CO_2$) or 360 ppm $CO_2$ changed to 700 ppm $CO_2$ (at 30/15° C.). These calculations show that over-expression of SPS in transgenic lines promotes nearly maximum increases in fiber quality even at the most limiting 30/15° C., 360 ppm $CO_2$ condition. In contrast, raising the minimum temperature or the $CO_2$ level substantially enhanced the Micronaire, UHM, UI, and bundle strength of parental C312. Therefore, high fiber quality in SPS transgenic plants is more independent of environment.

Example 4

Summary of Results Demonstrating Increased Fiber Quality as Analyzed by Mantis Single Fiber Tests Cotton fibers with higher individual fiber strength are highly valued by the textile industry because they break less frequently during processing. Therefore, average fiber length can be maintained at a higher value throughout processing and higher quality fabrics can be manufactured with fewer defects. Increasing individual fiber strength is a major goal of the cotton industry.

Mantis tests to determine single fiber strength were run on 100 fibers (two independent groups of 50 fibers each) from at least 4 plants from each plant line. Therefore, data in Table 5 are averages from at least 400 total fibers from each plant line.

TABLE 5

Single Fiber Strength of SPS Transgenic Plants Compared to Parental C312 (at 30/15° C. and 360 ppm $CO_2$)

| Plant Line | Fiber # | Tb (g) | Normal-ized Tb | Tb S.D. | Tb S.D. % | Elong (%) | Change in Elong % | Work (µJ) | Normal-ized Work | Work S.D. | Work S.D. % |
|---|---|---|---|---|---|---|---|---|---|---|---|
| C312-wt 13-3a | 400 | 5.30 | 1.00 | 2.45 | 46.2 | 15.05 | | 13.21 | 1.00 | 8.98 | 68.0 |
| T1#1 @ T2 225-17a | 400 | 5.90 | 1.11 | 2.55 | 43.2 | 17.40 | +2.35 | 15.99 | 1.21 | 8.62 | 53.9 |
| T1 40-4b | 400 | 7.18 | 1.35 | 2.85 | 39.7 | 16.67 | +1.62 | 18.09 | 1.37 | 9.55 | 52.8 |
| T1#1, #4 @ T2 | 500 | 6.60 | 1.24 | 2.71 | 41.1 | 16.89 | +1.84 | 17.22 | 1.30 | 9.21 | 53.5 |
| Transgenic Average | | 6.56 | 1.24 | 2.70 | 41.2 | 16.99 | +1.94 | 17.10 | 1.29 | 9.13 | 53.4 |

Tb: grams of force to break a single fiber
Elong %: Single fiber elongation before break as % of original length
Work: a composite of Tb and Elongation = work expended to break a Single fiber
XX S.D: Standard deviation of the value
XX S.D. %: % of the actual value represented by the standard deviation value Micronaire. 4.65; 1.13× compared to the C312 average value.
Fiber Bundle Strength. 30 cN/tex; 1.02×.
Fiber Maturity Ratio. 0.92, 1.03×.
Immature Fiber Content. 6.69%; decreased 1.1%.
Length (n). 0.95 inches; 1.08×.
Upper Quartile Length. 1.21 inches; 1.03×.
Fiber Uniformity Index. 87.7%; increased 1.3%.

Figure 13:
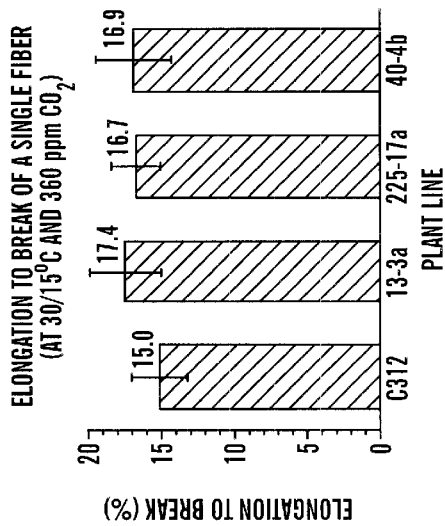
FIG. 13 is a histogram of elongation to break a single fiber (% of original fiber length). It shows elevation in all transgenic lines. However, note that Elongation is highest in transgenic line 13-3a, which, among the transgenics, had the lowest increase in grams to break. This suggests that these two factors are primarily determined by different fiber properties, as would be predicted in theory and is confirmed by the scatter plots below.
Figure 15:
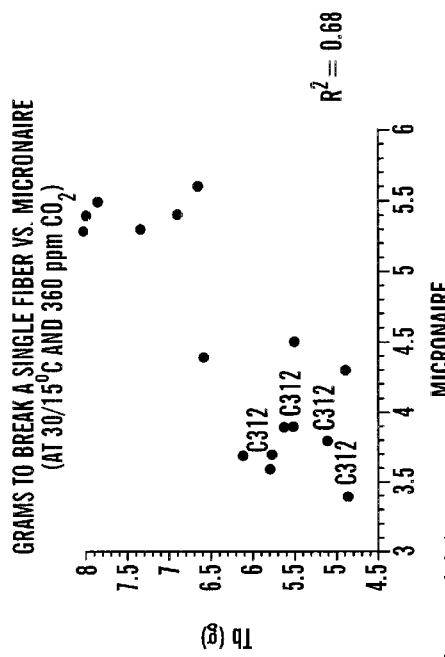
FIG. 15 is a scatter plot of grams of force to break a single fiber vs. micronaire. The graph shows an interdependency for these parameters over all data points of 68%. Both of these parameters would be expected to increase with a thicker fiber wall.
Figure 12:
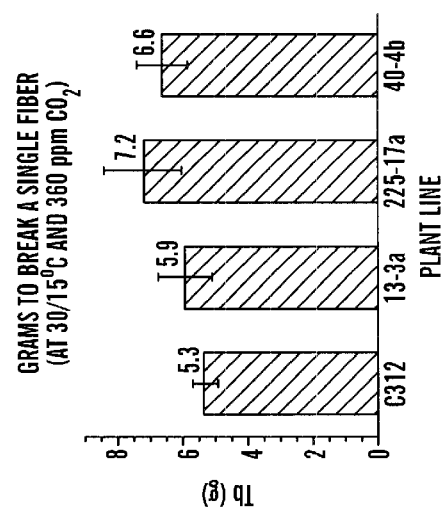
FIG. 12 is a histogram of grams of force to break a single fiber (Tb; g). It shows elevation in all transgenic lines.
Figure 14:
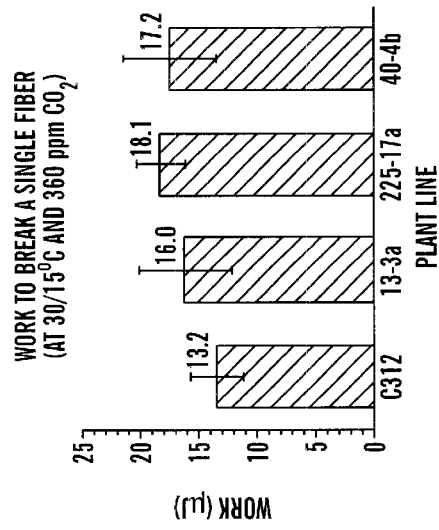
FIG. 14 is a histogram of work to break a single fiber ($\mu$J). Work, which is a composite factor calculated from grams to break and elongation, is elevated in all transgenic lines.
Figure 16:
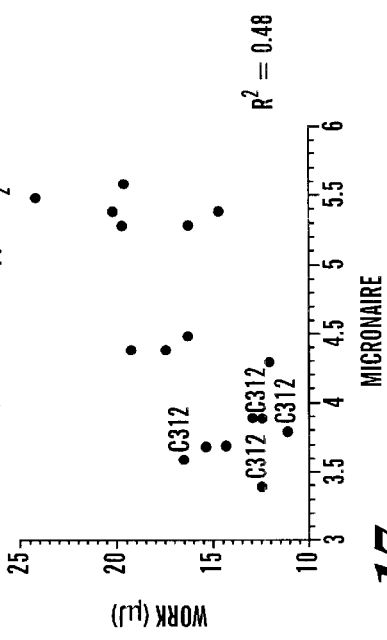
FIG. 16 is a scatter plot of grams of force to break a single fiber vs. fiber weight per seed. These parameters are interdependent at a level of 61%, which is similar to the dependence on micronaire (See FIG. 15). This supports the hypothesis that increased fiber weight per seed is due in large part to increased fiber wall thickness, since the two other parameters that can increase fiber weight per seed (increased fiber number and increased fiber length) would not be expected to increase grams to break.
Figure 17:
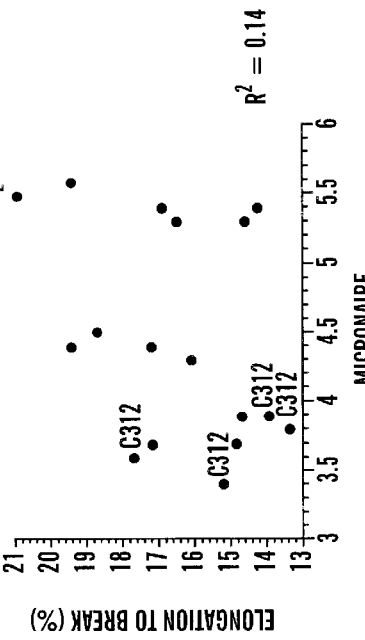
FIG. 17 is a scatter plot of work to break a single fiber vs. micronaire. These parameters are interdependent at a level of 48%. The intermediary level of dependency compared to grams to break and elongation alone (See FIG. 19) is reasonable for this composite factor.
Figure 18:
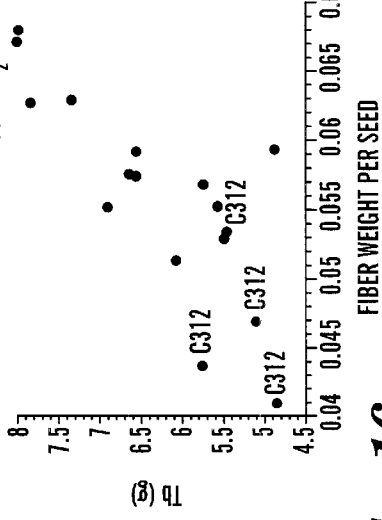
FIG. 18 is a scatter plot of work to break a single fiber vs. fiber weight per seed. These parameters are interdependent at a level of 39%, which is similar to the dependence on micronaire (See FIG. 17). As just described for FIG. 16, this supports the hypothesis that increased fiber weight per seed is due in large part to increased fiber wall thickness.
Figure 19:
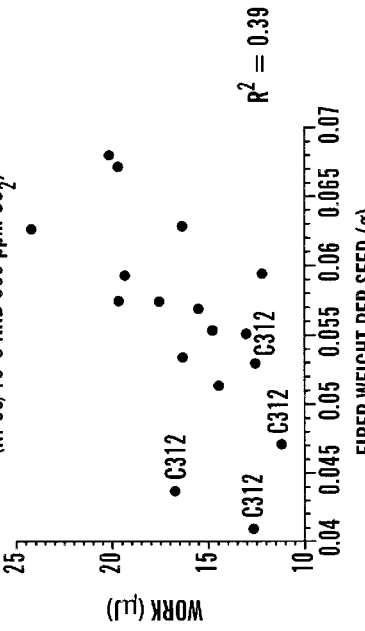
FIG. 19 is a scatter plot of elongation to break vs. micronaire. The graph shows that these parameters are not interdependent. Therefore, over-expression of SPS is predicted to enhance elongation by a mechanism independent of fiber wall thickness, which is consistent with theory.
Figure 20:
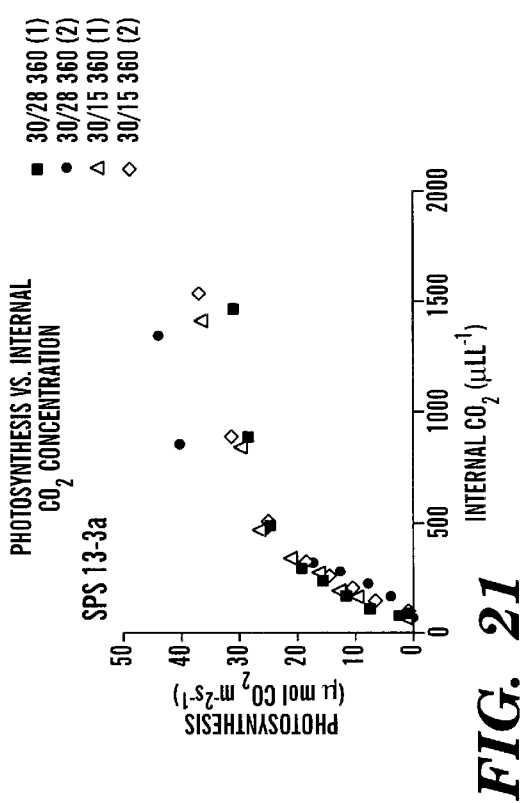
FIG. 20 is four overlayed scatter plots of photosynthetic rate vs. internal CO2 concentration for parental C312 growing in the Phytotron. Empty symbols are for two plants growing at 30/15° C. and filled symbols are for two plants growing at 30/28° C. All plants were assayed at 30° C. The graphs show that for parental C312, a previous cool night suppresses photosynthetic rate during the warm day.

Table 5 shows that single fiber strength as manifested in Tb, Elongation, and Work is consistently improved in all 3 transgenic lines compared to parental C312. On average in three transgenic lines, Tb is increased 24% to 6.56 g (FIG. 12), Elongation is increased 1.94% to 16.99% (FIG. 13), and Work is increased 29% to 17.10 µJ (FIG. 14). (HVI did not show any increase in Elongation % of transgenic lines compared to parental C312 because the bundle-based HVI test will reflect only the elongation of the weakest fibers in the bundle.) Also, the standard deviation is a lower percentage of the transgenic single fiber strength values (averaging 14.6% lower for Work), demonstrating improved uniformity of single fiber strength. (Results of Mantis single fiber tests are expected to have high standard deviations).

The scatter plots in FIGS. 15–19 show correlations between single fiber strength parameters and Micronaire or Fiber Weight per Seed from the 30/15° C., 360 ppm $CO_2$ chamber. These illustrate positive correlations between Tb and Work and Micronaire and Fiber Weight per Seed (FIGS. 15–18). In contrast, no positive correlations were observed between Elongation and Micronaire (FIG. 19) or Fiber Weight per Seed. Coefficients of determination show that 39–68% of the increases in Tb and Work are determined by increases in Micronaire and Fiber Weight per Seed. These positive correlations are primarily determined by distinctly separated groups of data points from the fibers of SPS transgenic plants. This point is emphasized by Table 6 showing coefficients of determination ($R^2$) for each plant line considered separately. In contrast to the transgenic lines, parental C312 shows no substantial, positive $R^2$ values. Therefore, over-expression of SPS causes increased values of Micronaire in transgenic fibers that are correlated with increased values of single fiber strength compared to parental C312.

Example 5
Photosynthetic Efficiency Under Cool Night Temperatures

Over-expression of SPS in the leaves increases tolerance to cool nights by maintaining photosynthetic rates equal to warm-grown plants during the warm days following a 15° C. night. In contrast, untransformed cotton shows reduced photosynthetic rate in the warm day following a cool night.

Transgenic plants and parental C312 plants growing in the Phytotron were assayed for photosynthetic efficiency between 7–14 weeks of age. The first fully expanded leaf from the apex (judged by dark green color, shape, and size—the 3rd or 4th leaf down) was clamped and assayed for photosynthetic efficiency using a ADC LCA-4 analyzer under variable internal $CO_2$ concentrations. Plants growing at 30/28° C. were assayed between 7–10 weeks of age and plants growing at 30/15° C. were assayed between 10–14 weeks of age. In the earliest case, the plants would have been exposed to the experimental conditions for about 4 weeks. The plants were assayed at 30° C. and at 4 h into the photoperiod, which also represented 3 h after complete rewarming from 28° C. or 15° C. to 30° C. Two plants were assayed for each line in each chamber.

Figure 21:
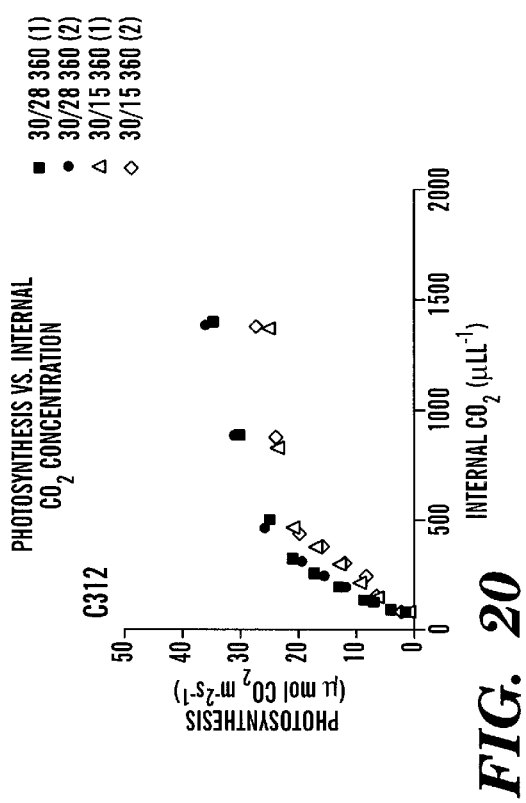
FIG. 21 is four overlayed scatter plots of photosynthetic rate vs. internal CO2 concentration for the transgenic line 13-3a-1 growing in the Phytotron. Empty symbols are for two plants growing at 30/15° C. and filled symbols are for two plants growing at 30/28° C. All plants were assayed at 30° C. The graphs show that for this transgenic line, a previous cool has no effect on the rate of photosynthesis during the next warm day.
Figure 22:
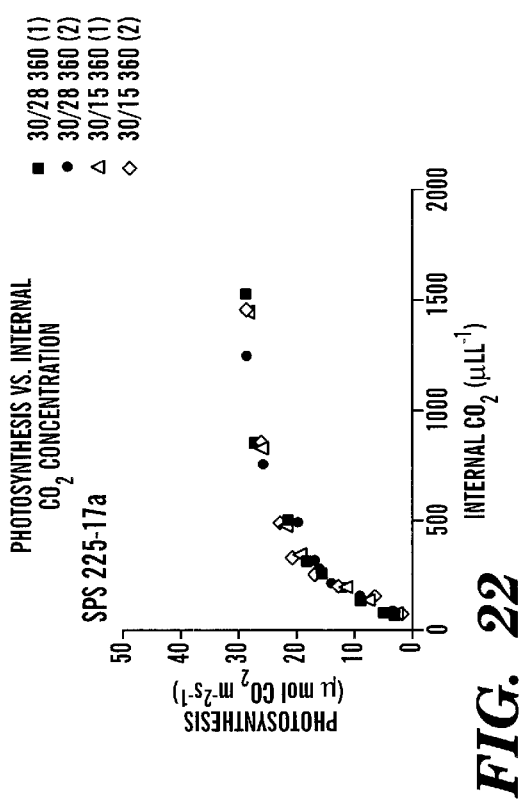
FIG. 22 is four overlayed scatter plots of photosynthetic rate vs. internal CO2 concentration for the transgenic line 225-17a growing in the Phytotron. Empty symbols are for two plants growing at 30/15° C. and filled symbols are for two plants growing at 30/28° C. All plants were assayed at 30° C. The graphs show that for this transgenic line, a previous cool has no effect on the rate of photosynthesis during the next warm day.

The graphs show photosynthetic rates over a range of internal $CO_2$ concentrations for parental C312 (FIG. 21) and two transgenic lines, 13-3a-1 (FIG. 22) and 225-17a (FIG.

TABLE 6

Coefficients of Determination ($R^2$) from Linear Regression Plots of Single Fiber Strength Parameters of Individual Plant Lines Plotted Against Micronaire and Fiber Weight Per Seed

| | Work | | Tb | | Elongation | |
|---|---|---|---|---|---|---|
| Y Axis | | Fiber Weight | | Fiber Weight | | Fiber Weight |
| X Axis | Micronaire | per Seed | Micronaire | per Seed | Micronaire | per Seed |
| Plant Line | | | | | | |
| C312 | −0.10 | −0.10 | 0.16 | 0.15 | −0.29 | −0.29 |
| 13-3a | 0.50 | 0.06 | 0.37 | 0.00 | 0.56 | 0.30 |
| 225-17a | 0.40 | 0.67 | 0.95 | 0.99 | −0.57 | −0.31 |
| 40-4b | 0.34 | 0.83 | 0.83 | 0.54 | 0.10 | 0.83 |

The substantial positive correlations with Tb and Work for both Micronaire (in 3 transgenic lines) and Fiber Weight per Seed (in 2 transgenic lines) support the fact that the increases in Fiber Weight per Seed and Micronaire are due to increased cellulose deposition in the fiber wall. Increase in Fiber Weight per Seed due to increased fiber number or increase in Micronaire due to increased fiber diameter would not result in an increase in single fiber strength. (Note that fiber number per seed cannot be determined, whereas the data allow one to predict by standard methods that fiber diameter has not changed.) However, the lack of complete correlation between single fiber strength values and Micronaire and Fiber Weight per Seed suggests that over-expression of SPS also contributes independently to increased single fiber strength, with 52–61% of the increased work values being explained by factors other than increased wall thickness. Also, the tendency for elevated Elongation in transgenic fibers is, as expected, independent of increased cellulose content of the fiber wall. (Elongation is highly dependent on the orientation of cellulose microfibrils within the fiber wall.) This point is emphasized by comparing line 13-3a with other transgenic lines.

23). Normal atmospheric $CO_2$ concentration corresponds to internal $CO_2$ concentration of about 270 $\mu$L L$^{-1}$. Each graph is a compilation of four scatter plots, one for each plant of the line that was tested. The relative placement of empty symbols (30/15° C. condition) and filled symbols (30/28° C. condition) should be compared between the lines. Comparing photosynthetic rate below internal $CO_2$ concentrations of 500 $\mu$L L$^1$, all four plants in the two transgenic lines tested maintained, when growing under a 30/15° C. cycle, the same photosynthetic rate during the warm day as was observed for plants growing under 30/28° C. cycling. In contrast, parental C312 showed the expected cool-night-induced reduction in photosynthetic rate, even though the assay was always done during the warm day. For three of the four transgenic plants tested, this difference was maintained at all internal $CO_2$ concentrations tested.

The variability in plant age at the time of assay between 30/15° C. and 30/28° C. chambers means that the comparisons between temperature cycles should be considered tentative. However, use of the same type of leaf from actively growing plants in each case supports their usefulness.

It is not yet known why plants over-expressing SPS fail to acclimate photosynthesis in response to chilling as occurs in parental C312. Future analyses of leaf carbohydrate content will indicate whether more sucrose is synthesized during the warm day in transgenic plant leaves, which, coupled with higher rates of photosynthesis, might result in greater carbohydrate export from leaves to developing fibers during the day than occurs in parental C312. Such a mechanism could contribute to the increased seed and fiber yield and fiber quality of plants over-expressing SPS. It has also been observed that transgenic plants over-expressing SPS store less starch in their hypocotyls than parental C312. This indicates another source of extra carbohydrate that could help increase seed and fiber yield and fiber quality.

Example 6
Shift of Metabolic Flux Toward Cellulose in Sink Cells

Figure 2:
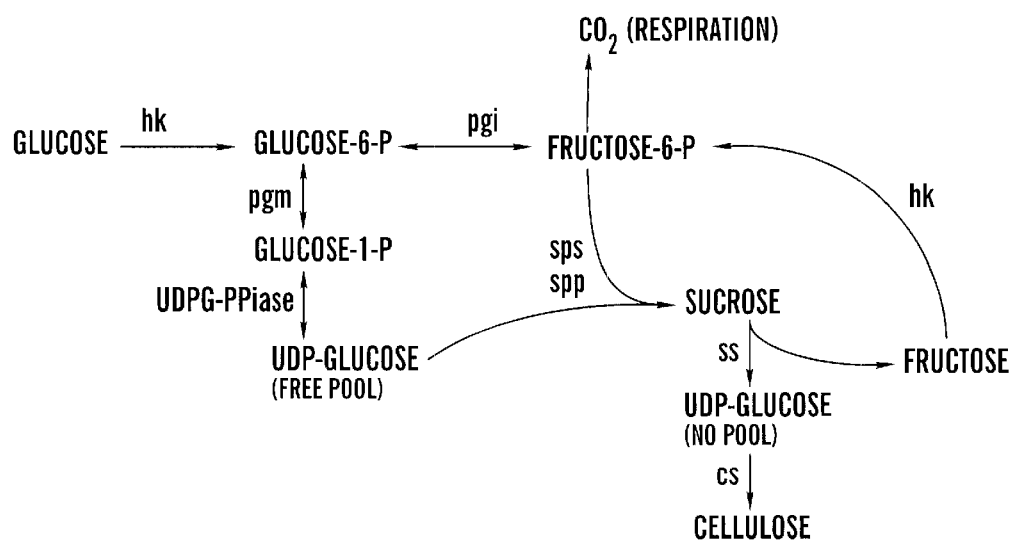
FIG. 2 shows the metabolic pathways and enzymes in sink cells related to the biosynthesis of cellulose.

Tables 2 and 3 show that fiber properties depending on cellulose content, including fiber weight/seed, micronaire, and fiber maturity ratio, increase in transgenic plants when SPS activity is elevated both in the leaves and the fibers. Therefore, with whole-plant analyses, one cannot judge whether these improvements are aided by enhanced export of sucrose from the leaves to the fibers or enhanced synthesis of sucrose in fiber (sink) cells, or both. Since cellulose synthesis has been proposed to use sucrose as an obligatory substrate from which UDP-glucose is generated by the enzyme sucrose synthase, SPS within sink cells can promote metabolic flux toward cellulose by one or both of two mechanisms. SPS could resynthesize sucrose within sink cells because translocated sucrose is cleaved before or soon after entering them, and/or SPS could reuse the fructose released by the activity of sucrose synthase to synthesize more sucrose (FIG. 2).

Evidence that metabolic flux toward cellulose synthesis is enhanced in cellulose-storing sink cells (represented by cotton fibers) by over-expression of SPS was obtained from cotton ovules with attached developing fibers cultured in vitro. Cultured ovules/fibers are a non-photosynthetic system that uses external glucose in plant tissue culture medium as a carbon source to support metabolism required for seed and fiber maturation. Accepting that sucrose is an obligatory substrate for fiber cellulose synthesis, SPS synthesizes sucrose within tissue-cultured ovules/fibers supplied only with glucose. SPS could also reuse the fructose released by the activity of sucrose synthase to synthesize more sucrose. Positive effects of SPS over-expression observed in this system are necessarily independent of photosynthesis. However, the substrate supply in this tissue culture system is constant, implying that it is not possible to exclude enhanced supply of sucrose due to enhanced SPS expression in leaves or decreased starch storage in hypocotyls as also important in improvements observed in whole plants.

Plants yielding the results in Table 7 were flowering in the greenhouse between July and December. Ovules were dissected from flowers and cultured at 34° C. on 1 DPA. The ovules of one flower were split between the 34° C. and 15° C. comparison in each case. Comparison within one flower better controlled the variability that was observed in the rates of cellulose synthesis on 21 DPA between cultures from different flowers of the same plant line. Each test at each temperature included 12–18 ovules split between three replicate dishes. Cultures were shifted from constant 34° C. to a 34/15° C. 12 h/12 h cycle on 18 DPA when secondary wall deposition had commenced. $^{14}$C-glucose was used to label developing ovules and fibers on 21 DPA at 34° C. and 15° C. Therefore, the cultures had 3 days to adjust to exposure to 15° C., and on 21 DPA the 15° C. assay was run 4 h after the shift to 15° C. Cultures of parental C312 treated identically were almost always assayed in parallel with transgenic plant lines.

Rates of respiration ($^{14}CO_2$ evolution) and rates of crystalline cellulose synthesis ($^{14}$C-cellulose remaining insoluble after boiling in acetic/nitric reagent) were determined at both temperatures. Metabolic activity of ovules (seeds) and cotton fibers is combined in the resulting data. However, previous work in which ovules and fibers were separated after the assay was completed demonstrated that under 34/15° C. conditions, 82% of the total cellulose dpm (in ovules+fibers) was attributable to the fibers alone.

From the $^{14}CO_2$ and $^{14}$C-cellulose data, four values were calculated for each plant line: (1) R %—a percentage derived from the 15° C./34° C. ratio of dpm $^{14}CO_2$ trapped on a KOH-soaked filter paper in the incubation chamber; (2) C %—a percentage derived from the 15° C./34° C. ratio of dpm $^{14}$C-cellulose remaining insoluble after boiling in acetic/nitric reagent; (3) $C/R_{15}$—the ratio between dpm $^{14}$C-cellulose and dpm $^{14}CO_2$ at 15° C.; and (4) $C/R_{34}$—the ratio between dpm $^{14}$C-cellulose and dpm $^{14}CO_2$ at 34° C. R % and C % describe the proportion of the 34° C. rate of respiration or cellulose synthesis, respectively, that can be maintained at 15° C. $C/R_{15}$ and $C/R_{34}$ describe the proportion of metabolic flux directed toward cellulose synthesis vs. respiration at 15° C. or 34° C., respectively. Results from parental C312 and 7 transgenic lines tested with good replication in parallel are shown in Table 7 with values considered higher than parental C312 shown in bold.

TABLE 7

Data Calculated From Rates of Cellulose Synthesis and Respiration at 34° C. and 15° C. in in vitro Cultures

| Plant Line | Number of Tests | R % | C % | $C/R_{34}$ | $C/R_{15}$ |
|---|---|---|---|---|---|
| C312-wt | 12 | 17.2 | 21.5 | 2.8 | 3.5 |
| 13-3a* | 6@T2 | 15.3 | 21.8 | 1.8 | 3.0 |
| 38-4a | 7@T2 | 13.0 | 25.7 | 1.9 | 3.9 |
| 40-4b* | 5@T2 | 13.1 | 25.4 | 1.9 | 3.7 |
| 40-6a* | 6@T2 | 15.4 | 20.4 | 2.8 | 3.7 |
| 58-3a | 4@T1 | 14.3 | 25.9 | 3.4 | 6.2 |
| 225-17a* | 4@T1 | 20.9 | 22.6 | 2.8 | 3.1 |
| 619-1a | 7@T1 | 15.9 | 24.9 | 2.9 | 4.6 |

*indicates lines shown in the Phytotron to have improved fiber quality.

The data in Table 7 show that over-expression of SPS reduces R % in 6 of 7 transgenic lines tested in parallel compared to parental C312. This is paralleled by an increase in C % in 5 of 7 transgenic lines tested, meaning that most SPS transgenic lines are able to synthesize cellulose more efficiently at 15° C. than parental C312. Correspondingly, the ratio of cellulose synthesis rate to respiration rate at 15° C. ($C/R_{15}$) increases in 5 of 7 transgenic lines tested. One transgenic line showed an increase in $C/R_{34}$. Transgenic line 13-3a that showed improved fiber quality in the Phytotron did not show improvement in this assay except for reduction of R %. Perhaps this is because secondary wall production proceeds less vigorously in vitro than in planta.

Example 7
Higher Rate of Weight Gain in Sink Cells (Cotton Fibers) During Primary and Secondary Wall Deposition The in vitro ovule/fiber culture system has provided direct evidence that over-expression of SPS in sink cells can lead to higher rates of fiber weight gain at both warm and cool temperatures by mechanisms independent of photosynthesis.

Ovules of transgenic and control C312 were cultured in vitro at constant 34° C. or cycling 34/15° C. from the beginning of culture. Ovules/fibers (8–10 per data point) were harvested from parallel cultures (containing equal representation of 5–8 flowers from at least 3 plants) at intervals during fiber maturation (12–45 DPA). Fibers were stripped from ovules, oven-dried, and weighed. Fiber weight was plotted against time and the slope of weight gain during the period of high-rate secondary wall cellulose synthesis was determined under both temperature regimes. A ratio for the 34/15° C.:34° C. slopes within one plant line was also calculated, which will normalize for any inherent differences in rates of fiber weight gain in cultures of particular lines. For most plant lines tested, several replications of the experiment were conducted at various times allowing average slopes to be compared. A second experiment during a second compressed time interval included 3 complete time-course replications of fiber weight gain in the transgenic plant lines grown in the Phytotron, plus line 38-4a-1. The results of this second experiment, which indicate the repeatability of this assay, are shown as separate italic entries in the table. Values substantially greater than are found in the C312 parental line are highlighted in bold in Table 8.

TABLE 8

Rates of Cellulose Deposition in Fibers Cultured in vitro at 34° C. or 34/15° C.

| Plant Line | 34° C. slope | 34/15° C. slope | Ratio 34/15° C.:34° C. slope |
|---|---|---|---|
| C312-wt | 0.54 | 0.33 | 0.61 |
| C312-wt | 0.52 | 0.31 | 0.60 |
| 13-3a-1* | 0.37 | 0.31 | 0.84 |
| 13-3a-1* | 0.45 | 0.39 | 0.87 |
| 38-4a-1 | 0.45 | 0.25 | 0.56 |
| 40-4b-1* | 0.55 | 0.19 | 0.34 |
| 40-4b-1* | 0.46 | 0.24 | 0.52 |
| -2 | 0.36 | 0.25 | 0.69 |
| -2KS** | 0.38 | 0.26 | 0.68 |
| 40-6a-1 | 0.38 | 0.30 | 0.78 |
| -4 | 0.22 | 0.10 | 0.45 |
| 40-17a-6 | 0.34 | 0.28 | 0.82 |
| 58-3a | 0.42 | 0.41 | 0.98 |
| 178-1a | 0.49 | 0.20 | 0.41 |
| 225-17a* | 0.46 | 0.24 | 0.52 |
| 225-17a* | 0.58 | 0.26 | 0.45 |

TABLE 8-continued

Rates of Cellulose Deposition in Fibers Cultured in vitro at 34° C. or 34/15° C.

| Plant Line | 34° C. slope | 34/15° C. slope | Ratio 34/15° C.:34° C. slope |
|---|---|---|---|
| 414-1a | 0.63 | 0.39 | 0.62 |
| 619-1a | 0.60 | 0.37 | 0.62 |

*Tested at the Phytotron; showing improved fiber quality.
KS**; A kanamycin-sensitive sibling of the kanamycin-resistant plant described immediately above; the kanamycin-sensitive sibling from a population of segregating seeds is expected not to carry a copy of the foreign genes. Note that the slopes from the kanamycin-sensitive and kanamycin-resistant siblings of 40-4b-2 are almost identical, and the differences between these and slopes from the parental C312 cannot be related to expression of the foreign gene.

Line 40-6a and 40-17a are listed together and counted as one line because they likely represent the same transformation event based on derivation from the same parent callus and the same segregation ratio at T1.

Two of the transgenic lines (414-1a and 619-1a) had rates of fiber weight gain at 34° C. higher than parental C312, and several more had higher rates than and the non-SPS-expressing transgenic line, 40-4b-2-KS. Four transgenic lines (13-3a, 58-3a, 414-1a, and 619-1a) had rates of fiber weight gain at 34/15° C. higher than parental C312. Three transgenic lines (13-3a-1, 40-6a-1=40-17a-6, 58-3a) had a ratio for the 34/15° C.:34° C. slopes higher than parental C312 and the non-SPS-expressing transgenic line, 40-4b-2-KS. Lines 414–1 a and 619-la do not stand out in analysis of slope ratios because of greater slopes at both 34° C. and 34/15° C., but these are promising lines for future fiber quality analysis. Some of the lines tested at the Phytotron and shown to have improved fiber quality are superior to parental C312 in this test. The lack of complete consistency may be due to the fact that secondary wall production proceeds less vigorously in vitro than in planta.

From replicated time-courses of fiber weight gain, absolute values of fiber dry weight were also compared at 15 DPA (end of primary wall deposition) and 30 DPA (after extensive secondary wall deposition) in the transgenic plant lines grown in the Phytotron, plus line 38-4a-1. Each data point is the average from three experiments, including fiber from a total of 24–30 ovules representing 15–24 flowers from 4–6 plants per line. The results are shown in Table 9.

TABLE 9

Weights of Fiber (mg/ovule) from in vitro Cultures

| Plant Line | 15 DPA | | | 30 DPA | | |
|---|---|---|---|---|---|---|
| | 34° C. | 34/15° C. | Ratio 34/15° C.:34° C. weights | 34° C. | 34/15° C. | Ratio 34/15° C.:34° C. weights |
| C312-wt | 1.75 | 0.46 | 0.263 | 8.89 | 3.88 | 0.436 |
| 13-3a-1* | 1.94 | 0.60 | 0.309 | 7.33 | 4.64 | 0.633 |
| 38-4a-1 | 1.68 | 0.67 | 0.399 | 8.68 | 3.68 | 0.424 |
| 40-4b-1* | 2.18 | 0.64 | 0.294 | 7.36 | 3.48 | 0.473 |
| 225-17a* | 1.84 | 0.59 | 0.320 | 8.80 | 3.72 | 0.423 |

*Tested at the Phytotron; showing improved fiber quality.

At 15 DPA, four transgenic lines show consistently greater weight gain than parental C312 under 34/15° C., and three of the four transgenic lines show greater weight gain under constant 34° C. The ratio of 34/15° C. to 34° C. weights is greater in all four transgenic lines, demonstrating improved fiber production in SPS transgenic plants under adverse cool temperatures by mechanisms independent of photosynthesis. At 15 DPA, fiber dry weight is composed mostly of primary walls, and greater fiber weight could be due to greater fiber length or greater primary wall thickness, or both.

At 30 DPA, one transgenic line shows greater fiber weight gain than parental C312 under 34/15° C. Two transgenic lines show greater ratio of 34/15° C. to 34° C. weights. Fiber dry weight at 30 DPA is largely cellulose. Therefore, SPS over-expression within transgenic fibers promotes cellulose deposition, including its deposition under adverse cool temperatures. The inconsistency of results for transgenic lines at 30 DPA is likely explained by the fact that secondary wall deposition in vitro is more hindered than fiber lengthening. However, all the transgenic lines tested in the Phytotron and showing improved fiber quality show some improvement in this in vitro test.

Example 8
Enhanced Stem Weight of Transgenic Cotton Plants

The positive effects of SPS over-expression on cellulose synthesis in cotton fibers extends to other fibers. Fibers make up most of the weight of annual or perennial strong stems, such as are found in mature cotton plants. Therefore, the stem weight of cotton plants grown in the Phytotron and the Texas Tech greenhouse was determined (Table 10). The conditions of the Texas Tech greenhouse were most similar to the Phytotron 30/15° C., 360 ppm $CO_2$ chamber.

In the Phytotron, time of stem weight determination varied somewhat between plant lines for the 30/28° C. chambers because each plant was harvested shortly after all bolls on it had opened. For the 30/15° C. condition, plant growth was terminated at the same time when some immature bolls remained on all plants. All plants were 6–7 months old at time of harvest. In the Texas Tech greenhouse, parental and transgenic plants were randomized on two adjacent tables and grown for 30 weeks before simultaneous harvesting. Main stem diameter and height were also determined in the greenhouse plants.

In the Phytotron, stem weight increased by 10% or more in transgenic plants compared to parental C312 in 11 of 15 cases (representing the matrix of plant lines x chambers tested). The increases are particularly pronounced and consistent across three chambers for line 40-6a-4, although there were few replicate plants in the Phytotron for this line. Therefore, line 40-6a-4-3 was tested at the next generation (T3) in the Texas Tech greenhouse with more replication in parallel with parental C312 and another transgenic line, 357–6a- 1 at T2. Line 40-6a-4-3 again showed average increased stem weight with a similar magnitude of change as observed in the Phytotron chambers at 30/15° C. and both 360 and 700 ppm $CO_2$. In addition, line 40-6a-4-3 showed average increased stem height and stem diameter compared to parental C312 and the transgenic line 357–6a-1, which was smaller than C312. Therefore, transgenic lines do not all show increased stem weight, probably because of differences in tissue-specific gene expression. Considering the main plant stem, excluding branches that were also weighed, as a right cone with volume=$\pi^2 h/3$, line 40-6a-4-3 would have increased volume of 1.31 times compared to parental C312. The similarity of this to the observed weight increase of 1.27 times suggests that much of the weight increase is-

TABLE 10

Normalized Values for Stem Weight, Diameter, and Height
(Average values for transgenic plants are normalized to the corresponding value for the Coker 312 wild-type parent set to 1.00.)

| | Phytotron Test | | | | | Greenhouse Test | | | |
|---|---|---|---|---|---|---|---|---|---|
| Plant Line | Phytotron Plants (n) per chamber, in order | Stem Weight 30/15° C. $CO_2$ = 360 | Stem Weight 30/15° C. $CO_2$ = 700 | Stem Weight 30/28° C. $CO_2$ = 360 | Stem Weight 30/28° C. $CO_2$ = 700 | Green House Plants (n) | Stem Weight | Stem Diameter | Stem Height |
| C312-wt 13-3a | 4,4,4,4 | 1.00 | 1.00 | 1.00 | 1.00 | 6 | 1.00 | 1.00 | 1.00 |
| T1#1 @ T2 225-17a | 4,4,4,4 | 1.12 | 1.20 | 1.03 | 1.11 | | | | |
| T1 40-4b | 4,4,4,4 | 0.95 | 1.11 | 1.28 | 1.07 | | | | |
| T1#1 & #4 @ T2 40-6a | 5,5,7,5 | 0.81 | 1.12 | 1.22 | 1.13 | | | | |
| T1#4 @ T2 T2-4-3 @ T3 357-6a | 1,1,2,0 | 1.33 | 1.30 | 1.82 | — | 5 | 1.27 | 1.11 | 1.06 |
| T1#1 @ T2 | | | | | | 6 | 0.92 | 0.93 | 0.94 | associated with increased volume of the main stem containing abundant fibers. The 4% difference between the theoretical prediction and the observation could be due to different degrees of branching or changes in stem density that have not been determined.

Example 9
Increased Stem Diameter in Multiple Lines of Transgenic Cotton

In addition to line 40-6a, some stems appeared bigger than others among transgenic cotton plants growing in the greenhouse. However, these plants were of different ages. To try to quantitate this observation, electronic calipers were used to measure stem diameter approximately two inches above the soil line in all plants in the greenhouse on Sep. 23, 1998 (which did not include all the plants of interest implicated by previous studies). Date of planting was also recorded for each plant measured. By analyzing values for the Coker 312 parent and transgenic line 58-3a(2) (T1 individuals, number 1–7) that had plants of several ages in the greenhouse, the following approximate values for rate of stem diameter increase per day were estimated. The rate decreases with time because, in the 2 gallon pots used for planting, stem diameter in parental C312 plants apparently slows or stops increasing at about 5 months.

| Plant Age | Rate of Stem Diameter Increase |
|---|---|
| <150 days | 0.13 mm/day |
| 160–200 days | 0.10 mm/day |
| >210 days | 0.06 mm/day |

Of 12 independent transgenic lines analyzed (each with several replicate pots), six had average values greater than the standards established for parental C312 (or at the upper end of the range) (Table 11). Transgenic lines that did not show increased rates of stem diameter increase may express spinach SPS less strongly in their stems.

TABLE 11

Transgenic Plant Lines with Enhanced Rates of Stem Diameter Increase in the Greehouse

| Plant Line | Plant Age (days) | Rate of Stem Diameter Increase (mm/day) |
|---|---|---|
| 40-4b-2-7 | 216 | 0.076 |
| 40-6a-4-2 | 180 | 0.124 |
| -3,4 | 215 | 0.107 |
| 58-3a-3 | 214 | 0.078 |
| 414-1a-1,2 | 193 | 0.086 |
| 530-1a-2,3 | 197 | 0.095 |
| 619-1a-6 | 153 | 0.140 |

Note that Table 10 confirms through a second experiment the increased rate of stem diameter increase for line 40-6a-4-3. Increased stem diameter depends on more cellulose-containing fiber within the stem. Larger stem diameter at the end of a growing period could be explained by faster rate of diameter increase or longer persistence of diameter increase in one growing season. Either case will result in more harvestable stem fiber.

Example 10
Enhanced Conversion of Atmospheric $CO_2$ into Harvestable Crops, Preferentially Cellulose-based Fiber As shown in Table 12, comparison of data between the 30/15° C. Phytotron chambers with 360 and 700 ppm $CO_2$ demonstrates that SPS transgenic plants convert normal levels of $CO_2$ more efficiently into cellulose-based cotton fiber. At normal levels of $CO_2$, SPS transgenic plants are able to more nearly reach their maximum possible fiber production potential (as shown by comparative changes in Lint Fiber Weight per Seed) so that raising $CO_2$ to 700 ppm increases their fiber wall thickness less than parental C312 (as shown by comparative changes in Micronaire). However, when stem weight is considered as an indication of production potential for all types of fiber, transgenic plants remain superior to parental C312 at 30/15° C. even under elevated $CO_2$. In contrast, raising $CO_2$ levels at 30/15° C. tended to decrease seed weight in transgenics and parental C312 (although transgenic seed weight always remained higher than in parental C312—see Example 2).

Therefore, over-expression of SPS has a preferential effect on cotton fiber production probably due to increasing sink demand of this cellulose-based sink. SPS over-expression in fiber can, as previously demonstrated, preferentially increase metabolic flux toward cellulose and fiber weight gain. Data supporting these conclusions are shown in Table 12, which shows the percentage change in values of various parameters when $CO_2$ was increased from 300 to 700 ppm under 30/15° C. in the Phytotron.

TABLE 12

Percentage Change in Various Crop-Related Attributes With Increase from 300 to 700 ppm $CO_2$ at 30/15° C.

| Plant Line | Micronaire | Lint Fiber Weight per Seed | Fuzzy Seed Weight per Seed | Ratio of Fiber to Fuzzy Seed Weight | Stem Weight |
|---|---|---|---|---|---|
| C312-wt | +9% | +35% | -8% | +48% | +22% |
| 13-3a-1@T2 | +2% | +10% | -6% | +18% | +31% |
| 225-17a@T1 | -18% | -5% | -14% | +12% | +42% |
| 40-4b-1,4@T2 | +7% | +25% | 0% | +24% | +71% |
| Transgenic Average | -3% | +10% | -7% | +18% | +48% |

Fiber crops that over-express SPS can convert normal $CO_2$ more efficiently into economically valuable fiber. Such plants grown widely as crops should help to combat rising $CO_2$ levels in the atmosphere because they immobilize $CO_2$ into fiber cellulose with improved efficiency under normal $CO_2$ levels, and this efficiency of production is maintained (for cotton fiber) or enhanced (for stem fiber) under elevated $CO_2$ levels.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A transgenic cotton plant comprising a chimeric DNA construct comprising a plant specific promoter and a DNA encoding a sucrose phosphate synthase, whereby the transgenic cotton plant has an increased level of sucrose phosphate synthase relative to a non-transgenic cotton plant and wherein cotton fibers from the plant have improved quality, said improved quality being selected from the group consisting of increased strength, increased length, increased fiber fineness, increased fiber maturity ratio, decreased immature fiber content, increased fiber uniformity, and increased micronaire, compared to a cotton plant lacking the chimeric DNA construct.

2. The transgenic cotton plant according to claim 1, wherein the chimeric DNA construct is stably integrated into the genome of the cotton plant.

3. The transgenic cotton plant according to claim 1, wherein the chimeric DNA construct is introduced into the cotton plant by a method selected from the group consisting of electroporation, Agrobacterium mediated transformation, biolistic gene transformation, chemically mediated transformation, and microinjection.

4. The transgenic cotton plant according to claim 1, wherein the DNA encoding the sucrose phosphate synthase is from a plant selected from the group consisting of spinach, Arabidopsis, beet, bean, citrus, maize, moss, potato, rice, sugar cane, and Synechocystis.

5. The transgenic cotton plant according to claim 4, wherein the DNA encoding the sucrose phosphate synthase is from spinach.

6. Transgenic seed produced from the plant according to claim 1.

7. A method of improving the quality of cotton fiber produced from a cotton plant, said method comprising:
   introducing into a cotton plant a chimeric DNA construct comprising a plant specific transcription initiation region and a DNA encoding a sucrose phosphate synthase which, when introduced into cells of said cotton plant increases sucrose phosphate synthase activity in an amount sufficient to improve the quality of the cotton fiber produced by the cotton plant, wherein the improved quality is selected from the group consisting of increased strength, increased length, increased fiber fineness, increased fiber maturity ratio, decreased immature fiber content, increased fiber uniformity, and increased micronaire, compared to a cotton plant lacking the chimeric DNA construct.

8. The method according to claim 7, further comprising: growing said cotton plant.

9. The method according to claim 7, wherein the DNA encoding sucrose phosphate synthase is from a plant selected from the group consisting of spinach, Arabidopsis, beet, bean, citrus, maize, moss, potato, rice, sugar cane, and Synechocystis.

10. The method according to claim 9, wherein the DNA encoding the sucrose phosphate synthase is from spinach.

11. The method according to claim 7, wherein the transcription initiation region is cotton fiber specific.

12. The method according to claim 7, wherein the transcription initiation region is a 35S promoter, a dual S35 promoter, an FMV promoter, or a cotton fiber-enhanced promoter of a cotton fiber-expressed gene selected from the group consisting of E6, H6, FbL2A, rac, CelA, CAP, ACP, and LTP.

13. The method according to claim 7, wherein the chimeric DNA construct is stably integrated into the genome of the cotton plant.

14. The method according to claim 7, wherein said introducing of the chimeric DNA construct into the plant is carried out by a method selected from the group consisting of electroporation, Agrobacterium mediated transformation, biolistic gene transformation, chemically mediated transformation, and microinjection.

15. A method of altering the quality of fiber isolated from a cotton plant by altering the expression of sucrose phosphate synthase in the plant, said method comprising:
  introducing into a cotton plant a chimeric DNA construct comprising a DNA encoding a sucrose phosphate synthase which, when introduced into cells of said plant, increases sucrose phosphate synthase activity in an amount sufficient to alter the quality of fiber produced from the plant, wherein the altered fiber quality is selected from the group consisting of strength, length, fineness, maturity ratio, immature fiber content, uniformity, and micronaire, compared to a cotton plant lacking the chimeric DNA construct.

16. A method of altering the quality of fiber isolated from a cotton plant by decreasing the expression of sucrose phosphate synthase in the plant, said method comprising:
  introducing into a cotton plant a chimeric DNA construct comprising an antisense DNA encoding a nucleic acid molecule complementary to a sense DNA encoding sucrose phosphate synthase which, when introduced into cells of said plant, decreases sucrose phosphate synthase activity in an amount sufficient to alter the quality of fiber produced from the plant, wherein the altered fiber quality is selected from the group consisting of decreased strength, decreased length, and decreased weight per unit length, as compared to a cotton plant lacking the chimeric DNA construct.

* * * * *

SEQUENCE LISTING

<160> NUMBER OF SEQ ID NOS: 14

<210> SEQ ID NO 1
<211> LENGTH: 1056
<212> TYPE: PRT
<213> ORGANISM: Spinacia oleracea

<400> SEQUENCE: 1

```
Met Ala Gly Asn Asp Trp Ile Asn Ser Tyr Leu Glu Ala Ile Leu Asp
 1               5                  10                  15

Val Gly Gly Gln Gly Ile Asp Ala Ser Thr Gly Lys Thr Ser Thr Ala
            20                  25                  30

Pro Pro Ser Leu Leu Arg Glu Arg Gly His Phe Ser Pro Ser Arg
        35                  40                  45

Tyr Phe Val Glu Val Ile Ser Gly Phe Asp Glu Thr Asp Leu His
    50                  55                  60

Arg Ser Trp Val Arg Ala Ala Ser Thr Arg Ser Pro Gln Glu Arg Asn
 65                  70                  75                  80

Thr Arg Leu Glu Asn Leu Cys Trp Arg Ile Trp Asn Leu Ala Arg Lys
                85                  90                  95

Lys Lys Gln Ile Glu Gly Glu Glu Ala Gln Arg Leu Ala Lys Arg His
            100                 105                 110

Val Glu Arg Glu Arg Gly Arg Arg Glu Ala Thr Ala Asp Met Ser Glu
        115                 120                 125

Asp Leu Ser Glu Gly Glu Arg Gly Asp Thr Val Ala Asp Met Leu Phe
    130                 135                 140

Ala Ser Glu Ser Thr Lys Gly Arg Met Arg Arg Ile Ser Ser Val Glu
145                 150                 155                 160

Met Met Asp Asn Trp Ala Asn Thr Phe Lys Glu Lys Lys Leu Tyr Val
                165                 170                 175

Val Leu Ile Ser Leu His Gly Leu Ile Arg Gly Glu Asn Met Glu Leu
            180                 185                 190

Gly Arg Asp Ser Asp Thr Gly Gly Gln Val Lys Tyr Val Val Glu Leu
        195                 200                 205

Ala Arg Ala Leu Gly Ser Met Pro Gly Val Tyr Arg Val Asp Leu Leu
    210                 215                 220

Thr Arg Gln Val Ser Ala Pro Gly Val Asp Trp Ser Tyr Gly Glu Pro
225                 230                 235                 240

Thr Glu Met Leu Ser Ser Arg Asn Ser Glu Asn Ser Thr Glu Gln Leu
                245                 250                 255

Gly Glu Ser Ser Gly Ala Tyr Ile Ile Arg Ile Pro Phe Gly Pro Lys
            260                 265                 270

Asp Lys Tyr Val Ala Lys Glu Leu Leu Trp Pro Tyr Ile Pro Glu Phe
        275                 280                 285

Val Asp Gly Ala Leu Ser His Ile Lys Gln Met Ser Lys Val Leu Gly
    290                 295                 300

Glu Gln Ile Gly Gly Gly Leu Pro Val Trp Pro Ala Ser Val His Gly
305                 310                 315                 320

His Tyr Ala Asp Ala Gly Asp Ser Ala Ala Leu Leu Ser Gly Ala Leu
                325                 330                 335

Asn Val Pro Met Val Phe Thr Gly His Ser Leu Gly Arg Asp Lys Leu
            340                 345                 350

Asp Gln Leu Leu Lys Gln Gly Arg Leu Ser Arg Glu Glu Val Asp Ala
```

-continued

```
                355                 360                 365
Thr Tyr Lys Ile Met Arg Arg Ile Glu Ala Glu Glu Leu Cys Leu Asp
    370                 375                 380
Ala Ser Glu Ile Val Ile Thr Ser Thr Arg Gln Glu Ile Glu Glu Gln
385                 390                 395                 400
Trp Gln Leu Tyr His Gly Phe Asp Leu Val Leu Glu Arg Lys Leu Arg
                405                 410                 415
Ala Arg Met Arg Arg Gly Val Ser Cys His Gly Arg Phe Met Pro Arg
            420                 425                 430
Met Ala Lys Ile Pro Pro Gly Met Glu Phe Asn His Ile Ala Pro Glu
        435                 440                 445
Asp Ala Asp Met Asp Thr Asp Ile Asp Gly His Lys Glu Ser Asn Ala
    450                 455                 460
Asn Pro Asp Pro Val Ile Trp Ser Glu Ile Met Arg Phe Phe Ser Asn
465                 470                 475                 480
Gly Arg Lys Pro Met Ile Leu Ala Leu Ala Arg Pro Asp Pro Lys Lys
                485                 490                 495
Asn Leu Thr Thr Leu Val Lys Ala Phe Gly Glu Cys Arg Pro Leu Arg
            500                 505                 510
Glu Leu Ala Asn Leu Thr Leu Ile Ile Gly Asn Arg Asp Asp Ile Asp
        515                 520                 525
Glu Met Ser Thr Thr Ser Ser Ser Val Leu Ile Ser Ile Leu Lys Leu
    530                 535                 540
Ile Asp Lys Tyr Asp Leu Tyr Gly Gln Val Ala Tyr Pro Lys His His
545                 550                 555                 560
Lys Gln Ser Asp Val Pro Asp Ile Tyr Arg Leu Ala Ala Lys Thr Lys
                565                 570                 575
Gly Val Phe Ile Asn Pro Ala Phe Ile Glu Pro Phe Gly Leu Thr Leu
            580                 585                 590
Ile Glu Ala Ala Ala Tyr Gly Leu Pro Ile Val Ala Thr Lys Asn Gly
        595                 600                 605
Gly Pro Val Asp Ile Ile Gly Val Leu Asp Asn Gly Leu Leu Ile Asp
    610                 615                 620
Pro His Asp Gln Lys Ser Ile Ala Asp Ala Leu Leu Lys Leu Val Ala
625                 630                 635                 640
Asp Lys His Leu Trp Thr Lys Cys Arg Gln Asn Gly Leu Lys Asn Ile
                645                 650                 655
His Leu Phe Ser Trp Pro Glu His Cys Lys Asn Tyr Leu Ser Arg Ile
            660                 665                 670
Ala Ser Cys Lys Pro Arg Gln Pro Asn Trp Gln Arg Ile Asp Glu Gly
        675                 680                 685
Ser Glu Asn Ser Asp Thr Asp Ser Ala Gly Asp Ser Leu Arg Asp Ile
    690                 695                 700
Gln Asp Ile Ser Leu Asn Leu Lys Leu Ser Leu Asp Ala Glu Arg Thr
705                 710                 715                 720
Glu Gly Gly Asn Ser Phe Asp Asp Ser Leu Asp Ser Glu Glu Ala Asn
                725                 730                 735
Ala Lys Arg Lys Ile Glu Asn Ala Val Ala Lys Leu Ser Lys Ser Met
            740                 745                 750
Asp Lys Ala Gln Val Asp Val Gly Asn Leu Lys Phe Pro Ala Ile Arg
        755                 760                 765
Arg Arg Lys Cys Ile Phe Val Ile Ala Leu Asp Cys Asp Val Thr Ser
    770                 775                 780
```

```
Asp Leu Leu Gln Val Ile Lys Thr Val Ile Ser Ile Val Gly Glu Gln
785                 790                 795                 800

Arg Pro Thr Gly Ser Ile Gly Phe Ile Leu Ser Thr Ser Met Thr Leu
                805                 810                 815

Ser Glu Val Asp Ser Leu Leu Asp Ser Gly Gly Leu Arg Pro Ala Asp
            820                 825                 830

Phe Asp Ala Phe Ile Cys Asn Ser Gly Ser Glu Leu Tyr Tyr Pro Ser
        835                 840                 845

Thr Asp Tyr Ser Glu Ser Pro Phe Val Leu Asp Gln Asp Tyr Tyr Ser
    850                 855                 860

His Ile Asp Tyr Arg Trp Gly Gly Gly Leu Trp Lys Thr Leu Val
865                 870                 875                 880

Lys Trp Ala Ala Ser Val Asn Glu Lys Lys Gly Glu Asn Ala Pro Asn
                885                 890                 895

Ile Val Ile Ala Asp Glu Thr Ser Thr Thr His Cys Tyr Ala Phe
            900                 905                 910

Lys Val Asn Asp Phe Thr Leu Ala Pro Pro Ala Lys Glu Leu Arg Lys
        915                 920                 925

Met Met Arg Ile Gln Ala Leu Arg Cys His Ala Ile Tyr Cys Gln Asn
    930                 935                 940

Gly Thr Arg Leu Asn Val Ile Pro Val Leu Ala Ser Arg Ser Gln Ala
945                 950                 955                 960

Leu Arg Tyr Leu Phe Met Arg Trp Gly Val Glu Leu Ser Asn Phe Val
                965                 970                 975

Val Phe Val Gly Glu Ser Gly Asp Thr Asp Tyr Glu Gly Leu Leu Gly
            980                 985                 990

Gly Val His Lys Thr Val Ile Leu Lys Gly Ile Gly Ser Asn Thr Ser
        995                 1000                1005

Asn Phe His Ala Thr Arg Ala Tyr Pro Met Glu His Val Met Pro Val
    1010                1015                1020

Asp Ser Pro Asn Met Phe Gln Thr Gly Gly Cys Asn Ile Asp Asp Ile
1025                1030                1035                1040

Ser Asp Ala Leu Ser Lys Ile Gly Cys Leu Lys Ala Gln Lys Ser Leu
                1045                1050                1055

<210> SEQ ID NO 2
<211> LENGTH: 1057
<212> TYPE: PRT
<213> ORGANISM: Citrus unshiu

<400> SEQUENCE: 2

Met Ala Gly Asn Asp Trp Ile Asn Ser Tyr Leu Glu Ala Ile Leu Asp
1               5                   10                  15

Val Gly Pro Gly Leu Asp Asp Ala Lys Ser Ser Leu Leu Leu Arg Glu
            20                  25                  30

Arg Gly Arg Phe Ser Pro Thr Arg Tyr Phe Val Glu Glu Val Ile Thr
        35                  40                  45

Gly Phe Asp Glu Thr Asp Leu His Arg Ser Trp Val Lys Ala Gln Ala
    50                  55                  60

Thr Arg Ser Pro Gln Glu Arg Asn Thr Arg Leu Glu Asn Met Cys Trp
65                  70                  75                  80

Arg Ile Trp Asn Leu Ala Arg Gln Lys Lys Gln Leu Glu Gly Glu Ala
                85                  90                  95

Ala Gln Arg Met Ala Lys Arg Arg Leu Glu Arg Glu Arg Gly Arg Arg
```

-continued

```
                100                 105                 110
Glu Ala Thr Ala Asp Met Ser Glu Asp Leu Ser Glu Gly Lys Gly
            115                 120                 125
Asp Ile Val Ser Asp Val Ser Ala His Gly Asp Ser Thr Arg Ser Arg
130                 135                 140
Leu Pro Arg Ile Ser Ser Val Asp Ala Met Glu Thr Trp Ile Ser Gln
145                 150                 155                 160
Gln Lys Gly Lys Lys Leu Tyr Ile Val Leu Ile Ser Ile His Gly Leu
                165                 170                 175
Ile Arg Gly Glu Asn Met Glu Leu Gly Arg Asp Ser Asp Thr Gly Gly
            180                 185                 190
Gln Val Lys Tyr Val Val Glu Leu Ala Arg Ala Leu Gly Ser Met Pro
            195                 200                 205
Gly Val Tyr Arg Val Asp Leu Leu Thr Arg Gln Val Ser Ala Pro Asp
        210                 215                 220
Val Asp Trp Ser Tyr Gly Glu Pro Thr Glu Met Leu Thr Pro Arg Asn
225                 230                 235                 240
Ser Asp Asp Phe Met Asp Met Gly Glu Ser Ser Gly Ala Tyr Ile
                245                 250                 255
Ile Arg Ile Pro Phe Gly Pro Lys Asp Lys Tyr Ile Ala Lys Glu Leu
            260                 265                 270
Leu Trp Pro His Ile Pro Glu Phe Val Asp Gly Ala Leu Asn His Ile
        275                 280                 285
Ile Arg Met Ser Asn Val Leu Gly Glu Gln Ile Gly Gly Lys Pro
        290                 295                 300
Val Trp Pro Val Ala Ile His Gly His Tyr Ala Asp Ala Gly Asp Ser
305                 310                 315                 320
Ala Ala Leu Leu Ser Gly Ala Leu Asn Val Pro Met Leu Phe Thr Gly
                325                 330                 335
His Ser Leu Gly Arg Asp Lys Leu Glu Gln Leu Leu Lys Gln Ala Arg
            340                 345                 350
Leu Ser Arg Asp Glu Ile Asn Ala Thr Tyr Lys Ile Met Arg Arg Ile
        355                 360                 365
Glu Ala Glu Leu Ser Leu Asp Ala Ser Glu Ile Val Ile Thr Ser
        370                 375                 380
Thr Arg Gln Glu Ile Glu Glu Gln Trp Arg Leu Tyr Asp Gly Phe Asp
385                 390                 395                 400
Pro Val Leu Glu Arg Lys Leu Arg Ala Arg Ile Lys Arg Asn Val Ser
                405                 410                 415
Cys Tyr Gly Lys Phe Met Pro Arg Met Ala Ile Ile Pro Pro Gly Met
            420                 425                 430
Glu Phe His His Ile Val Pro Gln Asp Gly Asp Met Asp Gly Glu Thr
        435                 440                 445
Glu Gly Asn Glu Asp Asn Pro Ala Ser Pro Asp Pro Ile Trp Ser
        450                 455                 460
Glu Ile Met Arg Phe Phe Thr Asn Pro Arg Lys Pro Val Ile Leu Ala
465                 470                 475                 480
Leu Ala Arg Pro Asp Pro Lys Lys Asn Ile Thr Thr Leu Val Lys Ala
                485                 490                 495
Phe Gly Glu Cys Arg Pro Leu Arg Glu Leu Ala Asn Leu Thr Leu Ile
            500                 505                 510
Met Gly Asn Arg Asp Gly Ile Asp Glu Met Ser Ser Thr Ser Ala Ser
            515                 520                 525
```

-continued

```
Val Leu Leu Ser Val Leu Lys Leu Ile Asp Lys Tyr Asp Leu Tyr Gly
            530                 535                 540
Gln Val Ala Tyr Pro Lys His His Lys Gln Ser Asp Val Pro Glu Ile
545                 550                 555                 560
Tyr Arg Leu Ala Ala Lys Thr Lys Gly Val Phe Ile Asn Pro Ala Phe
                565                 570                 575
Ile Glu Pro Phe Gly Leu Thr Leu Ile Glu Ala Ala His Gly Leu
            580                 585                 590
Pro Ile Val Ala Thr Lys Asn Gly Gly Pro Val Asp Ile His Arg Val
            595                 600                 605
Leu Asp Asn Gly Leu Leu Val Asp Pro His Asp Gln Gln Ser Ile Ala
            610                 615                 620
Asp Ala Leu Leu Lys Leu Val Ala Gly Lys Gln Leu Trp Ala Arg Cys
625                 630                 635                 640
Arg Gln Asn Gly Leu Lys Asn Ile His Leu Phe Ser Trp Pro Glu His
                645                 650                 655
Cys Lys Thr Tyr Leu Ser Arg Ile Ala Gly Cys Lys Pro Arg His Pro
            660                 665                 670
Gln Trp Gln Arg Thr Asp Asp Gly Gly Glu Thr Ser Glu Ser Asp Ser
            675                 680                 685
Pro Gly Asp Ser Leu Arg Asp Ile Gln Asp Ile Ser Leu Asn Leu Lys
            690                 695                 700
Phe Ser Leu Asp Gly Glu Lys Ser Gly Ala Ser Gly Asn Asp Asp Ser
705                 710                 715                 720
Leu Asp Ser Glu Gly Asn Val Ala Asp Arg Lys Ser Arg Leu Glu Asn
                725                 730                 735
Ala Val Leu Ala Trp Ser Lys Gly Val Leu Lys Asp Thr Arg Lys Ser
            740                 745                 750
Gly Ser Thr Asp Lys Val Asp Gln Asn Thr Gly Ala Ala Lys Phe Pro
            755                 760                 765
Ala Leu Arg Arg Arg Lys His Ile Phe Val Ile Ser Val Asp Cys Asp
            770                 775                 780
Ser Thr Thr Gly Leu Leu Asp Ala Thr Lys Lys Ile Cys Glu Ala Val
785                 790                 795                 800
Glu Lys Glu Arg Thr Glu Gly Ser Ile Gly Phe Ile Leu Ser Thr Ser
                805                 810                 815
Met Thr Ile Ser Glu Ile His Ser Phe Leu Val Ser Gly His Leu Ser
            820                 825                 830
Pro Ser Asp Phe Asp Ala Phe Ile Cys Asn Ser Gly Ser Asp Leu Tyr
            835                 840                 845
Tyr Ser Thr Leu Asn Ser Glu Asp Gly Pro Phe Val Val Asp Phe Tyr
            850                 855                 860
Tyr His Ser His Ile Glu Tyr Arg Trp Gly Gly Glu Gly Leu Arg Lys
865                 870                 875                 880
Thr Leu Val Arg Trp Ala Ser Gln Val Thr Asp Lys Lys Ala Glu Ser
                885                 890                 895
Gly Glu Lys Val Leu Thr Pro Ala Glu Gln Leu Ser Thr Asn Tyr Cys
            900                 905                 910
Tyr Ala Phe Ser Val Gln Lys Pro Gly Met Thr Pro Pro Val Lys Glu
            915                 920                 925
Leu Arg Lys Val Leu Arg Ile Gln Ala Leu Arg Cys His Val Ile Tyr
            930                 935                 940
```

-continued

```
Cys Gln Asn Gly Ser Arg Val Asn Val Ile Pro Val Leu Ala Ser Arg
945                 950                 955                 960

Ser Gln Ala Leu Arg Tyr Leu Tyr Leu Arg Trp Gly Val Glu Leu Ser
            965                 970                 975

Lys Met Val Val Phe Val Gly Glu Ser Gly Asp Thr Asp Tyr Glu Gly
            980                 985                 990

Leu Leu Gly Gly Val His Lys Thr Val Ile Leu Lys Gly Ile Cys Ser
        995                 1000                1005

Ser Ser Ser Asn Gln Ile His Ala Asn Arg Ser Tyr Pro Leu Ser Asp
    1010                1015                1020

Val Met Pro Ile Asp Ser Pro Asn Ile Val Gln Thr Pro Glu Asp Cys
1025                1030                1035                1040

Thr Thr Ser Asp Ile Arg Ser Ser Leu Glu Gln Leu Gly Leu Leu Lys
            1045                1050                1055

Val

<210> SEQ ID NO 3
<211> LENGTH: 1054
<212> TYPE: PRT
<213> ORGANISM: Craterostigma plantagineum

<400> SEQUENCE: 3

Met Ala Gly Asn Asp Trp Ile Asn Ser Tyr Leu Glu Ala Ile Leu Asp
1               5                   10                  15

Val Gly Pro Gly Ile Asp Glu Ala Lys Gly Ser Leu Leu Leu Arg Glu
            20                  25                  30

Arg Gly Arg Phe Ser Pro Thr Arg Tyr Phe Val Glu Glu Val Val Ser
        35                  40                  45

Gly Phe Asp Glu Thr Asp Leu His Arg Ser Trp Ile Arg Ala Gln Ala
    50                  55                  60

Thr Arg Ser Pro Gln Glu Arg Asn Thr Arg Leu Glu Asn Met Cys Trp
65                  70                  75                  80

Arg Ile Trp Asn Leu Ala Arg Gln Lys Lys Gln Leu Glu Asn Glu Glu
                85                  90                  95

Ala Gln Arg Met Ala Lys Arg Leu Glu Arg Glu Arg Gly Arg Arg
            100                 105                 110

Glu Ala Val Ala Asp Met Ser Glu Asp Leu Ser Glu Gly Glu Lys Gly
        115                 120                 125

Asp Ile Val Val Asp His Ser His His Gly Glu Ser Asn Arg Gly Arg
    130                 135                 140

Leu Pro Arg Ile Asn Ser Val Asp Thr Met Glu Ala Trp Met Asn Gln
145                 150                 155                 160

Gln Lys Gly Lys Lys Leu Tyr Ile Val Leu Ile Ser Leu His Gly Leu
                165                 170                 175

Ile Arg Gly Glu Asn Met Glu Leu Gly Arg Asp Ser Asp Thr Gly Gly
            180                 185                 190

Gln Val Lys Tyr Val Val Glu Leu Ala Arg Ala Leu Gly Ser Met Pro
        195                 200                 205

Gly Val Tyr Arg Val Asp Leu Leu Thr Arg Gln Val Ser Ser Pro Glu
    210                 215                 220

Val Asp Trp Ser Tyr Gly Glu Pro Thr Glu Met Leu Pro Pro Arg Asn
225                 230                 235                 240

Ser Glu Asn Met Met Asp Glu Met Gly Glu Ser Ser Gly Ser Tyr Ile
                245                 250                 255
```

```
Val Arg Ile Pro Phe Gly Pro Lys Asp Lys Tyr Val Ala Lys Glu Leu
            260                 265                 270

Leu Trp Pro His Ile Pro Glu Phe Val Asp Gly Ala Leu Gly His Ile
            275                 280                 285

Ile Gln Met Ser Lys Val Leu Gly Glu Gln Ile Gly Asn Gly His Pro
            290                 295                 300

Ile Trp Pro Ala Ala Ile His Gly His Tyr Ala Asp Ala Gly Asp Ser
305                 310                 315                 320

Ala Ala Leu Leu Ser Gly Ala Leu Asn Val Pro Met Leu Phe Thr Gly
                325                 330                 335

His Ser Leu Gly Arg Asp Lys Leu Glu Gln Leu Leu Arg Gln Gly Arg
            340                 345                 350

Leu Ser Arg Asp Glu Ile Asn Ser Thr Tyr Lys Ile Met Arg Arg Ile
            355                 360                 365

Glu Ala Glu Glu Leu Ser Leu Asp Ala Ser Glu Met Val Ile Thr Ser
            370                 375                 380

Thr Arg Gln Glu Ile Glu Glu Gln Trp Arg Leu Tyr Asp Gly Phe Asp
385                 390                 395                 400

Pro Ile Leu Glu Arg Lys Leu Arg Ala Arg Ile Lys Arg Asn Val Ser
            405                 410                 415

Cys Tyr Gly Arg Phe Met Pro Arg Met Met Val Ile Pro Pro Gly Met
            420                 425                 430

Glu Phe His His Ile Val Pro His Asp Gly Asp Leu Asp Ala Glu Pro
            435                 440                 445

Glu Phe Asn Glu Asp Ser Lys Ser Pro Asp Pro His Ile Trp Thr Glu
            450                 455                 460

Ile Met Arg Phe Phe Ser Asn Pro Arg Lys Pro Met Ile Leu Ala Leu
465                 470                 475                 480

Ala Arg Pro Asp Pro Lys Lys Asn Leu Thr Thr Leu Val Lys Ala Phe
            485                 490                 495

Gly Glu Cys Lys Pro Leu Arg Glu Leu Ala Asn Leu Thr Leu Ile Met
            500                 505                 510

Gly Asn Arg Asp Asn Ile Asp Glu Met Ser Gly Thr Asn Ala Ser Val
            515                 520                 525

Leu Leu Ser Ile Leu Lys Met Ile Asp Lys Tyr Asp Leu Tyr Gly Leu
            530                 535                 540

Val Ala Tyr Pro Lys His His Lys Gln Ser Asp Val Pro Asp Ile Tyr
545                 550                 555                 560

Arg Leu Ala Ala Lys Thr Lys Gly Val Phe Ile Asn Pro Ala Phe Ile
            565                 570                 575

Glu Pro Phe Gly Leu Thr Leu Ile Glu Ala Ala Ala His Gly Leu Pro
            580                 585                 590

Ile Val Ala Thr Lys Asn Gly Gly Pro Val Asp Ile His Arg Val Leu
            595                 600                 605

Asp Asn Gly Ile Leu Val Asp Pro His Asn Gln Glu Ser Ile Ala Asp
            610                 615                 620

Ala Leu Leu Lys Leu Val Ala Glu Lys His Leu Trp Ala Lys Cys Arg
625                 630                 635                 640

Ala Asn Gly Leu Lys Asn Ile His Leu Phe Ser Trp Pro Glu His Cys
            645                 650                 655

Lys Ser Tyr Leu Ser Lys Leu Ala Ser Cys Lys Pro Arg Gln Pro Arg
            660                 665                 670

Trp Leu Arg Asn Glu Glu Asp Asp Glu Asn Ser Glu Ser Asp Ser
```

```
                675                 680                 685
Pro Ser Asp Ser Leu Arg Asp Ile Gln Asp Ile Ser Leu Asn Leu Lys
    690                 695                 700

Phe Ser Phe Asp Gly Asp Lys Asn Glu Ser Arg Glu Lys Gly Gly Gly
705                 710                 715                 720

Ser His Pro Asp Arg Ala Ser Lys Ile Glu Asn Ala Val Leu Glu
                725                 730                 735

Trp Ser Lys Gly Val Ala Lys Gly Pro Gln Arg Ser Met Ser Ile Glu
                740                 745                 750

Lys Gly Glu His Asn Ser Asn Ala Gly Lys Phe Pro Ala Leu Arg Arg
                755                 760                 765

Arg Lys Ile Met Phe Val Ile Ala Val Asp Cys Lys Pro Ser Ala Gly
770                 775                 780

Leu Ser Glu Ser Val Arg Lys Val Phe Ala Ala Val Glu Asn Glu Arg
785                 790                 795                 800

Ala Glu Gly Ser Val Gly Phe Ile Leu Ala Thr Ser Phe Asn Ile Ser
                805                 810                 815

Glu Ile Arg His Phe Leu Val Ser Glu Lys Leu Asn Pro Thr Asp Phe
                820                 825                 830

Asp Ala Phe Ile Cys Asn Ser Gly Gly Asp Leu Tyr Tyr Ser Ser His
                835                 840                 845

His Ser Glu Asp Asn Pro Phe Val Val Asp Leu Tyr Tyr His Ser Gln
                850                 855                 860

Ile Glu Tyr Arg Trp Gly Gly Glu Gly Leu Arg Lys Thr Leu Val Arg
865                 870                 875                 880

Trp Ala Ala Ser Ile Thr Asp Lys Lys Gly Glu Lys Glu His Val
                885                 890                 895

Ile Ile Glu Asp Glu Glu Thr Ser Ala Asp Tyr Cys Tyr Ser Phe Lys
                900                 905                 910

Val Gln Lys Pro Asn Val Val Pro Pro Val Lys Glu Ala Arg Lys Val
                915                 920                 925

Met Arg Ile Gln Ala Leu Arg Cys His Val Val Tyr Cys Gln Asn Gly
                930                 935                 940

Asn Lys Ile Asn Val Ile Pro Val Leu Ala Ser Arg Ala Gln Ala Leu
945                 950                 955                 960

Arg Tyr Leu Tyr Leu Arg Trp Gly Met Glu Leu Ser Lys Thr Val Val
                965                 970                 975

Val Val Gly Glu Ser Gly Asp Thr Asp Tyr Glu Met Leu Gly Gly
                980                 985                 990

Val His Lys Thr Val Val Leu Ser Gly Val Cys Thr Thr Ala Thr Asn
                995                 1000                1005

Leu Leu His Ala Asn Arg Ser Tyr Pro Leu Ala Asp Val Val Cys Phe
    1010                1015                1020

Asp Asp Leu Asn Ile Phe Lys Thr His Asn Glu Glu Cys Ser Ser Thr
1025                1030                1035                1040

Asp Leu Arg Ala Leu Leu Glu Glu His Gly Ala Phe Lys Ala
                1045                1050
```

<210> SEQ ID NO 4
<211> LENGTH: 1081
<212> TYPE: PRT
<213> ORGANISM: Craterostigma plantagineum

<400> SEQUENCE: 4

```
Met Ala Gly Asn Glu Trp Ile Asn Gly Tyr Leu Glu Ala Ile Leu Asp
 1               5                  10                  15

Thr Gly Ala Ser Ala Ile Asp Glu Asn Ser Gly Gly Lys Thr Ala
            20                  25                  30

Ala Ala Gln Lys Gly Arg His His Asp His His Phe Asn Pro Thr Lys
        35                  40                  45

Tyr Phe Val Glu Glu Val Val Ser Gly Val Asp Glu Ser Asp Leu His
    50                  55                  60

Arg Thr Trp Ile Lys Val Val Ala Thr Arg Asn Thr Arg Glu Arg Ser
65                  70                  75                  80

Ser Arg Leu Glu Asn Met Cys Trp Arg Ile Trp His Leu Thr Arg Lys
                85                  90                  95

Lys Lys Gln Leu Glu Trp Glu Asp Leu Gln Arg Leu Ala Ala Arg Lys
            100                 105                 110

Trp Glu Arg Glu Gln Gly Arg Lys Asp Val Thr Glu Asp Met Ser Glu
        115                 120                 125

Asp Leu Ser Glu Gly Glu Lys Gly Asp Val Met Gly Glu Thr Pro Val
    130                 135                 140

Ala Leu Asp Ser Pro Arg Gly Asn Lys Lys Tyr His Arg Asn Phe Ser
145                 150                 155                 160

Asn Leu Glu Val Trp Ser Asp Ser Asn Lys Glu Lys Lys Leu Tyr Ile
                165                 170                 175

Val Leu Ile Ser Leu His Gly Leu Val Arg Gly Glu Asn Met Glu Leu
            180                 185                 190

Gly Arg Asp Ser Asp Thr Gly Gly Gln Ile Lys Tyr Val Val Glu Val
        195                 200                 205

Ala Arg Ala Leu Ala Lys Met Pro Gly Val Tyr Arg Val Asp Leu Phe
    210                 215                 220

Thr Arg Gln Ile Ser Ser Pro Glu Val Asp Trp Ser Tyr Ala Glu Pro
225                 230                 235                 240

Thr Glu Met Leu Ser Ser Ser Thr Thr Ala Gly Glu Ala His Glu
                245                 250                 255

Pro Glu Glu Glu Glu Glu Glu Asp Leu Gly Glu Gly Ser Gly Ala
            260                 265                 270

Tyr Ile Ile Arg Ile Pro Phe Gly Pro Arg Asp Lys Tyr Leu Arg Lys
    275                 280                 285

Glu Leu Leu Trp Pro His Ile Gln Glu Phe Val Asp Gly Ala Leu Ser
290                 295                 300

His Ile Val Asn Met Ser Lys Ala Leu Gly Asp Gln Ile Gly Gly Gly
305                 310                 315                 320

Gln Pro Val Trp Pro Tyr Val Ile His Gly His Tyr Ala Asp Ala Gly
                325                 330                 335

Asp Ser Ala Ala Leu Leu Ser Gly Ala Leu Asn Val Pro Met Val Leu
            340                 345                 350

Thr Gly His Ser Leu Gly Arg Asn Lys Leu Glu Gln Leu Leu Lys Gln
        355                 360                 365

Gly Arg Gln Thr Lys Glu Asp Ile Asn Ser Met Tyr Arg Ile Met Arg
    370                 375                 380

Arg Ile Glu Ala Glu Glu Leu Ser Leu Asp Ala Ala Glu Leu Val Ile
385                 390                 395                 400

Thr Ser Thr Lys Gln Glu Ile Glu Glu Gln Trp Gly Leu Tyr Asp Gly
                405                 410                 415

Phe Asp Val Lys Leu Glu Arg Val Leu Arg Ala Arg Ala Arg Arg Gly
```

```
              420                 425                 430
Val Asn Cys His Gly Arg Phe Met Pro Arg Met Ala Val Ile Pro Pro
        435                 440                 445
Gly Met Asp Phe Ser Asn Val Val Pro Glu Asp Gly Ser Glu Gly
450                 455                 460
Asp Gly Asp Leu Ala Thr Leu Thr Glu Ala Thr Ser Pro Arg Ser Val
465                 470                 475                 480
Pro Ala Ile Trp Ala Asp Val Met Arg Phe Leu Thr Asn Pro His Lys
            485                 490                 495
Pro Met Ile Leu Ala Leu Ser Arg Pro Asp Pro Lys Lys Asn Ile Thr
            500                 505                 510
Thr Leu Val Lys Ala Phe Gly Glu Cys Arg Pro Leu Arg Glu Leu Ala
            515                 520                 525
Asn Leu Thr Leu Ile Met Gly Asn Arg Asp Asp Ile Asp Glu Met Ser
            530                 535                 540
Gly Gly Asn Ala Ser Val Leu Thr Thr Val Leu Lys Leu Ile Asp Arg
545                 550                 555                 560
Tyr Asp Leu Tyr Gly Gln Val Ala Phe Pro Lys His His Lys Gln Ser
            565                 570                 575
Asp Val Pro Glu Ile Tyr Arg Leu Ala Ser Lys Thr Lys Gly Val Phe
            580                 585                 590
Ile Asn Pro Ala Phe Ile Glu Pro Phe Gly Leu Thr Leu Ile Glu Ala
            595                 600                 605
Ala Ala His Gly Leu Pro Met Val Ala Thr Lys Asn Gly Gly Pro Val
    610                 615                 620
Asp Ile His Arg Ala Leu Asn Asn Gly Leu Leu Val Asp Pro His Asp
625                 630                 635                 640
Gln Asp Ala Ile Ala Asn Ala Leu Leu Lys Leu Val Ser Glu Lys Asn
                645                 650                 655
Leu Trp Asn Glu Cys Arg Lys Asn Gly Leu Lys Asn Ile His Leu Phe
                660                 665                 670
Ser Trp Pro Glu His Cys Arg Thr Tyr Leu Thr Arg Val Ala Ala Cys
            675                 680                 685
Arg Met Arg His Pro Gln Trp Lys Thr Asp Thr Pro Leu Asp Glu Thr
690                 695                 700
Ala Ile Asp Asp Ser Leu Asn Asp Ser Leu Lys Asp Val Leu Asp Met
705                 710                 715                 720
Ser Leu Arg Leu Ser Val Asp Gly Glu Lys Met Ser Val Asn Glu Ser
                725                 730                 735
Ser Ser Val Glu Leu Pro Gly Gly Glu Ala Ala Glu Leu Pro Asp Gln
            740                 745                 750
Val Arg Arg Val Leu Asn Lys Ile Lys Arg Gln Asp Ser Gly Pro Ala
            755                 760                 765
Gln Arg Glu Ala Glu Gly Lys Ala Gly Asp Val Pro Gly Lys Tyr Pro
770                 775                 780
Met Leu Arg Arg Arg Lys Leu Phe Val Ile Ala Leu Asp Cys Tyr
785                 790                 795                 800
Asp Leu Lys Gly Asn Pro Asp Lys Lys Met Ile Leu Ser Ile Gln Glu
                805                 810                 815
Ile Val Arg Ala Val Arg Leu Asp Pro Gln Met Ser Arg Phe Ser Gly
            820                 825                 830
Phe Ala Leu Ser Thr Ala Met Pro Val Ala Glu Leu Ala Asp Phe Leu
            835                 840                 845
```

-continued

```
Lys Ala Gly Asp Val Lys Val Asn Asp Phe Asp Ala Leu Ile Cys Ser
    850                 855                 860
Ser Gly Ser Glu Val Tyr Tyr Pro Gly Thr Tyr Gly Glu Ser Gly
865                 870                 875                 880
Lys Leu Tyr Leu Asp Pro Asp Tyr Thr Ser His Ile Glu Tyr Arg Trp
                885                 890                 895
Gly Gly Asp Gly Leu Lys Lys Thr Ile Ser Lys Leu Met Asn Thr Ala
                900                 905                 910
Glu Asp Gly Lys Ser Ser Val Ala Ser Ser Pro Ile Glu Leu Val Ala
                915                 920                 925
Lys Ser Ser Asn Ser His Cys Leu Ser Tyr Ala Ile Lys Asp Pro Ser
    930                 935                 940
Lys Ala Lys Lys Val Asp Asp Met Arg Gln Lys Leu Arg Met Arg Gly
945                 950                 955                 960
Leu Arg Cys His Leu Met Tyr Cys Arg Asn Ser Thr Ser Met Gln Val
                965                 970                 975
Val Pro Leu Leu Ala Ser Arg Ser Gln Ala Leu Arg Tyr Leu Phe Val
                980                 985                 990
Arg Trp Arg Leu Ser Val Ala Asn Met Tyr Val Ile Leu Gly Glu Thr
                995                 1000                1005
Gly Asp Thr Asp Tyr Glu Glu Leu Ile Ser Gly Thr His Lys Thr Leu
    1010                1015                1020
Ile Met Arg Gly Val Val Glu Lys Gly Ser Glu Glu Leu Leu Arg Thr
1025                1030                1035                1040
Ala Gly Ser Tyr Leu Arg Asp Asp Val Ile Pro Gln Asp Thr Pro Leu
                1045                1050                1055
Ile Ala Tyr Ala Asp Lys Gly Ala Lys Ala Glu His Ile Val Glu Thr
                1060                1065                1070
Phe Arg Gln Leu Ser Lys Ala Gly Met
    1075                1080

<210> SEQ ID NO 5
<211> LENGTH: 1059
<212> TYPE: PRT
<213> ORGANISM: Vicia faba

<400> SEQUENCE: 5

Met Ala Gly Asn Asp Trp Leu Asn Ser Tyr Leu Glu Ala Ile Leu Asp
1               5                   10                  15
Val Gly Pro Gly Leu Asp Asp Ala Lys Ser Ser Leu Leu Arg Glu
                20                  25                  30
Arg Gly Arg Phe Ser Pro Thr Arg Tyr Phe Val Glu Glu Val Ile Gly
            35                  40                  45
Phe Asp Glu Thr Asp Leu Tyr Arg Ser Trp Val Arg Ala Ser Ser Ser
    50                  55                  60
Arg Ser Pro Gln Glu Arg Asn Thr Arg Leu Glu Asn Met Cys Trp Arg
65                  70                  75                  80
Ile Trp Asn Leu Ala Arg Gln Lys Lys Gln Leu Glu Ser Glu Ala Val
                85                  90                  95
Gln Arg Val Asn Lys Arg Arg Leu Glu Arg Glu Arg Gly Arg Arg Glu
                100                 105                 110
Ala Thr Ala Asp Met Ser Glu Asp Leu Ser Glu Gly Glu Arg Gly Asp
            115                 120                 125
Pro Val Ser Asp Val Ser Thr His Gly Gly Gly Asp Ser Val Lys Ser
```

```
        130                 135                 140
Arg Leu Pro Arg Ile Ser Ser Ala Asp Ala Met Glu Thr Trp Val Asn
145                 150                 155                 160

Ser Gln Lys Gly Lys Lys Leu Tyr Ile Val Leu Ile Ser Ile His Gly
                165                 170                 175

Leu Ile Arg Gly Glu Asn Met Glu Leu Gly Arg Asp Ser Asp Thr Gly
                180                 185                 190

Gly Gln Val Lys Tyr Val Val Glu Leu Ala Arg Ala Leu Gly Ser Met
                195                 200                 205

Pro Gly Val Tyr Arg Val Asp Leu Leu Thr Arg Gln Val Ser Ser Pro
210                 215                 220

Asp Val Asp Trp Ser Tyr Gly Glu Pro Thr Glu Met Leu Ala Pro Arg
225                 230                 235                 240

Asn Thr Asp Glu Phe Gly Asp Asp Met Gly Glu Ser Ser Gly Ala Tyr
                245                 250                 255

Ile Ile Arg Ile Pro Phe Gly Pro Arg Asn Lys Tyr Ile Pro Lys Glu
                260                 265                 270

Glu Leu Trp Pro Tyr Ile Pro Glu Phe Val Asp Gly Ala Met Gly His
                275                 280                 285

Ile Ile Gln Met Ser Lys Ala Leu Gly Glu Gln Ile Gly Ser Gly His
                290                 295                 300

Ala Val Trp Pro Val Ala Ile His Gly His Tyr Ala Asp Ala Gly Asp
305                 310                 315                 320

Ser Ala Ala Leu Leu Ser Gly Ala Leu Asn Val Pro Met Ile Phe Thr
                325                 330                 335

Gly His Ser Leu Gly Arg Asp Lys Leu Glu Gln Leu Leu Lys Gln Gly
                340                 345                 350

Arg Leu Ser Thr Asp Glu Ile Asn Ser Thr Tyr Lys Ile Met Arg Arg
                355                 360                 365

Ile Glu Ala Glu Glu Leu Ala Leu Asp Gly Thr Glu Ile Val Ile Thr
                370                 375                 380

Ser Thr Arg Gln Glu Ile Glu Glu Gln Trp Arg Leu Tyr Asn Gly Phe
385                 390                 395                 400

Asp Pro Val Leu Glu Arg Lys Ile Arg Ala Arg Ile Arg Arg Asn Val
                405                 410                 415

Ser Cys Tyr Gly Arg Tyr Met Pro Arg Met Ser Val Ile Pro Pro Gly
                420                 425                 430

Met Glu Phe His His Ile Ala Pro Leu Asp Gly Asp Ile Glu Thr Glu
                435                 440                 445

Pro Glu Gly Ile Leu Asp His Pro Ala Pro Gln Asp Pro Pro Ile Trp
                450                 455                 460

Ser Glu Ile Met Arg Phe Phe Ser Asn Pro Arg Lys Pro Val Ile Leu
465                 470                 475                 480

Ala Leu Ala Arg Pro Asp Pro Lys Lys Asn Ile Thr Thr Leu Val Lys
                485                 490                 495

Ala Phe Gly Glu Cys Arg Pro Leu Arg Glu Leu Ala Asn Leu Thr Leu
                500                 505                 510

Ile Met Gly Asn Arg Asp Gly Ile Asp Glu Met Ser Ser Thr Ser Ser
                515                 520                 525

Ser Val Leu Leu Ser Val Leu Lys Leu Ile Asp Lys Tyr Asp Leu Tyr
                530                 535                 540

Gly Gln Val Ala Tyr Pro Lys His His Lys Gln Ser Asp Val Pro Asp
545                 550                 555                 560
```

```
Ile Tyr Arg Leu Ala Ala Lys Thr Lys Gly Val Phe Ile Asn Pro Ala
            565                 570                 575
Phe Ile Glu Pro Phe Gly Leu Thr Leu Ile Glu Ala Ala Tyr Gly
        580                 585                 590
Leu Pro Met Val Ala Thr Lys Asn Gly Gly Pro Val Asp Ile His Arg
        595                 600                 605
Val Leu Asp Asn Gly Leu Leu Ile Asp Pro His Asp Glu Lys Ser Ile
        610                 615                 620
Ala Asp Ala Leu Leu Lys Leu Val Ser Asn Lys Gln Leu Trp Ala Lys
625                 630                 635                 640
Cys Arg Gln Asn Gly Leu Lys Asn Ile His Leu Phe Ser Trp Pro Glu
                645                 650                 655
His Cys Lys Thr Tyr Leu Ser Lys Ile Ala Thr Cys Lys Pro Arg His
                660                 665                 670
Pro Gln Trp Gln Arg Ser Glu Asp Gly Gly Ser Ser Glu Ser Glu
            675                 680                 685
Glu Ser Pro Gly Asp Ser Leu Arg Asp Ile Gln Asp Leu Ser Leu Asn
        690                 695                 700
Leu Lys Phe Ser Leu Asp Gly Glu Arg Ser Gly Asp Ser Gly Asn Asp
705                 710                 715                 720
Asn Ser Leu Asp Pro Asp Gly Asn Ala Thr Asp Arg Thr Thr Lys Leu
                725                 730                 735
Glu Asn Ala Val Leu Ser Trp Ser Lys Gly Ile Ser Lys Asp Thr Arg
            740                 745                 750
Arg Gly Gly Ala Thr Glu Lys Ser Gly Gln Asn Ser Asn Ala Ser Lys
        755                 760                 765
Phe Pro Pro Leu Arg Ser Arg Asn Arg Leu Phe Val Ile Ala Val Asp
770                 775                 780
Cys Asp Thr Thr Ser Gly Leu Leu Glu Met Ile Lys Leu Ile Phe Glu
785                 790                 795                 800
Ala Ala Gly Glu Glu Arg Ala Glu Gly Ser Val Gly Phe Ile Leu Ser
                805                 810                 815
Thr Ser Leu Thr Ile Ser Glu Ile Gln Ser Phe Leu Ile Ser Gly Gly
            820                 825                 830
Leu Ser Pro Asn Asp Phe Asp Ala Tyr Ile Cys Asn Ser Gly Ser Asp
        835                 840                 845
Leu Tyr Tyr Pro Ser Leu Asn Ser Glu Asp Arg Leu Phe Val Gly Asp
        850                 855                 860
Leu Tyr Phe His Ser His Ile Glu Tyr Arg Trp Gly Gly Glu Gly Leu
865                 870                 875                 880
Arg Lys Thr Leu Ile Arg Trp Ala Ser Ser Ile Thr Asp Lys Lys Ser
                885                 890                 895
Glu Asn Asn Glu Gln Ile Val Ser Pro Ala Glu Gln Leu Ser Thr Asp
            900                 905                 910
Tyr Cys Tyr Ala Phe Asn Val Arg Lys Ala Gly Met Ala Pro Pro Leu
        915                 920                 925
Lys Glu Leu Arg Lys Leu Met Arg Ile Gln Ala Leu Arg Cys His Pro
        930                 935                 940
Ile Tyr Cys Gln Asn Gly Thr Arg Leu Asn Val Ile Pro Val Leu Ala
945                 950                 955                 960
Ser Arg Ser Gln Ala Leu Arg Tyr Leu Tyr Val Arg Trp Gly Phe Glu
                965                 970                 975
```

-continued

```
Leu Ser Lys Met Val Phe Val Gly Glu Cys Gly Asp Thr Asp Tyr
            980             985             990
Glu Gly Leu Val Gly Leu His Lys Ser Val Ile Leu Lys Gly Val
        995            1000            1005
Gly Ser Arg Ala Ile Ser Gln Leu His Asn Asn Arg Asn Tyr Pro Leu
    1010            1015            1020
Ser Asp Val Met Pro Leu Asp Ser Pro Asn Ile Val Gln Ala Thr Glu
1025            1030            1035            1040
Gly Ser Ser Ala Asp Ile Gln Ala Leu Leu Glu Lys Val Gly Tyr
            1045            1050            1055
His Lys Gly

<210> SEQ ID NO 6
<211> LENGTH: 1053
<212> TYPE: PRT
<213> ORGANISM: Solanum tuberosum

<400> SEQUENCE: 6

Met Ala Gly Asn Asp Trp Ile Asn Ser Tyr Leu Glu Ala Ile Leu Asp
 1               5                  10                  15
Val Gly Pro Gly Leu Asp Asp Lys Ser Ser Leu Leu Arg Glu
            20              25                  30
Arg Gly Arg Phe Ser Pro Thr Arg Tyr Phe Val Glu Val Ile Thr
        35              40                  45
Gly Phe Asp Glu Thr Asp Leu His Arg Ser Trp Ile Arg Ala Gln Ala
    50                  55                  60
Thr Arg Ser Pro Gln Arg Arg Asn Thr Arg Leu Glu Asn Met Cys Trp
65                  70                  75                  80
Arg Ile Trp Asn Leu Ala Arg Gln Lys Lys Gln Leu Glu Gly Glu Gln
                85                  90                  95
Ala Gln Trp Met Ala Lys Arg Arg Gln Glu Arg Glu Arg Gly Arg Arg
            100                 105                 110
Glu Ala Val Ala Asp Met Ser Asp Leu Ser Glu Gly Glu Lys Gly
        115             120                 125
Asp Ile Val Ala Asp Met Ser Ser His Gly Glu Ser Thr Arg Gly Arg
    130                 135                 140
Leu Pro Arg Ile Ser Ser Val Glu Thr Met Glu Ala Trp Val Ser Gln
145                 150                 155                 160
Gln Arg Gly Lys Lys Leu Tyr Ile Val Leu Ile Ser Leu His Gly Leu
                165                 170                 175
Ile Arg Gly Glu Asn Met Glu Leu Gly Arg Asp Ser Asp Thr Gly Gly
            180                 185                 190
Gln Val Lys Tyr Val Val Glu Leu Ala Arg Ala Leu Gly Ser Met Pro
        195             200                 205
Gly Val Tyr Arg Val Asp Leu Leu Thr Arg Gln Val Ser Ser Pro Glu
    210                 215                 220
Val Asp Trp Ser Tyr Gly Glu Pro Thr Glu Leu Ala Pro Ile Ser Thr
225                 230                 235                 240
Asp Gly Leu Met Thr Glu Met Gly Glu Ser Ser Gly Ala Tyr Ile Ile
                245                 250                 255
Arg Ile Pro Phe Gly Pro Arg Glu Lys Tyr Ile Pro Lys Glu Gln Leu
            260                 265                 270
Trp Pro Tyr Ile Pro Glu Phe Val Asp Gly Ala Leu Asn His Ile Ile
        275             280                 285
```

-continued

```
Gln Met Ser Lys Val Leu Gly Glu Gln Ile Gly Ser Gly Tyr Pro Val
    290                 295                 300
Trp Pro Val Ala Ile His Gly His Tyr Ala Asp Ala Gly Asp Ser Ala
305                 310                 315                 320
Ala Leu Leu Ser Gly Ala Leu Asn Val Pro Met Leu Phe Thr Gly His
                325                 330                 335
Ser Leu Gly Arg Asp Lys Leu Glu Gln Leu Leu Ala Gln Gly Arg Lys
            340                 345                 350
Ser Lys Asp Glu Ile Asn Ser Thr Tyr Lys Ile Met Arg Arg Ile Glu
        355                 360                 365
Ala Glu Glu Leu Thr Leu Asp Ala Ser Glu Ile Val Ile Thr Ser Thr
    370                 375                 380
Arg Gln Glu Ile Asp Glu Gln Trp Arg Leu Tyr Asp Gly Phe Asp Pro
385                 390                 395                 400
Ile Leu Glu Arg Lys Leu Arg Ala Arg Ile Lys Arg Asn Val Ser Cys
                405                 410                 415
Tyr Gly Arg Phe Met Pro Arg Met Ala Val Ile Pro Pro Gly Met Glu
            420                 425                 430
Phe His His Ile Val Pro His Glu Gly Asp Met Asp Gly Glu Thr Glu
        435                 440                 445
Gly Ser Glu Asp Gly Lys Thr Pro Asp Pro Ile Trp Ala Glu Ile
    450                 455                 460
Met Arg Phe Phe Ser Asn Pro Arg Lys Pro Met Ile Leu Ala Leu Ala
465                 470                 475                 480
Arg Pro Asp Pro Lys Lys Asn Leu Thr Thr Leu Val Lys Ala Phe Gly
                485                 490                 495
Glu Cys Arg Pro Leu Arg Asp Leu Ala Asn Leu Thr Leu Ile Met Gly
            500                 505                 510
Asn Arg Asp Asn Ile Asp Glu Met Ser Ser Thr Asn Ser Ala Leu Leu
        515                 520                 525
Leu Ser Ile Leu Lys Met Ile Asp Lys Tyr Asp Leu Tyr Gly Gln Val
    530                 535                 540
Ala Tyr Pro Lys His His Lys Gln Ser Asp Val Pro Asp Ile Tyr Arg
545                 550                 555                 560
Leu Ala Ala Lys Thr Lys Gly Val Phe Ile Asn Pro Ala Phe Ile Glu
                565                 570                 575
Pro Phe Gly Leu Thr Leu Ile Glu Ala Ala Tyr Gly Leu Pro Met
            580                 585                 590
Val Ala Thr Lys Asn Gly Gly Pro Val Asp Ile His Arg Val Leu Asp
        595                 600                 605
Asn Gly Leu Leu Val Asp Pro His Asp Gln Gln Ala Ile Ala Asp Ala
    610                 615                 620
Leu Leu Lys Leu Val Ala Asp Lys Gln Leu Trp Ala Lys Cys Arg Ala
625                 630                 635                 640
Asn Gly Leu Lys Asn Ile His Leu Phe Ser Trp Pro Glu His Cys Lys
                645                 650                 655
Thr Tyr Leu Ser Arg Ile Ala Ser Cys Lys Pro Arg Gln Pro Arg Trp
            660                 665                 670
Leu Arg Ser Ile Asp Asp Asp Glu Asn Ser Glu Thr Asp Ser Pro
        675                 680                 685
Ser Asp Ser Leu Arg Asp Ile His Asp Ile Ser Leu Asn Leu Arg Phe
    690                 695                 700
Ser Leu Asp Gly Glu Lys Asn Asp Asn Lys Glu Asn Ala Asp Asn Thr
```

```
                705               710              715              720

Leu Asp Pro Glu Val Arg Arg Ser Lys Leu Glu Asn Ala Val Leu Ser
                            725                 730                 735

Leu Ser Lys Gly Ala Leu Lys Ser Thr Ser Lys Ser Trp Ser Ser Asp
                            740                 745                 750

Lys Ala Asp Gln Asn Pro Gly Ala Gly Lys Phe Pro Ala Ile Arg Arg
                            755                 760                 765

Arg Arg His Ile Phe Val Ile Ala Val Asp Cys Asp Ala Ser Ser Gly
                            770                 775                 780

Leu Ser Gly Ser Val Lys Lys Ile Phe Glu Ala Val Lys Glu Arg
        785                 790                 795                 800

Ala Glu Gly Ser Ile Gly Phe Ile Leu Ala Thr Ser Phe Asn Ile Ser
                            805                 810                 815

Glu Val Gln Ser Phe Leu Leu Ser Gly Met Asn Pro Thr Asp Phe
                            820                 825                 830

Asp Ala Tyr Ile Cys Asn Ser Gly Asp Leu Tyr Tyr Ser Ser Phe
                            835                 840                 845

His Ser Glu Gln Asn Pro Phe Val Val Asp Leu Tyr Tyr His Ser His
                            850                 855                 860

Ile Glu Tyr Arg Trp Gly Gly Glu Gly Leu Arg Lys Thr Leu Val Arg
        865                 870                 875                 880

Trp Ala Ala Ser Ile Ile Asp Lys Asn Gly Glu Asn Gly Asp His Ile
                            885                 890                 895

Val Val Glu Asp Glu Asp Asn Ser Ala Asp Tyr Cys Tyr Thr Phe Lys
                            900                 905                 910

Val Cys Lys Pro Gly Thr Val Pro Pro Ser Lys Glu Leu Arg Lys Val
                            915                 920                 925

Met Arg Ile Gln Ala Leu Arg Cys His Ala Val Tyr Cys Gln Asn Gly
                            930                 935                 940

Ser Arg Ile Asn Val Ile Pro Val Leu Ala Ser Arg Ser Gln Ala Leu
        945                 950                 955                 960

Arg Tyr Leu Tyr Leu Arg Trp Gly Met Asp Leu Ser Lys Leu Val Val
                            965                 970                 975

Phe Val Gly Glu Ser Gly Asp Thr Asp Tyr Glu Gly Leu Ile Gly Gly
                            980                 985                 990

Leu Arg Lys Ala Val Ile Met Lys Gly Leu Cys Thr Asn Ala Ser Ser
                            995                 1000                1005

Leu Ile His Gly Asn Arg Asn Tyr Pro Leu Ser Asp Val Leu Pro Phe
                            1010                1015                1020

Asp Ser Pro Asn Val Ile Gln Ala Asp Glu Glu Cys Ser Ser Thr Glu
        1025                1030                1035                1040

Ile Arg Cys Leu Leu Glu Lys Leu Ala Val Leu Lys Gly
                            1045                1050

<210> SEQ ID NO 7
<211> LENGTH: 1045
<212> TYPE: PRT
<213> ORGANISM: Beta vulgaris

<400> SEQUENCE: 7

Met Ala Gly Asn Asp Trp Ile Asn Ser Tyr Leu Glu Ala Ile Leu Asp
 1               5                  10                  15

Val Gly Pro Gly Leu Asp Asp Ala Lys Ser Ser Leu Leu Leu Arg Glu
                20                  25                  30
```

-continued

```
Arg Gly Arg Phe Ser Pro Thr Arg Tyr Phe Val Glu Glu Val Ile Thr
         35                  40                  45

Gly Phe Asp Glu Thr Asp Leu His Arg Ser Trp Val Arg Ala Gln Ala
     50                  55                  60

Thr Arg Ser Pro Gln Glu Arg Asn Thr Arg Leu Glu Asn Met Cys Trp
 65                  70                  75                  80

Arg Ile Trp Asn Leu Ala Arg Gln Lys Lys Gln Leu Glu Asn Glu Glu
                 85                  90                  95

Ala Gln Arg Lys Thr Lys Arg Arg Met Glu Leu Glu Arg Gly Arg Arg
             100                 105                 110

Glu Ala Thr Ala Asp Met Ser Glu Asp Leu Ser Glu Gly Glu Lys Asp
             115                 120                 125

Ile Ser Ala His Gly Asp Ser Thr Arg Pro Arg Leu Pro Arg Ile Asn
         130                 135                 140

Ser Leu Asp Ala Met Glu Thr Trp Ile Ser Gln Gln Lys Glu Lys Lys
145                 150                 155                 160

Leu Tyr Leu Val Leu Ile Ser Leu His Gly Leu Ile Arg Gly Glu Asn
                 165                 170                 175

Met Glu Leu Gly Arg Asp Ser Asp Thr Gly Gly Gln Val Lys Tyr Val
             180                 185                 190

Val Glu Leu Ala Arg Ala Leu Gly Ser Met Pro Gly Val Tyr Arg Val
             195                 200                 205

Asp Leu Leu Thr Arg Gln Val Ser Ser Pro Asp Val Asp Trp Ser Tyr
         210                 215                 220

Gly Glu Pro Thr Glu Met Leu Asn Pro Arg Asp Ser Asn Gly Phe Asp
225                 230                 235                 240

Asp Asp Asp Asp Glu Met Gly Glu Ser Ser Gly Ala Tyr Ile Val Arg
                 245                 250                 255

Ile Pro Phe Gly Pro Arg Asp Lys Tyr Ile Ala Lys Glu Glu Leu Trp
             260                 265                 270

Pro Tyr Ile Pro Glu Phe Val Asp Gly Ala Leu Asn His Ile Val Gln
         275                 280                 285

Met Ser Lys Val Leu Gly Glu Gln Ile Gly Ser Gly Glu Thr Val Trp
     290                 295                 300

Pro Val Ala Ile His Gly His Tyr Ala Asp Ala Gly Asp Ser Ala Ala
305                 310                 315                 320

Leu Leu Ser Gly Gly Leu Asn Val Pro Met Leu Leu Thr Gly His Ser
                 325                 330                 335

Leu Gly Arg Asp Lys Leu Glu Gln Leu Leu Lys Gln Gly Arg Met Ser
             340                 345                 350

Lys Asp Asp Ile Asn Asn Thr Tyr Lys Ile Met Arg Arg Ile Glu Ala
             355                 360                 365

Glu Glu Leu Ser Leu Asp Ala Ser Glu Ile Val Ile Thr Ser Thr Arg
         370                 375                 380

Gln Glu Ile Glu Glu Gln Trp His Leu Tyr Asp Gly Phe Asp Pro Val
385                 390                 395                 400

Leu Glu Arg Lys Leu Arg Ala Arg Met Lys Arg Gly Val Ser Cys Tyr
                 405                 410                 415

Gly Arg Phe Met Pro Arg Met Val Val Ile Pro Pro Gly Met Glu Phe
             420                 425                 430

Asn His Ile Val Pro His Glu Gly Asp Met Asp Gly Glu Thr Glu Glu
             435                 440                 445

Thr Glu Glu His Pro Thr Ser Pro Asp Pro Pro Ile Trp Ala Glu Ile
```

-continued

```
            450                 455                 460
Met Arg Phe Phe Ser Lys Pro Arg Lys Pro Met Ile Leu Ala Leu Ala
465                 470                 475                 480
Arg Pro Asp Pro Lys Lys Asn Ile Thr Thr Leu Val Lys Ala Phe Gly
                485                 490                 495
Glu Cys Arg Pro Leu Arg Glu Leu Ala Asn Leu Thr Leu Ile Met Gly
                500                 505                 510
Asn Arg Asp Gly Ile Asp Glu Met Ser Ser Thr Ser Ser Ser Val Leu
                515                 520                 525
Leu Ser Val Leu Lys Leu Ile Asp Gln Tyr Asp Leu Tyr Gly Gln Val
            530                 535                 540
Ala Tyr Pro Lys His His Lys Gln Ala Asp Val Pro Glu Ile Tyr Arg
545                 550                 555                 560
Leu Ala Ala Lys Thr Lys Gly Val Phe Ile Asn Pro Ala Phe Ile Glu
                565                 570                 575
Pro Phe Gly Leu Thr Leu Ile Glu Ala Ala His Gly Leu Pro Met
                580                 585                 590
Val Ala Thr Lys Asn Gly Gly Pro Val Asp Ile Gln Arg Val Leu Asp
                595                 600                 605
Asn Gly Leu Leu Val Asp Pro His Glu Gln Gln Ser Ile Ala Thr Ala
            610                 615                 620
Leu Leu Lys Leu Val Ala Asp Lys Gln Leu Trp Thr Lys Cys Gln Gln
625                 630                 635                 640
Asn Gly Leu Lys Asn Ile His Leu Tyr Ser Trp Pro Glu His Ser Lys
                645                 650                 655
Thr Tyr Leu Ser Arg Ile Ala Ser Ser Arg Gln Arg Gln Pro Gln Trp
                660                 665                 670
Gln Arg Ser Ser Asp Glu Gly Leu Asp Asn Gln Glu Pro Glu Ser Pro
                675                 680                 685
Ser Asp Ser Leu Arg Asp Ile Lys Asp Ile Ser Leu Asn Leu Glu Val
                690                 695                 700
Leu Val Arg Pro Glu Lys Arg Val Lys Thr Leu Lys Ile Leu Gly Leu
705                 710                 715                 720
Met Thr Lys Ala Asn Ser Arg Met Leu Leu Cys Ser Trp Ser Asn Gly
                725                 730                 735
Val His Lys Met Leu Arg Lys Ala Arg Phe Ser Asp Lys Val Asp Gln
                740                 745                 750
Ala Ser Ser Lys Tyr Pro Ala Phe Arg Arg Lys Leu Ile Tyr Val
                755                 760                 765
Ile Ala Val Asp Gly Asp Tyr Glu Asp Gly Leu Phe Asp Ile Val Arg
            770                 775                 780
Arg Ile Phe Asp Ala Ala Gly Lys Glu Lys Ile Glu Gly Ser Ile Gly
785                 790                 795                 800
Phe Ile Leu Ser Thr Ser Tyr Ser Met Pro Glu Ile Gln Asn Tyr Leu
                805                 810                 815
Leu Ser Lys Gly Phe Asn Leu His Asp Phe Asp Ala Tyr Ile Cys Asn
                820                 825                 830
Ser Gly Ser Glu Leu Tyr Tyr Ser Ser Leu Asn Ser Glu Ser Asn
                835                 840                 845
Ile Ile Ala Asp Ser Asp Tyr His Ser His Ile Glu Tyr Arg Trp Gly
            850                 855                 860
Gly Glu Gly Leu Arg Arg Thr Leu Leu Arg Trp Ala Ala Ser Ile Thr
865                 870                 875                 880
```

-continued

```
Glu Lys Asn Gly Glu Asn Glu Glu Gln Val Ile Thr Glu Asp Glu Glu
            885                 890                 895

Val Ser Thr Gly Tyr Cys Phe Ala Phe Lys Ile Lys Asn Gln Asn Lys
        900                 905                 910

Val Pro Pro Thr Lys Glu Leu Arg Lys Ser Met Arg Ile Gln Ala Leu
    915                 920                 925

Arg Cys His Val Ile Tyr Cys Gln Asn Gly Ser Lys Met Asn Val Ile
930                 935                 940

Pro Val Leu Ala Ser Arg Ser Gln Ala Leu Arg Tyr Leu Tyr Val Arg
945                 950                 955                 960

Trp Gly Val Glu Leu Ser Lys Met Val Val Phe Val Gly Glu Cys Gly
                965                 970                 975

Asp Thr Asp Tyr Glu Gly Leu Leu Gly Val His Lys Thr Val Ile
            980                 985                 990

Leu Lys Gly Val Ser Asn Thr Ala Leu Arg Ser Leu His Ala Asn Arg
        995                 1000                1005

Ser Tyr Pro Leu Ser His Val Val Ser Leu Asp Ser Pro Asn Ile Gly
    1010                1015                1020

Glu Val Ser Lys Gly Cys Ser Ser Glu Ile Gln Ser Ile Val Thr
1025                1030                1035                1040

Lys Leu Ser Lys Ala
            1045
```

<210> SEQ ID NO 8
<211> LENGTH: 1068
<212> TYPE: PRT
<213> ORGANISM: Zea mays

<400> SEQUENCE: 8

```
Met Ala Gly Asn Glu Trp Ile Asn Gly Tyr Leu Glu Ala Ile Leu Asp
 1               5                  10                  15

Ser His Thr Ser Ser Arg Gly Ala Gly Gly Gly Gly Gly Gly Gly Asp
            20                  25                  30

Pro Arg Ser Pro Thr Lys Ala Ala Ser Pro Arg Gly Ala His Met Asn
        35                  40                  45

Phe Asn Pro Ser His Tyr Phe Val Glu Glu Val Lys Gly Val Asp
    50                  55                  60

Glu Ser Asp Leu His Arg Thr Trp Ile Lys Val Val Ala Thr Arg Asn
65                  70                  75                  80

Ala Arg Glu Arg Ser Thr Arg Leu Glu Asn Met Cys Trp Arg Ile Trp
                85                  90                  95

His Leu Ala Arg Lys Lys Lys Gln Leu Glu Leu Glu Gly Ile Gln Arg
            100                 105                 110

Ile Ser Ala Arg Arg Lys Glu Gln Glu Gln Val Arg Arg Glu Ala Thr
        115                 120                 125

Glu Asp Leu Ala Glu Asp Leu Ser Glu Gly Glu Lys Gly Asp Thr Ile
    130                 135                 140

Gly Glu Leu Ala Pro Val Glu Thr Thr Lys Lys Phe Gln Arg Asn
145                 150                 155                 160

Phe Ser Asp Leu Thr Val Trp Ser Asp Asp Asn Lys Glu Lys Lys Leu
                165                 170                 175

Tyr Ile Val Leu Ile Ser Val His Gly Leu Val Arg Gly Glu Asn Met
            180                 185                 190

Glu Leu Gly Arg Asp Ser Asp Thr Gly Gly Gln Val Lys Tyr Val Val
```

-continued

```
            195                 200                 205
Glu Leu Ala Arg Ala Met Ser Met Met Pro Gly Val Tyr Arg Val Asp
        210                 215                 220

Leu Phe Thr Arg Gln Val Ser Ser Pro Asp Val Asp Trp Ser Tyr Gly
225                 230                 235                 240

Glu Pro Thr Glu Met Leu Cys Ala Gly Ser Asn Asp Gly Gly Met
                245                 250                 255

Gly Glu Ser Gly Gly Ala Tyr Ile Val Arg Ile Pro Cys Gly Pro Arg
                260                 265                 270

Asp Lys Tyr Leu Lys Lys Glu Ala Leu Trp Pro Tyr Leu Gln Glu Phe
                275                 280                 285

Val Asp Gly Ala Leu Ala His Ile Leu Asn Met Ser Lys Ala Leu Gly
        290                 295                 300

Glu Gln Val Gly Asn Gly Arg Pro Val Leu Pro Tyr Val Ile His Gly
305                 310                 315                 320

His Tyr Ala Asp Ala Gly Asp Val Ala Ala Leu Leu Ser Gly Ala Leu
                325                 330                 335

Asn Val Pro Met Val Leu Thr Gly His Ser Leu Gly Arg Asn Lys Leu
                340                 345                 350

Glu Gln Leu Leu Lys Gln Gly Arg Met Ser Lys Glu Glu Ile Asp Ser
                355                 360                 365

Thr Tyr Lys Ile Met Arg Arg Ile Glu Gly Glu Leu Ala Leu Asp
370                 375                 380

Ala Ser Glu Leu Val Ile Thr Ser Thr Arg Gln Glu Ile Asp Glu Gln
385                 390                 395                 400

Trp Gly Leu Tyr Asp Gly Phe Asp Val Lys Leu Glu Lys Val Leu Arg
                405                 410                 415

Ala Arg Ala Arg Arg Gly Val Ser Cys His Gly Arg Tyr Met Pro Arg
                420                 425                 430

Met Val Val Ile Pro Pro Gly Met Asp Phe Ser Asn Val Val Val His
        435                 440                 445

Glu Asp Ile Asp Gly Asp Gly Asp Val Lys Asp Asp Ile Val Gly Leu
        450                 455                 460

Glu Gly Ala Ser Pro Lys Ser Met Pro Pro Ile Trp Ala Glu Val Met
465                 470                 475                 480

Arg Phe Leu Thr Asn Pro His Lys Pro Met Ile Leu Ala Leu Ser Arg
                485                 490                 495

Pro Asp Pro Lys Lys Asn Ile Thr Thr Leu Val Lys Ala Phe Gly Glu
                500                 505                 510

Cys Arg Pro Leu Arg Glu Leu Ala Asn Leu Thr Leu Ile Met Gly Asn
                515                 520                 525

Arg Asp Asp Ile Asp Asp Met Ser Ala Gly Asn Ala Ser Val Leu Thr
                530                 535                 540

Thr Val Leu Lys Leu Ile Asp Lys Tyr Asp Leu Tyr Gly Ser Val Ala
545                 550                 555                 560

Phe Pro Lys His His Asn Gln Ala Asp Val Pro Glu Ile Tyr Arg Leu
                565                 570                 575

Ala Ala Lys Met Lys Gly Val Phe Ile Asn Pro Ala Leu Val Glu Pro
                580                 585                 590

Phe Gly Leu Thr Leu Ile Glu Ala Ala His Gly Leu Pro Ile Val
                595                 600                 605

Ala Thr Lys Asn Gly Gly Pro Val Asp Ile Thr Asn Ala Leu Asn Asn
        610                 615                 620
```

-continued

```
Gly Leu Leu Val Asp Pro His Asp Gln Asn Ala Ile Ala Asp Ala Leu
625                 630                 635                 640

Leu Lys Leu Val Ala Asp Lys Asn Leu Trp Gln Glu Cys Arg Arg Asn
                645                 650                 655

Gly Leu Arg Asn Ile His Leu Tyr Ser Trp Pro Glu His Cys Arg Thr
            660                 665                 670

Tyr Leu Thr Arg Val Ala Gly Cys Arg Leu Arg Asn Pro Arg Trp Leu
        675                 680                 685

Lys Asp Thr Pro Ala Asp Ala Gly Ala Asp Glu Glu Phe Leu Glu
    690                 695                 700

Asp Ser Met Asp Ala Gln Asp Leu Ser Leu Arg Leu Ser Ile Asp Gly
705                 710                 715                 720

Glu Lys Ser Ser Leu Asn Thr Asn Asp Pro Leu Trp Phe Asp Pro Gln
                725                 730                 735

Asp Gln Val Gln Lys Ile Met Asn Asn Ile Lys Gln Ser Ser Ala Leu
                740                 745                 750

Pro Pro Ser Met Ser Ser Val Ala Ala Glu Gly Thr Gly Ser Thr Met
            755                 760                 765

Asn Lys Tyr Pro Leu Leu Arg Arg Arg Arg Leu Phe Val Ile Ala
        770                 775                 780

Val Asp Cys Tyr Gln Asp Asp Gly Arg Ala Ser Lys Lys Met Leu Gln
785                 790                 795                 800

Val Ile Gln Glu Val Phe Arg Ala Val Arg Ser Asp Ser Gln Met Phe
                805                 810                 815

Lys Ile Ser Gly Phe Thr Leu Ser Thr Ala Met Pro Leu Ser Glu Thr
                820                 825                 830

Leu Gln Leu Leu Gln Leu Gly Lys Ile Pro Ala Thr Asp Phe Asp Ala
            835                 840                 845

Leu Ile Cys Gly Ser Gly Ser Glu Val Tyr Tyr Pro Gly Thr Ala Asn
    850                 855                 860

Cys Met Asp Ala Glu Gly Lys Leu Arg Pro Asp Gln Asp Tyr Leu Met
865                 870                 875                 880

His Ile Ser His Arg Trp Ser His Asp Gly Ala Arg Gln Thr Ile Ala
                885                 890                 895

Lys Leu Met Gly Ala Gln Asp Gly Ser Gly Asp Ala Val Glu Gln Asp
            900                 905                 910

Val Ala Ser Ser Asn Ala His Cys Val Ala Phe Leu Ile Lys Asp Pro
    915                 920                 925

Gln Lys Val Lys Thr Val Asp Glu Met Arg Glu Arg Leu Arg Met Arg
930                 935                 940

Gly Leu Arg Cys His Ile Met Tyr Cys Arg Asn Ser Thr Arg Leu Gln
945                 950                 955                 960

Val Val Pro Leu Leu Ala Ser Arg Ser Gln Ala Leu Arg Tyr Leu Ser
                965                 970                 975

Val Arg Trp Gly Val Ser Val Gly Asn Met Tyr Leu Ile Thr Gly Glu
            980                 985                 990

His Gly Asp Thr Asp Leu Glu Glu Met Leu Ser Gly Leu His Lys Thr
        995                 1000                1005

Val Ile Val Arg Gly Val Thr Glu Lys Gly Ser Glu Ala Leu Val Arg
    1010                1015                1020

Ser Pro Gly Ser Tyr Lys Arg Asp Asp Val Val Pro Ser Glu Thr Pro
1025                1030                1035                1040
```

```
Leu Ala Ala Tyr Thr Thr Gly Glu Leu Lys Ala Asp Glu Ile Met Arg
            1045                1050                1055

Ala Leu Lys Gln Val Ser Lys Thr Ser Ser Gly Met
        1060                1065
```

<210> SEQ ID NO 9
<211> LENGTH: 1084
<212> TYPE: PRT
<213> ORGANISM: Oryza sativa

<400> SEQUENCE: 9

```
Met Ala Gly Asn Glu Trp Ile Asn Gly Tyr Leu Glu Ala Ile Leu Asp
  1               5                  10                  15

Ser Gly Gly Ala Ala Gly Gly Gly Gly Gly Gly Gly Gly Gly Gly Gly
             20                  25                  30

Gly Gly Gly Gly Gly Gly Gly Gly Gly Gly Gly Gly Val Asp Pro
         35                  40                  45

Ser Ser Pro Thr Thr Gly Thr Thr Ser Pro Arg Gly Pro His Met Asn
 50                  55                  60

Phe Asn Pro Thr His Tyr Phe Val Glu Val Val Lys Gly Val Asp
 65                  70                  75                  80

Glu Ser Asp Leu His Arg Thr Trp Ile Lys Val Val Ala Thr Arg Asn
                 85                  90                  95

Ala Arg Glu Arg Ser Thr Arg Leu Glu Asn Met Cys Trp Arg Ile Trp
            100                 105                 110

His Leu Ala Arg Lys Lys Lys Gln Leu Glu Leu Gly Ile Leu Arg
            115                 120                 125

Ile Ser Ala Arg Arg Lys Glu Gln Glu Gln Val Arg Arg Glu Thr Ser
130                 135                 140

Glu Asp Leu Ala Glu Asp Leu Phe Glu Gly Glu Lys Ala Asp Thr Val
145                 150                 155                 160

Gly Glu Leu Ala Gln Gln Asp Thr Pro Met Lys Lys Phe Gln Arg
                165                 170                 175

Asn Phe Ser Glu Leu Thr Val Ser Trp Ser Asp Glu Asn Lys Glu Lys
            180                 185                 190

Lys Leu Tyr Ile Val Leu Ile Ser Leu His Gly Leu Val Arg Gly Asp
        195                 200                 205

Asn Met Glu Leu Gly Arg Asp Ser Asp Thr Gly Gly Gln Val Lys Tyr
    210                 215                 220

Val Val Glu Leu Ala Arg Ala Leu Ala Met Met Pro Gly Val Tyr Arg
225                 230                 235                 240

Val Asp Leu Phe Thr Arg Gln Val Ser Ser Pro Glu Val Asp Trp Ser
                245                 250                 255

Tyr Gly Glu Pro Thr Glu Met Leu Thr Ser Gly Ser Thr Asp Gly Glu
            260                 265                 270

Gly Ser Gly Glu Ser Ala Gly Ala Tyr Ile Val Arg Ile Pro Cys Gly
        275                 280                 285

Pro Arg Asp Lys Tyr Leu Arg Lys Glu Ala Leu Trp Pro Tyr Leu Gln
    290                 295                 300

Glu Phe Val Asp Gly Ala Leu Ala His Ile Leu Asn Met Ser Lys Ala
305                 310                 315                 320

Leu Gly Glu Gln Val Ser Asn Gly Lys Leu Val Leu Pro Tyr Val Ile
                325                 330                 335

His Gly His Tyr Ala Asp Ala Gly Asp Val Ala Ala Leu Leu Ser Gly
            340                 345                 350
```

```
Ala Leu Asn Val Pro Met Val Leu Thr Gly His Ser Leu Gly Arg Asn
        355                 360                 365

Lys Leu Glu Gln Ile Met Lys Gln Gly Arg Met Ser Lys Glu Glu Met
    370                 375                 380

Asp Ser Thr Tyr Lys Ile Met Arg Arg Ile Glu Gly Glu Leu Ala
385                 390                 395                 400

Leu Asp Ala Ala Glu Leu Val Ile Thr Ser Thr Arg Gln Glu Ile Asp
                405                 410                 415

Glu Gln Trp Gly Leu Tyr Asp Gly Phe Asp Val Lys Leu Glu Lys Val
            420                 425                 430

Leu Arg Ala Arg Ala Arg Arg Gly Val Ser Cys His Gly Arg Phe Met
        435                 440                 445

Pro Arg Met Val Val Ile Pro Pro Gly Met Asp Phe Ser Val Val
    450                 455                 460

Val Pro Glu Asp Thr Ser Asp Gly Asp Asp Gly Lys Asp Phe Glu Ile
465                 470                 475                 480

Ala Ser Pro Arg Ser Leu Pro Pro Ile Trp Ala Glu Val Ser Arg Phe
                485                 490                 495

Trp Thr Asn Pro His Lys Pro Met Ile Leu Ala Leu Ser Arg Pro Asp
            500                 505                 510

Pro Lys Lys Asn Ile Thr Thr Leu Val Lys Ala Phe Gly Glu Cys Arg
        515                 520                 525

Pro Leu Arg Glu Leu Ala Asn Leu Ile Leu Ser Met Gly Thr Arg Asp
    530                 535                 540

Asp Ile Asp Gly Met Ser Ala Gly Asn Ala Ser Val Leu Thr Thr Val
545                 550                 555                 560

Leu Lys Leu Ile Asp Lys Tyr Asp Leu Tyr Gly Ser Val Ala Phe Pro
                565                 570                 575

Lys Tyr His Lys Gln Ser Asp Val Pro Glu Ile Tyr Arg Leu Thr Gly
            580                 585                 590

Lys Met Lys Gly Val Phe Ile Asn Pro Ala Leu Val Glu Pro Phe Gly
        595                 600                 605

Leu Thr Leu Ile Glu Ala Ala Ala His Gly Leu Pro Ile Val Gly Thr
    610                 615                 620

Lys Asn Gly Gly Pro Val Asp Ile Lys Asn Ala Leu Asn Asn Gly Leu
625                 630                 635                 640

Leu Val Asp Pro His Asp Gln His Ala Ile Ala Asp Ala Leu Leu Lys
                645                 650                 655

Leu Val Ala Asp Lys Asn Leu Trp Gln Glu Cys Arg Lys Asn Gly Leu
            660                 665                 670

Arg Asn Ile Gln Leu Tyr Ser Trp Pro Glu His Cys Arg Thr Tyr Leu
        675                 680                 685

Thr Arg Ile Ala Gly Cys Arg Ile Arg Asn Pro Arg Trp Leu Met Asp
    690                 695                 700

Thr Pro Ala Asp Ala Ala Ala Glu Glu Glu Ala Leu Glu Asp Ser
705                 710                 715                 720

Leu Met Asp Val Gln Asp Leu Ser Leu Arg Leu Ser Ile Asp Gly Glu
                725                 730                 735

Arg Gly Ser Ser Met Asn Asp Ala Pro Ser Ser Asp Pro Gln Asp Ser
            740                 745                 750

Val Gln Arg Ile Met Asn Lys Ile Lys Arg Ser Ser Pro Ala Glu Thr
        755                 760                 765
```

-continued

```
Asp Gly Ala Lys Ile Pro Ala Glu Ala Ala Thr Ala Thr Ser Gly
    770                 775                 780

Ala Met Asn Lys Tyr Pro Leu Leu Arg Arg Arg Arg Leu Phe Val
785                 790                 795                 800

Ile Ala Val Asp Cys Tyr Gly Asp Asp Gly Ala Ser Lys Arg Met
                805                 810                 815

Leu Gln Val Ile Gln Glu Val Phe Arg Ala Val Arg Ser Asp Ser Gln
            820                 825                 830

Met Ser Arg Ile Ser Gly Phe Ala Leu Ser Thr Xaa Met Pro Leu Pro
        835                 840                 845

Glu Thr Leu Lys Leu Leu Gln Leu Gly Lys Ile Pro Pro Thr Asp Phe
    850                 855                 860

Asp Ala Leu Ile Cys Gly Ser Gly Ser Glu Val Tyr Tyr Pro Ser Thr
865                 870                 875                 880

Ala Gln Cys Val Asp Ala Gly Gly Arg Leu Arg Pro Asp Gln Asp Tyr
                885                 890                 895

Leu Leu His Ile Asn His Arg Trp Ser His Asp Gly Ala Lys Gln Thr
            900                 905                 910

Ile Ala Lys Leu Ala His Asp Gly Ser Gly Thr Asn Val Glu Pro Asp
        915                 920                 925

Val Glu Ser Cys Asn Pro His Cys Val Ser Phe Phe Ile Lys Asp Pro
    930                 935                 940

Asn Lys Val Arg Thr Met Asp Glu Met Arg Glu Arg Val Arg Met Arg
945                 950                 955                 960

Gly Leu Arg Cys His Leu Met Tyr Cys Arg Asn Ala Thr Arg Leu Gln
                965                 970                 975

Val Val Pro Leu Leu Ala Ser Arg Ser Gln Ala Leu Arg Tyr Leu Phe
            980                 985                 990

Val Arg Trp Gly Leu Ser Val Gly Asn Met Tyr Leu Ile Val Gly Glu
        995                 1000                1005

His Gly Asp Thr Asp His Glu Glu Met Leu Ser Gly Leu His Lys Thr
    1010                1015                1020

Val Ile Ile Arg Gly Val Thr Glu Lys Gly Ser Glu Gln Leu Val Arg
1025                1030                1035                1040

Ser Ser Gly Ser Tyr Gln Arg Glu Asp Val Val Pro Ser Glu Ser Pro
                1045                1050                1055

Leu Ile Ala Phe Thr Lys Gly Asp Leu Lys Ala Asp Glu Ile Met Arg
            1060                1065                1070

Ala Leu Lys Glu Val Thr Lys Ala Ala Ser Gly Met
        1075                1080
```

<210> SEQ ID NO 10
<211> LENGTH: 1049
<212> TYPE: PRT
<213> ORGANISM: Oryza sativa

<400> SEQUENCE: 10

```
Met Ala Gly Asn Glu Trp Ile Asn Gly Tyr Leu Glu Ala Ile Leu Asp
1               5                   10                  15

Ser Gly Ala Ala Gly Gly Gly Gly Gly Gly Val Asp Pro
            20                  25                  30

Arg Ser Pro Ala Ala Gly Ala Ala Ser Pro Arg Gly Pro His Met Asn
        35                  40                  45

Phe Asn Pro Thr His Tyr Phe Val Glu Glu Val Val Lys Gly Val Asp
    50                  55                  60
```

```
Glu Ser Asp Leu His Arg Thr Trp Ile Lys Val Ala Thr Arg Asn
 65                  70                  75                  80

Ala Arg Glu Arg Ser Thr Arg Leu Glu Asn Met Cys Trp Arg Ile Trp
             85                  90                  95

His Leu Ala Arg Lys Lys Lys Gln Leu Glu Leu Glu Gly Ile Leu Arg
                100                 105                 110

Ile Ser Ala Arg Arg Lys Glu Gln Glu Gln Val Arg Arg Glu Thr Ser
            115                 120                 125

Glu Asp Leu Ala Glu Asp Leu Phe Glu Gly Lys Ala Asp Thr Val
    130                 135                 140

Gly Glu Leu Ala Gln Gln Asp Thr Pro Met Lys Lys Lys Phe Gln Arg
145                 150                 155                 160

Asn Phe Ser Glu Leu Thr Val Ser Trp Ser Asp Glu Asn Lys Glu Lys
                165                 170                 175

Lys Leu Tyr Ile Val Leu Ile Ser Leu His Gly Leu Val Ser Gly Asp
                180                 185                 190

Asn Met Glu Leu Gly Arg Asp Ser Asp Thr Gly Gly Gln Val Lys Tyr
            195                 200                 205

Val Val Glu Leu Ala Arg Ala Leu Ala Met Met Pro Gly Val Tyr Arg
210                 215                 220

Val Asp Leu Phe Thr Arg Gln Val Ser Ser Pro Glu Val Asp Trp Ser
225                 230                 235                 240

Tyr Gly Glu Pro Thr Glu Met Leu Thr Pro Val Pro Leu Thr Glu Arg
                245                 250                 255

Glu Ala Val Arg Val Leu Val Arg Thr Leu Cys Ala Phe Arg Ala Val
            260                 265                 270

Gln Gly Thr Ser Thr Ser Val Lys Ser Pro Val Ala Leu Pro Pro Arg
            275                 280                 285

Val Cys Arg Arg Ser Ser Arg Ala Tyr Leu Asn Met Ser Lys Ala Leu
    290                 295                 300

Gly Glu Gln Val Ser Asn Gly Lys Leu Val Leu Pro Tyr Val Ile His
305                 310                 315                 320

Gly His Tyr Ala Asp Ala Gly Asp Val Ala Ala Leu Leu Ser Gly Ala
                325                 330                 335

Leu Asn Val Pro Met Val Leu Thr Gly His Ser Leu Gly Arg Asn Lys
                340                 345                 350

Leu Glu Gln Ile Met Lys Gln Gly Arg Met Ser Lys Glu Glu Ile Asp
            355                 360                 365

Ser Thr Tyr Lys Ile Met Arg Arg Ile Glu Gly Glu Glu Leu Ala Leu
    370                 375                 380

Asp Ala Thr Glu Pro Val Ile Thr Ser Thr Arg Gln Glu Asn Asp Glu
385                 390                 395                 400

Gln Trp Gly Leu Tyr Asp Gly Phe Asp Val Lys Leu Glu Lys Val Leu
                405                 410                 415

Arg Ala Arg Ala Arg Arg Gly Val Ser Cys His Gly Arg Phe Met Pro
            420                 425                 430

Arg Met Val Val Ile Pro Pro Gly Met Asp Phe Ser Ser Val Val Val
            435                 440                 445

Pro Glu Asp Thr Ser Asp Gly Asp Asp Gly Lys Asp Phe Glu Ile Ala
    450                 455                 460

Ser Pro Arg Ser Leu Pro Pro Ile Trp Ala Glu Val Met Arg Phe Leu
465                 470                 475                 480
```

-continued

```
Thr Asn Pro His Lys Pro Met Ile Leu Ala Leu Ser Arg Pro Asp Pro
            485                 490                 495
Lys Lys Asn Ile Thr Thr Leu Val Lys Ala Phe Gly Glu Cys Arg Pro
            500                 505                 510
Leu Arg Glu Leu Ala Asn Leu Ile Leu Ile Met Gly Asn Arg Asp Asp
            515                 520                 525
Ile Asp Glu Met Ser Ala Gly Asn Ala Ser Val Leu Thr Thr Val Leu
            530                 535                 540
Lys Leu Ile Asp Lys Tyr Asp Leu Tyr Gly Ser Val Ala Phe Pro Lys
545                 550                 555                 560
His His Lys Gln Ser Asp Val Pro Glu Ile Tyr Arg Leu Thr Gly Lys
            565                 570                 575
Met Lys Gly Val Phe Ile Asn Pro Ala Leu Val Glu Pro Phe Gly Leu
            580                 585                 590
Thr Leu Ile Glu Ala Ala His Gly Leu Pro Ile Val Ala Thr Lys
            595                 600                 605
Asn Gly Gly Pro Val Asp Ile Lys Asn Ala Leu Asn Asn Gly Leu Leu
            610                 615                 620
Val Asp Pro His Asp Gln His Ala Ile Ala Asp Ala Leu Leu Lys Leu
625                 630                 635                 640
Val Ala Asp Lys Asn Leu Trp Gln Glu Cys Arg Lys Asn Gly Leu Arg
            645                 650                 655
Asn Ile Gln Leu Tyr Ser Trp Pro Glu His Cys Arg Thr Tyr Leu Thr
            660                 665                 670
Arg Ile Ala Gly Cys Arg Ile Arg Asn Pro Arg Trp Leu Met Asp Thr
            675                 680                 685
Pro Ala Asp Ala Ala Glu Glu Glu Ala Leu Glu Asp Ser Leu
            690                 695                 700
Met Asp Val Gln Asp Leu Ser Leu His Leu Ser Ile Asp Gly Glu Arg
705                 710                 715                 720
Gly Ser Ser Met Asn Asp Ala Pro Ser Asp Pro Gln Asp Ser Val
            725                 730                 735
Gln Arg Ile Met Asn Lys Ile Lys Arg Ser Ser Pro Ala Asp Thr Asp
            740                 745                 750
Gly Ala Lys Ile Arg Gln Ala Ala Thr Ala Thr Ser Gly Ala Met
            755                 760                 765
Asn Lys Tyr Pro Leu Leu Arg Arg Arg Arg Leu Phe Val Ile Ala
            770                 775                 780
Val Asp Cys Tyr Gly Asp Asp Gly Ser Ala Ser Lys Arg Met Leu Gln
785                 790                 795                 800
Val Ile Gln Glu Val Phe Arg Ala Val Arg Ser Asp Ser Gln Met Ser
            805                 810                 815
Arg Ile Ser Gly Phe Ala Leu Ser Thr Ala Met Pro Leu Pro Glu Thr
            820                 825                 830
Leu Lys Leu Leu Gln Leu Gly Lys Ile Pro Pro Thr Asp Phe Asp Ala
            835                 840                 845
Leu Ile Cys Gly Ser Gly Ser Glu Val Tyr Tyr Pro Gly Thr Ala Gln
            850                 855                 860
Cys Val Asp Ala Gly Gly Leu Arg Pro Asp Gln Asp Tyr Leu Leu His
865                 870                 875                 880
Ile Asn His Arg Trp Ser His Asp Gly Ala Lys Gln Thr Ile Ala Asn
            885                 890                 895
Val Ala His Asp Gly Ser Gly Thr Asn Val Glu Pro Asp Val Glu Ser
```

```
                    900                 905                 910
Cys Asn Pro His Cys Val Ser Phe Phe Ile Lys Asp Pro Asn Lys Val
        915                 920                 925

Arg Thr Ala Asp Glu Met Arg Glu Arg Met Arg Met Arg Gly Leu Arg
    930                 935                 940

Cys His Leu Met Tyr Cys Arg Asn Ala Thr Arg Leu Gln Val Val Pro
945                 950                 955                 960

Leu Leu Ala Ser Arg Ser Gln Ala Leu Arg Tyr Leu Phe Val Arg Trp
            965                 970                 975

Gly Leu Ser Val Gly Asn Met Tyr Leu Ile Val Gly Glu His Gly Asp
        980                 985                 990

Thr Asp His Glu Glu Met Leu Ser Gly Leu His Lys Thr Val Ile Ile
        995                 1000                1005

Arg Gly Val Thr Glu Lys Gly Ser Glu Gln Leu Val Arg Ser Ser Gly
    1010                1015                1020

Ser Tyr Gln Arg Glu Asp Val Phe Pro Ser Glu Ser Pro Leu Ile Ala
1025                1030                1035                1040

Phe Thr Lys Gly Asp Leu Lys Ala Asp
            1045

<210> SEQ ID NO 11
<211> LENGTH: 1083
<212> TYPE: PRT
<213> ORGANISM: Arabidopsis thaliana

<400> SEQUENCE: 11

Met Ala Arg Asn Asp Trp Ile Asn Ser Tyr Leu Glu Ala Ile Leu Asp
1               5                   10                  15

Val Gly Thr Ser Lys Lys Lys Arg Phe Glu Ser Asn Ser Lys Ile Val
                20                  25                  30

Gln Lys Leu Gly Asp Ile Asn Ser Lys Asp His Gln Glu Lys Val Phe
            35                  40                  45

Gly Asp Met Asn Gly Lys Asp His Gln Glu Lys Val Phe Ser Pro Ile
        50                  55                  60

Lys Tyr Phe Val Glu Glu Val Val Asn Ser Phe Asp Glu Ser Asp Leu
65                  70                  75                  80

Tyr Lys Thr Trp Ile Lys Val Ile Ala Thr Arg Asn Thr Arg Glu Arg
                85                  90                  95

Ser Asn Arg Leu Glu Asn Ile Cys Trp Arg Ile Trp His Leu Ala Arg
            100                 105                 110

Lys Lys Lys Gln Ile Val Trp Asp Asp Gly Val Arg Leu Ser Lys Arg
        115                 120                 125

Arg Ile Glu Arg Glu Gln Gly Arg Asn Asp Ala Glu Glu Asp Leu Leu
    130                 135                 140

Ser Glu Leu Ser Glu Gly Glu Lys Asp Lys Asn Asp Gly Glu Lys Glu
145                 150                 155                 160

Lys Ser Glu Val Val Thr Thr Leu Glu Pro Pro Arg Asp His Met Pro
                165                 170                 175

Arg Ile Arg Ser Glu Met Gln Ile Trp Ser Glu Asp Asp Lys Ser Ser
            180                 185                 190

Arg Asn Leu Tyr Ile Val Leu Ile Arg Gln Val Glu Ile Gly Phe Ser
        195                 200                 205

Asp Leu Phe Val Val Phe Asn Met Leu Val Gly Leu Thr Trp Cys Leu
    210                 215                 220
```

-continued

```
Tyr Leu Val Pro Cys Phe Thr Asn Cys Ser Met His Gly Leu Val Arg
225                 230                 235                 240

Gly Glu Asn Met Glu Leu Gly Arg Asp Ser Asp Thr Gly Gly Gln Val
            245                 250                 255

Lys Tyr Val Val Glu Leu Ala Arg Ala Leu Ala Asn Thr Glu Gly Val
            260                 265                 270

His Arg Val Asp Leu Leu Thr Arg Gln Ile Ser Ser Pro Glu Val Asp
        275                 280                 285

Tyr Ser Tyr Gly Glu Pro Val Glu Met Leu Ser Cys Pro Pro Glu Gly
290                 295                 300

Ser Asp Ser Cys Gly Ser Tyr Ile Ile Arg Ile Pro Cys Gly Ser Arg
305                 310                 315                 320

Asp Lys Tyr Ile Pro Lys Glu Ser Leu Trp Pro His Ile Pro Glu Phe
                325                 330                 335

Val Asp Gly Ala Leu Asn His Ile Val Ser Ile Ala Arg Ser Leu Gly
            340                 345                 350

Glu Gln Val Asn Gly Lys Pro Ile Trp Pro Tyr Val Ile His Gly
        355                 360                 365

His Tyr Ala Asp Ala Gly Glu Val Ala Ala His Leu Ala Gly Ala Leu
    370                 375                 380

Asn Val Pro Met Val Leu Thr Gly His Ser Leu Gly Arg Asn Lys Phe
385                 390                 395                 400

Glu Gln Leu Leu Gln Gln Gly Arg Ile Thr Arg Glu Asp Ile Asp Arg
                405                 410                 415

Thr Tyr Lys Ile Met Arg Arg Ile Glu Ala Glu Gln Ser Leu Asp
            420                 425                 430

Ala Ala Glu Met Val Val Thr Ser Thr Arg Gln Glu Ile Asp Ala Gln
            435                 440                 445

Trp Gly Leu Tyr Asp Gly Phe Asp Ile Lys Leu Glu Arg Lys Leu Arg
        450                 455                 460

Val Arg Arg Arg Arg Gly Val Ser Cys Leu Gly Arg Tyr Met Pro Arg
465                 470                 475                 480

Met Val Val Ile Pro Pro Gly Met Asp Phe Ser Tyr Val Leu Thr Gln
                485                 490                 495

Asp Ser Gln Glu Pro Asp Gly Asp Leu Lys Ser Leu Ile Gly Pro Asp
            500                 505                 510

Arg Asn Gln Ile Lys Lys Pro Val Pro Pro Ile Trp Ser Glu Ile Met
        515                 520                 525

Arg Phe Phe Ser Asn Pro His Lys Pro Thr Ile Leu Ala Leu Ser Arg
530                 535                 540

Pro Asp His Lys Lys Asn Val Thr Thr Leu Val Lys Ala Phe Gly Glu
545                 550                 555                 560

Cys Gln Pro Leu Arg Glu Leu Ala Asn Leu Val Leu Ile Leu Gly Asn
                565                 570                 575

Arg Asp Asp Ile Glu Glu Met Pro Asn Ser Ser Val Val Leu Met
            580                 585                 590

Asn Val Leu Lys Leu Ile Asp Gln Tyr Asp Leu Tyr Gly Gln Val Ala
        595                 600                 605

Tyr Pro Lys His His Lys Gln Ser Glu Val Pro Asp Ile Tyr Arg Leu
    610                 615                 620

Ala Ala Lys Thr Lys Gly Val Phe Ile Asn Pro Ala Leu Val Glu Pro
625                 630                 635                 640

Phe Gly Leu Thr Leu Ile Glu Ala Ala Ala Tyr Gly Leu Pro Ile Val
```

-continued

```
                        645                 650                 655
Ala Thr Arg Asn Gly Gly Pro Val Asp Ile Val Lys Ala Leu Asn Asn
                    660                 665                 670
Gly Leu Leu Val Asp Pro His Asp Gln Gln Ala Ile Ser Asp Ala Leu
                675                 680                 685
Leu Lys Leu Val Ala Asn Lys His Leu Trp Ala Glu Cys Arg Lys Asn
            690                 695                 700
Gly Leu Lys Asn Ile His Arg Phe Ser Trp Pro Glu His Cys Arg Asn
705                 710                 715                 720
Tyr Leu Ser His Val Glu His Cys Arg Asn Arg His Pro Thr Ser Ser
                        725                 730                 735
Leu Asp Ile Met Lys Val Pro Glu Glu Leu Thr Ser Asp Ser Leu Arg
                    740                 745                 750
Asp Val Asp Asp Ile Ser Leu Arg Phe Ser Thr Glu Gly Asp Phe Thr
                755                 760                 765
Leu Asn Gly Glu Leu Asp Ala Gly Thr Arg Gln Lys Lys Leu Val Asp
            770                 775                 780
Ala Ile Ser Gln Met Asn Ser Met Lys Gly Cys Ser Ala Ala Ile Tyr
785                 790                 795                 800
Ser Pro Gly Arg Arg Gln Met Leu Phe Val Ala Val Asp Ser Tyr
                        805                 810                 815
Asp Asp Asn Gly Asn Ile Lys Ala Asn Leu Asn Glu Ile Ile Lys Asn
                    820                 825                 830
Met Ile Lys Ala Ala Asp Leu Thr Ser Gly Lys Gly Lys Ile Gly Phe
                835                 840                 845
Val Leu Ala Ser Gly Ser Ser Leu Gln Glu Val Val Asp Ile Thr Gln
            850                 855                 860
Lys Asn Leu Ile Asn Leu Glu Asp Phe Asp Ala Ile Val Cys Asn Ser
865                 870                 875                 880
Gly Ser Glu Ile Tyr Tyr Pro Trp Arg Asp Met Met Val Asp Ala Asp
                        885                 890                 895
Tyr Glu Thr His Val Glu Tyr Lys Trp Pro Gly Glu Ser Ile Arg Ser
                    900                 905                 910
Val Ile Leu Arg Leu Ile Cys Thr Glu Pro Ala Ala Glu Asp Asp Ile
                915                 920                 925
Thr Glu Tyr Ala Ser Ser Cys Ser Thr Arg Cys Tyr Ala Ile Ser Val
            930                 935                 940
Lys Gln Gly Val Lys Thr Arg Arg Val Asp Asp Leu Arg Gln Arg Leu
945                 950                 955                 960
Arg Met Arg Gly Leu Arg Cys Asn Ile Val Tyr Thr His Ala Ala Thr
                        965                 970                 975
Arg Leu Asn Val Ile Pro Leu Cys Ala Ser Arg Ile Gln Ala Leu Arg
                    980                 985                 990
Tyr Leu Ser Ile Arg Trp Gly Ile Asp Met Ser Lys Thr Val Phe Phe
                995                 1000                1005
Leu Gly Glu Lys Gly Asp Thr Asp Tyr Glu Asp Leu Leu Gly Gly Leu
            1010                1015                1020
His Lys Thr Ile Ile Leu Lys Gly Val Val Gly Ser Asp Ser Glu Lys
1025                1030                1035                1040
Leu Leu Arg Ser Glu Glu Asn Phe Lys Arg Glu Asp Ala Val Pro Gln
                        1045                1050                1055
Glu Ser Pro Asn Ile Ser Tyr Val Lys Glu Asn Gly Gly Ser Gln Glu
                    1060                1065                1070
```

Ile Met Ser Thr Leu Glu Ala Tyr Gly Ile Lys
        1075            1080

<210> SEQ ID NO 12
<211> LENGTH: 963
<212> TYPE: PRT
<213> ORGANISM: Arabidopsis thaliana

<400> SEQUENCE: 12

Met Ala Gly Asn Asp Asn Trp Ile Asn Ser Tyr Leu Asp Gly Ile Leu
1               5                   10                  15

Asp Ala Gly Lys Ala Ala Ile Gly Gly Asn Arg Pro Ser Leu Leu Leu
            20                  25                  30

Arg Glu Arg Gly His Phe Ser Pro Ala Arg Tyr Phe Val Glu Glu Val
        35                  40                  45

Ile Thr Gly Tyr Asp Glu Thr Asp Leu Tyr Lys Thr Trp Leu Arg Ala
    50                  55                  60

Asn Ala Met Arg Ser Arg Arg Glu Glu His Ala Leu Glu Asn Met Thr
65                  70                  75                  80

Trp Arg Ile Trp Asn Leu Ala Arg Lys Lys Glu Phe Glu Lys Glu
                85                  90                  95

Glu Ala Cys Arg Leu Ser Lys Arg Gln Pro Thr Glu Lys Thr Arg
            100                 105                 110

Ala Asp Ala Thr Ala Asp Met Ser Glu Asp Leu Phe Glu Gly Glu Lys
        115                 120                 125

Gly Glu Asp Ala Gly Asp Pro Ser Val Ala Tyr Gly Asp Ser Thr Thr
    130                 135                 140

Gly Ser Ser Pro Lys Thr Ser Ser Ile Asp Lys Leu Tyr Ile Val Leu
145                 150                 155                 160

Ile Ser Leu His Gly Leu Val Arg Gly Glu Asn Met Glu Leu Gly Arg
                165                 170                 175

Asp Ser Asp Thr Gly Gly Gln Val Lys Tyr Val Val Glu Leu Ala Lys
            180                 185                 190

Ala Leu Ser Ser Ser Pro Gly Val Tyr Arg Val Asp Leu Leu Thr Arg
        195                 200                 205

Gln Ile Leu Ala Pro Asn Phe Asp Arg Ser Tyr Gly Glu Pro Ala Glu
    210                 215                 220

Leu Leu Val Ser Thr Ser Gly Lys Asn Ser Lys Gln Glu Lys Gly Glu
225                 230                 235                 240

Asn Ser Gly Ala Tyr Ile Ile Arg Ile Pro Phe Gly Pro Lys Asp Lys
                245                 250                 255

Tyr Leu Ala Lys Glu His Leu Trp Pro Phe Ile Gln Glu Phe Val Asp
            260                 265                 270

Gly Ala Leu Ser His Ile Val Arg Met Ser Lys Ala Ile Gly Glu Glu
        275                 280                 285

Thr Gly Arg Gly His Pro Val Trp Pro Ser Val Ile His Gly His Tyr
    290                 295                 300

Ala Ser Ala Gly Ile Ala Ala Ala Leu Leu Leu Gly Ala Leu Asn Leu
305                 310                 315                 320

Pro Met Ala Phe Thr Gly His Phe Leu Gly Lys Asp Lys Leu Glu Gly
                325                 330                 335

Leu Leu Lys Gln Gly Arg Gln Thr Arg Glu Gln Ile Asn Met Thr Tyr
            340                 345                 350

Lys Ile Met Cys Arg Ile Glu Ala Glu Glu Leu Ser Leu Asp Ala Ser

-continued

```
            355                 360                 365
Glu Ile Val Ile Ala Ser Thr Arg Gln Glu Ile Glu Glu Gln Trp Asn
370                 375                 380

Leu Tyr Asp Gly Phe Glu Val Ile Leu Ala Arg Lys Leu Arg Ala Arg
385                 390                 395                 400

Val Lys Arg Gly Ala Asn Cys Tyr Gly Arg Phe Met Pro Arg Met Val
                    405                 410                 415

Ile Ile Pro Pro Gly Val Glu Phe Gly His Ile Ile His Asp Phe Asp
                420                 425                 430

Met Asp Gly Glu Glu Asn Pro Ser Pro Ala Ser Glu Asp Pro Pro
            435                 440                 445

Ile Trp Ser Gln Ile Met Arg Phe Phe Thr Asn Pro Arg Lys Pro Met
450                 455                 460

Ile Leu Ala Val Ala Arg Pro Tyr Pro Glu Lys Asn Ile Thr Thr Leu
465                 470                 475                 480

Val Lys Ala Phe Gly Glu Cys Arg Pro Leu Arg Glu Leu Ala Asn Leu
                485                 490                 495

Thr Leu Ile Met Gly Asn Arg Glu Ala Ile Ser Lys Met His Asn Met
                500                 505                 510

Ser Ala Ala Val Leu Thr Ser Val Leu Thr Leu Ile Asp Glu Tyr Asp
                515                 520                 525

Leu Tyr Gly Gln Val Ala Tyr Pro Lys His His Lys His Ser Glu Val
530                 535                 540

Pro Asp Ile Tyr Arg Leu Ala Ala Arg Thr Lys Gly Ala Phe Val Asn
545                 550                 555                 560

Val Ala Tyr Phe Glu Gln Phe Gly Val Thr Leu Ile Glu Ala Ala Met
                565                 570                 575

Asn Gly Leu Pro Ile Ile Ala Thr Lys Asn Gly Ala Pro Val Glu Ile
                580                 585                 590

Asn Gln Val Leu Asn Asn Gly Leu Leu Val Asp Pro His Asp Gln Asn
            595                 600                 605

Ala Ile Ala Asp Ala Leu Tyr Lys Leu Leu Ser Asp Lys Gln Leu Trp
            610                 615                 620

Ser Arg Cys Arg Glu Asn Gly Leu Thr Asn Ile His Gln Phe Ser Trp
625                 630                 635                 640

Pro Glu His Cys Lys Asn Tyr Leu Ser Arg Ile Leu Thr Leu Gly Pro
                645                 650                 655

Arg Ser Pro Ala Ile Gly Asn Arg Glu Glu Arg Ser Asn Thr Pro Ile
                660                 665                 670

Ser Gly Arg Arg Gln Ile Ile Val Ile Ser Val Asp Ser Val Asn Lys
                675                 680                 685

Glu Asp Leu Val Arg Ile Ile Arg Asn Ala Ile Glu Val Ile His Thr
690                 695                 700

Gln Asn Met Ser Gly Ser Ala Gly Phe Val Leu Ser Thr Ser Leu Thr
705                 710                 715                 720

Ile Ser Glu Ile His Ser Leu Leu Leu Ser Gly Gly Met Leu Pro Thr
                725                 730                 735

Asp Phe Asp Ala Phe Ile Cys Asn Ser Gly Ser Asn Ile Tyr Tyr Pro
                740                 745                 750

Ser Tyr Ser Gly Glu Thr Pro Asn Asn Ser Lys Ile Thr Phe Ala Leu
                755                 760                 765

Asp Gln Asn His Gln Ser His Ile Glu Tyr Arg Trp Gly Gly Glu Gly
770                 775                 780
```

```
Leu Arg Lys Tyr Leu Val Lys Trp Ala Thr Ser Val Val Glu Arg Lys
785                 790                 795                 800

Gly Arg Thr Glu Arg Gln Ile Ile Phe Glu Asp Pro Glu His Ser Ser
            805                 810                 815

Ala Tyr Cys Leu Ala Phe Arg Val Val Asn Pro Asn His Leu Pro Pro
            820                 825                 830

Leu Lys Glu Leu Arg Lys Leu Met Arg Ile Gln Ser Leu Arg Cys Asn
            835                 840                 845

Ala Leu Tyr Asn His Ser Ala Thr Arg Leu Ser Val Val Pro Ile His
        850                 855                 860

Ala Ser Arg Ser Gln Ala Leu Arg Tyr Leu Cys Ile Arg Trp Gly Ile
865                 870                 875                 880

Glu Val Pro Asn Val Ala Val Leu Val Gly Glu Ser Gly Asp Ser Asp
                885                 890                 895

Tyr Glu Glu Leu Leu Gly Gly Leu His Arg Thr Val Ile Leu Lys Gly
            900                 905                 910

Glu Phe Asn Thr Pro Ala Asn Arg Ile His Thr Val Arg Arg Tyr Pro
        915                 920                 925

Leu Gln Asp Val Val Pro Leu Asp Ser Ser Asn Ile Thr Gly Val Glu
    930                 935                 940

Gly Tyr Thr Thr Asp Asp Leu Lys Ser Ala Leu Gln Gln Met Gly Ile
945                 950                 955                 960

Leu Thr Gln

<210> SEQ ID NO 13
<211> LENGTH: 963
<212> TYPE: PRT
<213> ORGANISM: Saccharum officinarum

<400> SEQUENCE: 13

Met Ala Gly Asn Asp Asn Trp Ile Asn Ser Tyr Leu Asp Gly Ile Leu
  1               5                  10                  15

Asp Ala Gly Lys Ala Ala Ile Gly Gly Asn Arg Pro Ser Leu Leu Leu
            20                  25                  30

Arg Glu Arg Gly His Phe Ser Pro Ala Arg Tyr Phe Val Glu Glu Val
        35                  40                  45

Ile Thr Gly Tyr Asp Glu Thr Asp Leu Tyr Lys Thr Trp Leu Arg Ala
    50                  55                  60

Asn Ala Met Arg Ser Arg Arg Glu Glu His Ala Leu Glu Asn Met Thr
65                  70                  75                  80

Trp Arg Ile Trp Asn Leu Ala Arg Lys Lys Glu Phe Glu Lys Glu
                85                  90                  95

Glu Ala Cys Arg Leu Ser Lys Arg Gln Pro Glu Thr Glu Lys Thr Arg
            100                 105                 110

Ala Asp Ala Thr Ala Asp Met Ser Glu Asp Leu Phe Glu Gly Glu Lys
        115                 120                 125

Gly Glu Asp Ala Gly Asp Pro Ser Val Ala Tyr Gly Asp Ser Thr Thr
    130                 135                 140

Gly Ser Pro Lys Thr Ser Ser Ile Asp Lys Leu Tyr Ile Val Leu
145                 150                 155                 160

Ile Ser Leu His Gly Leu Val Arg Gly Glu Asn Met Glu Leu Gly Arg
                165                 170                 175

Asp Ser Asp Thr Gly Gly Gln Val Lys Tyr Val Val Glu Leu Ala Lys
            180                 185                 190
```

-continued

```
Ala Leu Ser Ser Ser Pro Gly Val Tyr Arg Val Asp Leu Leu Thr Arg
        195                 200                 205
Gln Ile Leu Ala Pro Asn Phe Asp Arg Ser Tyr Gly Glu Pro Ala Glu
    210                 215                 220
Leu Leu Val Ser Thr Ser Gly Lys Asn Ser Lys Gln Glu Lys Gly Glu
225                 230                 235                 240
Asn Ser Gly Ala Tyr Ile Ile Arg Ile Pro Phe Gly Pro Lys Asp Lys
                245                 250                 255
Tyr Leu Ala Lys Glu His Leu Trp Pro Phe Ile Gln Glu Phe Val Asp
            260                 265                 270
Gly Ala Leu Ser His Ile Val Arg Met Ser Lys Ala Ile Gly Glu Glu
        275                 280                 285
Thr Gly Arg Gly His Pro Val Trp Pro Ser Val Ile His Gly His Tyr
    290                 295                 300
Ala Ser Ala Gly Ile Ala Ala Leu Leu Leu Gly Ala Leu Asn Leu
305                 310                 315                 320
Pro Met Ala Phe Thr Gly His Phe Leu Gly Lys Asp Lys Leu Glu Gly
                325                 330                 335
Leu Leu Lys Gln Gly Arg Gln Thr Arg Glu Gln Ile Asn Met Thr Tyr
            340                 345                 350
Lys Ile Met Cys Arg Ile Glu Ala Glu Glu Leu Ser Leu Asp Ala Ser
        355                 360                 365
Glu Ile Val Ile Ala Ser Thr Arg Gln Glu Ile Glu Glu Gln Trp Asn
    370                 375                 380
Leu Tyr Asp Gly Phe Glu Val Ile Leu Ala Arg Lys Leu Arg Ala Arg
385                 390                 395                 400
Val Lys Arg Gly Ala Asn Cys Tyr Gly Arg Phe Met Pro Arg Met Val
                405                 410                 415
Ile Ile Pro Pro Gly Val Glu Phe Gly His Ile Ile His Asp Phe Asp
            420                 425                 430
Met Asp Gly Glu Glu Glu Asn Pro Ser Pro Ala Ser Glu Asp Pro Pro
        435                 440                 445
Ile Trp Ser Gln Ile Met Arg Phe Phe Thr Asn Pro Arg Lys Pro Met
    450                 455                 460
Ile Leu Ala Val Ala Arg Pro Tyr Pro Glu Lys Asn Ile Thr Thr Leu
465                 470                 475                 480
Val Lys Ala Phe Gly Glu Cys Arg Pro Leu Arg Glu Leu Ala Asn Leu
                485                 490                 495
Thr Leu Ile Met Gly Asn Arg Glu Ala Ile Ser Lys Met His Asn Met
            500                 505                 510
Ser Ala Ala Val Leu Thr Ser Val Leu Thr Leu Ile Asp Glu Tyr Asp
        515                 520                 525
Leu Tyr Gly Gln Val Ala Tyr Pro Lys His His Lys His Ser Glu Val
    530                 535                 540
Pro Asp Ile Tyr Arg Leu Ala Ala Arg Thr Lys Gly Ala Phe Val Asn
545                 550                 555                 560
Val Ala Tyr Phe Glu Gln Phe Gly Val Thr Leu Ile Glu Ala Ala Met
                565                 570                 575
Asn Gly Leu Pro Ile Ile Ala Thr Lys Asn Gly Ala Pro Val Glu Ile
            580                 585                 590
Asn Gln Val Leu Asn Asn Gly Leu Leu Val Asp Pro His Asp Gln Asn
        595                 600                 605
```

```
Ala Ile Ala Asp Ala Leu Tyr Lys Leu Leu Ser Asp Lys Gln Leu Trp
        610             615                 620

Ser Arg Cys Arg Glu Asn Gly Leu Thr Asn Ile His Gln Phe Ser Trp
625             630                 635                 640

Pro Glu His Cys Lys Asn Tyr Leu Ser Arg Ile Leu Thr Leu Gly Pro
                645                 650                 655

Arg Ser Pro Ala Ile Gly Asn Arg Glu Glu Arg Ser Asn Thr Pro Ile
                660                 665                 670

Ser Gly Arg Arg Gln Ile Ile Val Ile Ser Val Asp Ser Val Asn Lys
            675                 680                 685

Glu Asp Leu Val Arg Ile Ile Arg Asn Ala Ile Glu Val Ile His Thr
        690                 695                 700

Gln Asn Met Ser Gly Ser Ala Gly Phe Val Leu Ser Thr Ser Leu Thr
705                 710                 715                 720

Ile Ser Glu Ile His Ser Leu Leu Leu Ser Gly Gly Met Leu Pro Thr
                725                 730                 735

Asp Phe Asp Ala Phe Ile Cys Asn Ser Gly Ser Asn Ile Tyr Tyr Pro
                740                 745                 750

Ser Tyr Ser Gly Glu Thr Pro Asn Asn Ser Lys Ile Thr Phe Ala Leu
            755                 760                 765

Asp Gln Asn His Gln Ser His Ile Glu Tyr Arg Trp Gly Gly Glu Gly
        770                 775                 780

Leu Arg Lys Tyr Leu Val Lys Trp Ala Thr Ser Val Val Glu Arg Lys
785                 790                 795                 800

Gly Arg Thr Glu Arg Gln Ile Ile Phe Glu Asp Pro Glu His Ser Ser
                805                 810                 815

Ala Tyr Cys Leu Ala Phe Arg Val Val Asn Pro Asn His Leu Pro Pro
                820                 825                 830

Leu Lys Glu Leu Arg Lys Leu Met Arg Ile Gln Ser Leu Arg Cys Asn
            835                 840                 845

Ala Leu Tyr Asn His Ser Ala Thr Arg Leu Ser Val Val Pro Ile His
        850                 855                 860

Ala Ser Arg Ser Gln Ala Leu Arg Tyr Leu Cys Ile Arg Trp Gly Ile
865                 870                 875                 880

Glu Val Pro Asn Val Ala Val Leu Val Gly Glu Ser Gly Asp Ser Asp
                885                 890                 895

Tyr Glu Glu Leu Leu Gly Gly Leu His Arg Thr Val Ile Leu Lys Gly
                900                 905                 910

Glu Phe Asn Thr Pro Ala Asn Arg Ile His Thr Val Arg Arg Tyr Pro
            915                 920                 925

Leu Gln Asp Val Val Pro Leu Asp Ser Ser Asn Ile Thr Gly Val Glu
        930                 935                 940

Gly Tyr Thr Thr Asp Asp Leu Lys Ser Ala Leu Gln Gln Met Gly Ile
945                 950                 955                 960

Leu Thr Gln

<210> SEQ ID NO 14
<211> LENGTH: 720
<212> TYPE: PRT
<213> ORGANISM: Synechocystis sp.

<400> SEQUENCE: 14

Met Ser Tyr Ser Ser Lys Tyr Ile Leu Leu Ile Ser Val His Gly Leu
  1               5                   10                  15
```

```
Ile Arg Gly Glu Asn Leu Glu Leu Gly Arg Asp Ala Asp Thr Gly Gly
             20                  25                  30

Gln Thr Lys Tyr Val Leu Glu Leu Ala Arg Ala Leu Val Lys Asn Pro
         35                  40                  45

Gln Val Ala Arg Val Asp Leu Leu Thr Arg Leu Ile Lys Asp Pro Lys
     50                  55                  60

Val Asp Ala Asp Tyr Ala Gln Pro Arg Glu Leu Ile Gly Asp Arg Ala
 65                  70                  75                  80

Gln Ile Val Arg Ile Glu Cys Gly Pro Glu Glu Tyr Ile Ala Lys Glu
                 85                  90                  95

Met Leu Trp Asp Tyr Leu Asp Asn Phe Ala Asp His Ala Leu Asp Tyr
             100                 105                 110

Leu Lys Glu Gln Pro Glu Leu Pro Asp Val Ile His Ser His Tyr Ala
         115                 120                 125

Asp Ala Gly Tyr Val Gly Thr Arg Leu Ser His Gln Leu Gly Ile Pro
    130                 135                 140

Leu Val His Thr Gly His Ser Leu Gly Arg Ser Lys Arg Thr Arg Leu
145                 150                 155                 160

Leu Leu Ser Gly Ile Lys Ala Asp Glu Ile Glu Ser Arg Tyr Asn Met
                165                 170                 175

Ala Arg Arg Ile Asn Ala Glu Glu Thr Leu Gly Ser Ala Ala Arg
            180                 185                 190

Val Ile Thr Ser Thr His Gln Glu Ile Ala Glu Gln Tyr Ala Gln Tyr
        195                 200                 205

Asp Tyr Tyr Gln Pro Asp Gln Met Leu Val Ile Pro Pro Gly Thr Asp
    210                 215                 220

Leu Glu Lys Phe Tyr Pro Pro Lys Gly Asn Glu Trp Glu Thr Pro Ile
225                 230                 235                 240

Val Gln Glu Leu Gln Arg Phe Leu Arg His Pro Arg Lys Pro Ile Ile
                245                 250                 255

Leu Ala Leu Ser Arg Pro Asp Pro Arg Lys Asn Ile His Lys Leu Ile
            260                 265                 270

Ala Ala Tyr Gly Gln Ser Pro Gln Leu Gln Ala Gln Ala Asn Leu Val
        275                 280                 285

Ile Val Ala Gly Asn Arg Asp Asp Ile Thr Asp Leu Asp Gln Gly Pro
    290                 295                 300

Arg Glu Val Leu Thr Asp Leu Leu Thr Ile Asp Arg Tyr Asp Leu
305                 310                 315                 320

Tyr Gly Lys Val Ala Tyr Pro Lys Gln Asn Gln Ala Glu Asp Val Tyr
                325                 330                 335

Ala Leu Phe Arg Leu Thr Ala Leu Ser Gln Gly Val Phe Ile Asn Pro
            340                 345                 350

Ala Leu Thr Glu Pro Phe Gly Leu Thr Leu Ile Glu Ala Ala Cys
        355                 360                 365

Gly Val Pro Ile Val Ala Thr Glu Asp Gly Gly Pro Val Asp Ile Ile
    370                 375                 380

Lys Asn Cys Gln Asn Gly Tyr Leu Ile Asn Pro Leu Asp Glu Val Asp
385                 390                 395                 400

Ile Ala Asp Lys Leu Leu Lys Val Leu Asn Asp Lys Gln Gln Trp Gln
                405                 410                 415

Phe Leu Ser Glu Ser Gly Leu Glu Gly Val Lys Arg His Tyr Ser Trp
            420                 425                 430

Pro Ser His Val Glu Ser Tyr Leu Glu Ala Ile Asn Ala Leu Thr Gln
```

-continued

```
             435                 440                 445
Gln Thr Ser Val Leu Lys Arg Ser Asp Leu Lys Arg Arg Arg Thr Leu
    450                 455                 460

Tyr Tyr Asn Gly Ala Leu Val Thr Ser Leu Asp Gln Asn Leu Leu Gly
465                 470                 475                 480

Ala Leu Gln Gly Gly Leu Pro Gly Asp Arg Gln Thr Leu Asp Glu Leu
                485                 490                 495

Leu Glu Val Leu Tyr Gln His Arg Lys Asn Val Gly Phe Cys Ile Ala
                500                 505                 510

Thr Gly Arg Arg Leu Asp Ser Val Leu Lys Ile Leu Arg Glu Tyr Arg
            515                 520                 525

Ile Pro Gln Pro Asp Met Leu Ile Thr Ser Met Gly Thr Glu Ile Tyr
    530                 535                 540

Ser Ser Pro Asp Leu Ile Pro Asp Gln Ser Trp Arg Asn His Ile Asp
545                 550                 555                 560

Tyr Leu Trp Asn Arg Asn Ala Ile Val Arg Ile Leu Gly Glu Leu Pro
                565                 570                 575

Gly Leu Ala Leu Gln Pro Lys Glu Glu Leu Ser Ala Tyr Lys Ile Ser
            580                 585                 590

Tyr Phe Tyr Asp Ala Ala Ile Ala Pro Asn Leu Glu Glu Ile Arg Gln
        595                 600                 605

Leu Leu His Lys Gly Glu Gln Thr Val Asn Thr Ile Ile Ser Phe Gly
    610                 615                 620

Gln Phe Leu Asp Ile Leu Pro Ile Arg Ala Ser Lys Gly Tyr Ala Val
625                 630                 635                 640

Arg Trp Leu Ser Gln Gln Trp Asn Ile Pro Leu Glu His Val Phe Thr
                645                 650                 655

Ala Gly Gly Ser Gly Ala Asp Glu Asp Met Met Arg Gly Asn Thr Leu
            660                 665                 670

Ser Val Val Val Ala Asn Arg His His Glu Glu Leu Ser Asn Leu Gly
            675                 680                 685

Glu Ile Glu Pro Ile Tyr Phe Ser Glu Lys Arg Tyr Ala Ala Gly Ile
    690                 695                 700

Leu Asp Gly Leu Ala His Tyr Arg Phe Phe Glu Leu Leu Asp Pro Val
705                 710                 715                 720
```